(12) United States Patent
Gubler et al.

(10) Patent No.: US 6,271,440 B1
(45) Date of Patent: Aug. 7, 2001

(54) PLANT REGULATORY PROTEINS III

(75) Inventors: Franz Jacques Gubler, Lyneham; John Viggo Jacobsen, Weetangera, both of (AU)

(73) Assignee: The Australian National University, Acton (AU)

(*) Notice: Subject to any disclaimer, the term of this patent is extended or adjusted under 35 U.S.C. 154(b) by 0 days.

(21) Appl. No.: 08/997,251

(22) Filed: Dec. 23, 1997

Related U.S. Application Data

(63) Continuation of application No. PCT/AU96/00383, filed on Jun. 21, 1996.

(30) Foreign Application Priority Data

Jun. 23, 1995 (AU) .............................................. PN3779/95
Nov. 9, 1995 (AU) .............................................. PN6470/95

(51) Int. Cl.$^7$ ............................. A01H 1/00; C07H 21/04; C07K 14/415; C12N 5/14
(52) U.S. Cl. ........................ 800/284; 536/23.6; 536/23.1; 800/278; 800/285; 800/295; 435/69.1; 435/471; 435/195; 435/410; 435/419
(58) Field of Search ................................... 536/23.6, 23.1; 800/278, 284, 295, 285; 435/69.1, 471, 195, 410, 419

(56) References Cited

PUBLICATIONS

Napoli et al. The Plant Cell. 1989. vol. 2:278–289.*
Wan et al. Plant Physiol. 1994. vol. 104: 37–48.*
Carvalho et al. The EMBO J. 1992. vol. 11: 2995–2602.*
Wissenbach et al. Plant Journal. vol. 4: 411–422, 1993.*
Ausubel et al. Short Protocols in Molecular Biology. 1989.*
Urao et al. The Plant Cell. 1993. vol. 5: 1529–1539.*
Gubler, Frank and Jacobsen, J.V., "Gibberellin–responsive elements in the promoter of a barley high–pI α–amylase gene," (1992) *The Plant Cell* 4:1435–1441.
Jacobsen, J.V. and Gubler, F., "GARC and DNA–binding proteins: the new wave in GA action research," (1993) In: *The Past, Present and Future of Plant Biology*, T.–H.D. Ho and H. Pakrasi, eds (St. Louis, MO: Department of Biology, Washington University), pp. 45–49.
Lanahan, M.B. et al., "A gibberellin response complex in cereal α–amylase gene promoters," (1992) *The Plant Cell* 4:203–211.
Rogers, John C. and Rogers, Sally W., "Definition and functional implications of gibberellin and abscisic acid cis–acting hormone response complexes," (1992) *The Plant Cell* 4:1443–1451.
Rushton, P.J. et al., "Aleurone nuclear proteins bind to similar elements in the promter regions of two gibberellin–regulated α–amylase genes," (1992) *Plant Molecular Biology* 19:891–901.
Rushton, P.J. et al., "Members of a new family of DNA–binding proteins bind to a conserved cis–element in the promoters of α–Amy2 genes," (1995) *Plant Molecular Biology* 29:691–702.
Skriver, K. et al., "Cis–acting DNA elements responsive to gibberellin and its antagonist abscisic acid," (1991) *Proc. Natl. Acad. Sci.* USA 88:7266–7270.
Sutliff, T.D. et al., "Gibberellin treatment stimulates nuclear factor binding to the gibberellin response complex in a barley α–amylase promoter," (1993) *The Plant Cell* 5:1681–1692.
Gubler, F. et al., "Gibberellin–Regulated Expression of a myb Gene in Barley Aleurone Cells: Evidence for Myb Transactivation of a High–pI α–Amylase Gene Promoter," (1995) *The Plant Cell* 7:1879–1891.

* cited by examiner

*Primary Examiner*—Phuong T. Bui
(74) *Attorney, Agent, or Firm*—Greenlee, Winner and Sullivan, P.C.

(57) ABSTRACT

The invention relates generally to genetic constructs which are useful in regulating the synthesis of malting enzymes in plants. More particularly, the present invention relates to nucleic acid molecules encoding gibberellin-regulated MYB polypeptides, for example the barley and rice GAMyb genetic sequences and transcriptionally-modulating parts and/or immunologically interactive parts thereof. The genetic sequences of the invention are introduced into plant cells, in particular monocotyledonous plant cells such as those derived from barley, wheat, maize, rye, rice or sorghum, where their expression in either the sense or antisense orientation modulates the expression of hydrolytic malting enzymes which are normally regulated by GAMYB polypeptides. The genetic sequences of the invention are therefore useful in the production of plants with altered malting properties.

25 Claims, 28 Drawing Sheets

Probes

Figure 1:
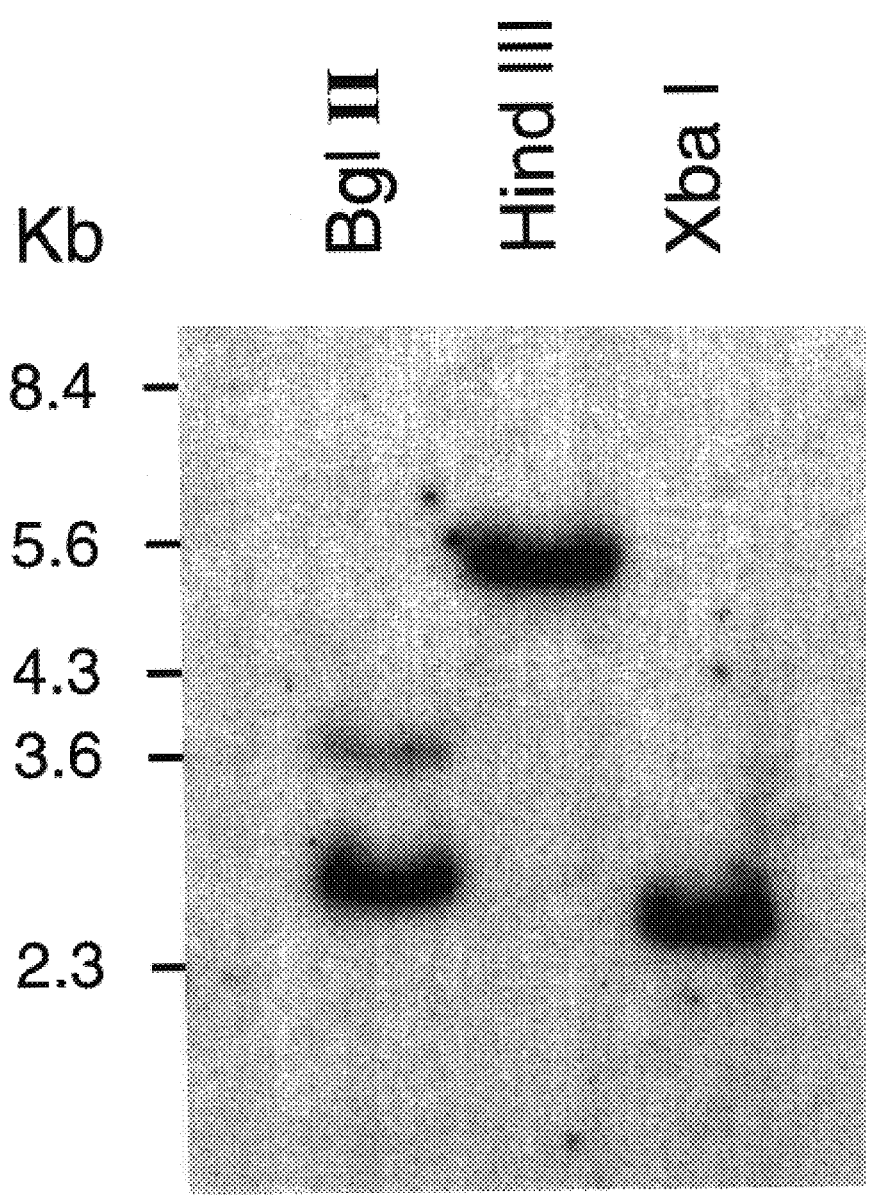

```
GGCCGATAACAAACTCCGGCCG    w
............CTCGAG....    m1
.........G............    m2
...............G......    m3
..................G...    m4
....................A.    m5
```

FIGURE 6a

```
         Pyrimidine                    TAACAAA                      TATCCAC
            box                          box                          box
      ┌────┐                         ┌──────┐                      ┌──────┐
  -171                                                                    -115
  CGCCTTTTGAGCTCACCGTACCGGCCGATAACAAACTCCGGCCGACATATCCACTGG  1
  ..................G...........................................  2
  ..................G...........................................  3

1 = Am(-174)IGN    2 = mTAACAAA-2    3 = mTAACAAA-3
  1 = Am-3
```

FIGURE 8a

| Constructs | Without Hormone | $10^{-6}$ M GA$_3$ |
|---|---|---|
| EII.IGN + p113 Act1.cas | 24.2 ± 4.9 | 100.0 ± 17.7 |
| EII.IGN + Act1.*GAmyb* | 554.5 ± 107.6 | 803.3 ± 186.5 |
| mlo22 + p113 Act1.cas | 4.7 ± 1.3 | 100.0 ± 23.3 |
| mlo22 + Act1.*GAmyb* | 153 ± 27.1 | 229.0 ± 35.3 |
| CBG1 + p113 Act1.cas | 7.1 ± 3.8 | 100.0 ± 17.2 |
| CBG1 + Act1.*GAmyb* | 118.1 ± 29.0 | 232.1 ± 65.8 |

| Constructs | Without Hormone | $10^{-6}$ M ABA |
|---|---|---|
| Dhn7(-935).IGN + p113 Act1.cas | 5.6 ± 1.4 | 100.0 ± 25.0 |
| Dhn7(-935).IGN + Act1.*GAmyb* | 28.4 ± 7.0 | 131.6 ± 19.8 |

```
MYRVKSESDCEMIHQE.QMDSPVADDGSS.GGSPHRGGGPPLKKGPWTSA        48
||||||||||||||||  ||||||||  :||||||||| ||||||||||||
MYRVKSESDCEMMHQEDQMDSPVGDDGSSGGGSPHRGGGPPLKKGPWTSA        50

EDAILVDYVKKHGEGNWNAVQKNTGLFRCGKSCRLRWANHLRPNLKKGAF        98
||||||||||||||||||||||||||||||||||||||||||||||||||
EDAILVDYVKKHGEGNWNAVQKNTGLFRCGKSCRLRWANHLRPNLKKGAF       100

TAEEERLIIQLHSKMGNKWARMAAHLPGRTDNEIKNYWNTRIKRCQRAGL       148
 |.||||||||||||||||||||||||||||||||||||||||||||||||
TPEEERLIIQLHSKMGNKWARMAAHLPGRTDNEIKNYWNTRIKRCQRAGL       150

PIYPTSVCNQSSNEDQQCSSDFDCGENLSNDLLNANGLYLPDFTCDNFIA       198
||||.||||||||||||||.|||.|||||||.||.||||||||||||||
PIYPASVCNQSSNEDQQGSSDFNCGENLSSDLLNGNGLYLPDFTCDNFIA       200
```

FIGURE 12a

```
NSEALPYAPHLSAVSISNLLGQSFASKSCSFMDQVNQTGMLKQSDGVLPG         248
|| ||| || ||| ||| ||| ||| || |||| ||||||| |||| ||
NSEALSYAPQLSAVSISSLLGQSFASKNCGFMDQVNQAGMLKQSDPLLPG         250

LSDTINGVISSVDQFSNDSEKLKQAVGFDYLHEANSTSKIIAPFGGALNG         298
||||||| ||||||||||||||||| |||||||||| |||||||||| |
LSDTINGALSSVDQFSNDSEKLKQALGFDYLHEANSSSKIIAPFGGALTG         300

SHAFLNGNFSASRPTSGPLKMELPSLQDTESDPNSWLKYTVAPALQPTEL         348
||||||| ||| || ||||||||||||||||||||||||||||| ||||
SHAFLNGTFSTSRTINGPLKMELPSLQDTESDPNSWLKYTVAPAMQPTEL         350

VDPYLQSPAATPSVKSECASPRNSGLLEELIHEAQTLRSGKNQQTSVISS         398
|||||||| ||||||||||||||||||||||||||| |||||||| |||
VDPYLQSPTATPSVKSECASPRNSGLLEELIHEAQGLRSGKNQQLSVRSS         400
```

FIGURE 12b

```
SSSVGTPCNTTVLSPEFDMCQEYWEEQHPGPFLNDCAPFSGNSFTESTPP 448
|||| ::||||||||:|||:||||| |||  ||::|||:|| :|:|:
SSSVSTPCDTTVVSPEFDLCQEYWEER......LNEYAPFSGNSLTGSTAP 445

VSAASPDIFQLSKVSPAQSTSMGSGEQVMGPKYEP..GDTSPHPENFRPD 496
:|||||||:|||||:||||| ||:||| |||| :|:|||||||||:|||
MSAASPDVFQLSKISPAQSPSLGSGEQAMEPAYEPGAGDTSSHPENLRPD 495

ALFSGNTADPSVFNNAIAMLLGNDLSIDCRPVLGDGIMFNSSSWSNMPHA 546
|:|||||||:|||||||||||||:::|:||||||||||| |:|||:|||
AFFSGNTADSSVFNNAIAMLLGNDMNTECKPVFGDGIMFDTSVWSNLPHA 545

CEMS.EFK 553
|:| |||
CQMSEEFK 553
```

FIGURE 12c

| | Control | $10^{-6}$ M GA$_3$ |
|---|---|---|
| mlo22 + Ubi.cass | 1.7 ± 0.7 | 100 ± 20.5 |
| mlo22 + Ubi.OsGAmyb | 299.6 ± 38.6 | 320.6 ± 68.6 |

FIGURE 14b

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 2220 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Hordeum vulgare
       (B) STRAIN: Himalaya
       (D) DEVELOPMENTAL STAGE: Seed
       (F) TISSUE TYPE: Aleurone layer (vii) IMMEDIATE SOURCE:
       (B) CLONE: HvGAMyb (ix) FEATURE:
       (A) NAME/KEY: CDS
       (B) LOCATION: 275..1933

(xi) SEQUENCE DESCRIPTION: SEQ ID NO:1:

```
CCCCCTCCCT CTCCCTCCTC CCTCAAAACT CTCTCTCCCT CCCTGAAAAT TCTCCGCATA      60

CTGGTGCCCA AGTGGTGCCG GCATCCCGCT GAGGGCAGAG AGAGAGAGAG AGAAAGAGAT     120

CCTCCTCCCC TGTCCCCACT CCCCTGATCC GCCGCCGAGC CGGGACGAGG AGGAGGAGGA     180

GCTGCAGCTC AGCTCCGCCC CAGCTCAGCC CCCGGAGCCC GAGCTGATCG ACCCGCCGGC     240

AGCGAGATTC GGCCAGGGCA CGATCGACGG AGAG ATG TAC CGG GTG AAG AGC         292
                                      Met Tyr Arg Val Lys Ser
                                        1               5

GAG AGC GAC TGC GAG ATG ATG CAC CAG GAG GAC CAG ATG GAC TCG CCG       340
Glu Ser Asp Cys Glu Met Met His Gln Glu Asp Gln Met Asp Ser Pro
            10                  15                  20

GTG GGC GAC GAC GGC AGC AGC GGC GGA GGG TCG CCT CAC AGG GGC GGC       388
Val Gly Asp Asp Gly Ser Ser Gly Gly Gly Ser Pro His Arg Gly Gly
        25                  30                  35

GGG CCG CCT CTG AAG AAG GGG CCC TGG ACG TCC GCG GAG GAC GCC ATC       436
Gly Pro Pro Leu Lys Lys Gly Pro Trp Thr Ser Ala Glu Asp Ala Ile
    40                  45                  50

CTG GTG GAC TAC GTG AAG AAG CAC GGC GAG GGG AAC TGG AAC GCG GTG       484
Leu Val Asp Tyr Val Lys Lys His Gly Glu Gly Asn Trp Asn Ala Val
55                  60                  65                  70

CAG AAG AAC ACC GGG CTG TTC CGG TGC GGC AAG AGC TGC CGC CTC CGG       532
Gln Lys Asn Thr Gly Leu Phe Arg Cys Gly Lys Ser Cys Arg Leu Arg
                75                  80                  85

TGG GCG AAC CAC CTC AGG CCC AAC CTC AAG AAG GGG GCC TTC ACC CCC       580
Trp Ala Asn His Leu Arg Pro Asn Leu Lys Lys Gly Ala Phe Thr Pro
            90                  95                 100

GAG GAG GAG AGG CTC ATC ATC CAG CTC CAC TCC AAG ATG GGC AAC AAG       628
Glu Glu Glu Arg Leu Ile Ile Gln Leu His Ser Lys Met Gly Asn Lys
        105                 110                 115

TGG GCT CGG ATG GCC GCT CAT TTG CCA GGG CGT ACT GAT AAT GAA ATA       676
Trp Ala Arg Met Ala Ala His Leu Pro Gly Arg Thr Asp Asn Glu Ile
    120                 125                 130

AAG AAT TAC TGG AAC ACT CGA ATA AAG AGA TGT CAG CGA GCC GGT TTG       724
Lys Asn Tyr Trp Asn Thr Arg Ile Lys Arg Cys Gln Arg Ala Gly Leu
```

-continued

| | | | | | | | | | | | | | | | | |
|---|---|---|---|---|---|---|---|---|---|---|---|---|---|---|---|---|
| | | 135 | | | | | 140 | | | | | 145 | | | | 150 |
| CCA | ATA | TAT | CCT | GCT | AGT | GTA | TGC | AAT | CAA | TCT | TCA | AAT | GAA | GAT | CAG | 772 |
| Pro | Ile | Tyr | Pro | Ala | Ser | Val | Cys | Asn | Gln | Ser | Ser | Asn | Glu | Asp | Gln | |
| | | | | 155 | | | | | 160 | | | | | 165 | | |
| CAG | GGC | TCC | AGC | GAT | TTC | AAC | TGC | GGC | GAG | AAT | CTT | TCC | AGT | GAC | CTC | 820 |
| Gln | Gly | Ser | Ser | Asp | Phe | Asn | Cys | Gly | Glu | Asn | Leu | Ser | Ser | Asp | Leu | |
| | | | 170 | | | | | 175 | | | | | 180 | | | |
| CTG | AAT | GGA | AAT | GGT | CTT | TAT | CTG | CCA | GAT | TTT | ACC | TGT | GAC | AAT | TTC | 868 |
| Leu | Asn | Gly | Asn | Gly | Leu | Tyr | Leu | Pro | Asp | Phe | Thr | Cys | Asp | Asn | Phe | |
| | | | 185 | | | | | 190 | | | | | 195 | | | |
| ATT | GCT | AAT | TCA | GAG | GCT | CTA | TCT | TAT | GCA | CCA | CAG | CTT | TCA | GCT | GTT | 916 |
| Ile | Ala | Asn | Ser | Glu | Ala | Leu | Ser | Tyr | Ala | Pro | Gln | Leu | Ser | Ala | Val | |
| | | | 200 | | | | | 205 | | | | | 210 | | | |
| TCA | ATA | AGC | AGT | TTG | CTT | GGC | CAG | AGC | TTT | GCA | TCC | AAA | AAC | TGC | GGC | 964 |
| Ser | Ile | Ser | Ser | Leu | Leu | Gly | Gln | Ser | Phe | Ala | Ser | Lys | Asn | Cys | Gly | |
| 215 | | | | | 220 | | | | | 225 | | | | | 230 | |
| TTC | ATG | GAT | CAA | GTA | AAC | CAA | GCA | GGG | ATG | CTA | AAA | CAG | TCT | GAC | CCT | 1012 |
| Phe | Met | Asp | Gln | Val | Asn | Gln | Ala | Gly | Met | Leu | Lys | Gln | Ser | Asp | Pro | |
| | | | | 235 | | | | | 240 | | | | | 245 | | |
| TTA | CTC | CCT | GGA | TTG | AGC | GAC | ACC | ATC | AAT | GGC | GCG | CTC | TCC | TCG | GTC | 1060 |
| Leu | Leu | Pro | Gly | Leu | Ser | Asp | Thr | Ile | Asn | Gly | Ala | Leu | Ser | Ser | Val | |
| | | | 250 | | | | | 255 | | | | | 260 | | | |
| GAT | CAA | TTC | TCA | AAT | GAC | TCT | GAG | AAG | CTC | AAG | CAG | GCT | CTT | GGT | TTT | 1108 |
| Asp | Gln | Phe | Ser | Asn | Asp | Ser | Glu | Lys | Leu | Lys | Gln | Ala | Leu | Gly | Phe | |
| | | 265 | | | | | 270 | | | | | 275 | | | | |
| GAC | TAT | CTC | CAC | GAA | GCC | AAC | TCT | AGC | AGC | AAG | ATT | ATT | GCA | CCA | TTT | 1156 |
| Asp | Tyr | Leu | His | Glu | Ala | Asn | Ser | Ser | Ser | Lys | Ile | Ile | Ala | Pro | Phe | |
| | | 280 | | | | | 285 | | | | | 290 | | | | |
| GGG | GGT | GCG | CTT | ACT | GGC | AGC | CAT | GCC | TTT | TTA | AAT | GGC | ACC | TTC | TCT | 1204 |
| Gly | Gly | Ala | Leu | Thr | Gly | Ser | His | Ala | Phe | Leu | Asn | Gly | Thr | Phe | Ser | |
| 295 | | | | | 300 | | | | | 305 | | | | | 310 | |
| ACT | TCT | AGG | ACC | ATC | AAT | GGT | CCT | TTG | AAG | ATG | GAG | CTC | CCT | TCA | CTC | 1252 |
| Thr | Ser | Arg | Thr | Ile | Asn | Gly | Pro | Leu | Lys | Met | Glu | Leu | Pro | Ser | Leu | |
| | | | | 315 | | | | | 320 | | | | | 325 | | |
| CAA | GAT | ACC | GAA | TCT | GAT | CCG | AAT | AGC | TGG | CTC | AAG | TAT | ACC | GTG | GCT | 1300 |
| Gln | Asp | Thr | Glu | Ser | Asp | Pro | Asn | Ser | Trp | Leu | Lys | Tyr | Thr | Val | Ala | |
| | | | 330 | | | | | 335 | | | | | 340 | | | |
| CCT | GCG | ATG | CAG | CCT | ACG | GAG | TTG | GTT | GAT | CCG | TAC | CTG | CAG | TCC | CCG | 1348 |
| Pro | Ala | Met | Gln | Pro | Thr | Glu | Leu | Val | Asp | Pro | Tyr | Leu | Gln | Ser | Pro | |
| | | | 345 | | | | | 350 | | | | | 355 | | | |
| ACA | GCA | ACT | CCG | TCA | GTG | AAA | TCG | GAG | TGT | GCT | TCG | CCG | AGG | AAC | AGC | 1396 |
| Thr | Ala | Thr | Pro | Ser | Val | Lys | Ser | Glu | Cys | Ala | Ser | Pro | Arg | Asn | Ser | |
| | | | 360 | | | | | 365 | | | | | 370 | | | |
| GGC | CTC | TTG | GAA | GAG | CTG | CTT | CAT | GAA | GCT | CAG | GGA | CTA | AGA | TCT | GGG | 1444 |
| Gly | Leu | Leu | Glu | Glu | Leu | Leu | His | Glu | Ala | Gln | Gly | Leu | Arg | Ser | Gly | |
| 375 | | | | | 380 | | | | | 385 | | | | | 390 | |
| AAG | AAT | CAG | CAG | CTC | TCC | GTG | AGA | AGT | TCA | AGT | TCC | TCT | GTC | AGC | ACG | 1492 |
| Lys | Asn | Gln | Gln | Leu | Ser | Val | Arg | Ser | Ser | Ser | Ser | Ser | Val | Ser | Thr | |
| | | | | 395 | | | | | 400 | | | | | 405 | | |
| CCG | TGT | GAT | ACC | ACG | GTG | GTT | AGC | CCG | GAG | TTT | GAT | CTC | TGT | CAG | GAA | 1540 |
| Pro | Cys | Asp | Thr | Thr | Val | Val | Ser | Pro | Glu | Phe | Asp | Leu | Cys | Gln | Glu | |
| | | | 410 | | | | | 415 | | | | | 420 | | | |
| TAT | TGG | GAA | GAA | CGT | CTG | AAT | GAA | TAT | GCC | CCA | TTC | AGT | GGC | AAT | TCA | 1588 |
| Tyr | Trp | Glu | Glu | Arg | Leu | Asn | Glu | Tyr | Ala | Pro | Phe | Ser | Gly | Asn | Ser | |
| | | | 425 | | | | | 430 | | | | | 435 | | | |
| CTC | ACT | GGA | TCC | ACC | GCT | CCT | ATG | AGT | GCT | GCG | TCG | CCT | GAT | GTT | TTT | 1636 |
| Leu | Thr | Gly | Ser | Thr | Ala | Pro | Met | Ser | Ala | Ala | Ser | Pro | Asp | Val | Phe | |
| | | | 440 | | | | | 445 | | | | | 450 | | | |
| CAG | CTC | TCC | AAA | ATT | TCT | CCT | GCA | CAA | AGC | CCT | TCA | CTG | GGA | TCT | GGA | 1684 |

```
Gln Leu Ser Lys Ile Ser Pro Ala Gln Ser Pro Ser Leu Gly Ser Gly
455                 460                 465                 470

GAG CAG GCA ATG GAG CCT GCA TAT GAG CCC GGG GCA GGG GAC ACT TCG    1732
Glu Gln Ala Met Glu Pro Ala Tyr Glu Pro Gly Ala Gly Asp Thr Ser
                475                 480                 485

TCT CAT CCT GAA AAC TTG AGG CCA GAC GCG TTC TTC TCC GGG AAC ACG    1780
Ser His Pro Glu Asn Leu Arg Pro Asp Ala Phe Phe Ser Gly Asn Thr
                490                 495                 500

GCC GAC TCG TCC GTC TTC AAC AAC GCC ATA GCC ATG CTC CTG GGC AAC    1828
Ala Asp Ser Ser Val Phe Asn Asn Ala Ile Ala Met Leu Leu Gly Asn
                505                 510                 515

GAC ATG AAC ACG GAG TGC AAG CCT GTT TTC GGC GAC GGT ATC ATG TTT    1876
Asp Met Asn Thr Glu Cys Lys Pro Val Phe Gly Asp Gly Ile Met Phe
520                 525                 530

GAT ACT TCG GTG TGG AGC AAC TTG CCT CAT GCT TGT CAA ATG TCG GAG    1924
Asp Thr Ser Val Trp Ser Asn Leu Pro His Ala Cys Gln Met Ser Glu
535                 540                 545                 550

GAA TTC AAA TGAGTTCCTC ACCGAACCTC CAGCGGAGTC GAAGGAGATT            1973
Glu Phe Lys

CTTGGTATCC CTCACCCTGA TTGTTTTGAG GAAAAATTCA GAGAAAGCCT CATCGATTGT  2033

ATACGCTGCT GCGTGCGTAC GCGGCTGCTA CCAGATGCGC TCTCCGTTCA ACTAAGCCCC  2093

TTTTCCCCAA TAAAGTTGGC GGAGATAAGC CGGTTATCTA TTTTTTGTTT GTTTGTTTCG  2153

AACTAGAGAA CCCTTTTTTG TCATCTCTGT GGCATTTATT TGAACAATGT AAGATCAGTT  2213

ACTGCTT                                                           2220

(2) INFORMATION FOR SEQ ID NO:2:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:2:

Met Tyr Arg Val Lys Ser Glu Ser Asp Cys Glu Met Met His Gln Glu
1               5                   10                  15

Asp Gln Met Asp Ser Pro Val Gly Asp Gly Ser Ser Gly Gly
            20                  25                  30

Ser Pro His Arg Gly Gly Pro Leu Lys Lys Gly Pro Trp Thr
        35                  40                  45

Ser Ala Glu Asp Ala Ile Leu Val Asp Tyr Val Lys Lys His Gly Glu
    50                  55                  60

Gly Asn Trp Asn Ala Val Gln Lys Asn Thr Gly Leu Phe Arg Cys Gly
65                  70                  75                  80

Lys Ser Cys Arg Leu Arg Trp Ala Asn His Leu Arg Pro Asn Leu Lys
                85                  90                  95

Lys Gly Ala Phe Thr Pro Glu Glu Arg Leu Ile Ile Gln Leu His
                100                 105                 110

Ser Lys Met Gly Asn Lys Trp Ala Arg Met Ala Ala His Leu Pro Gly
            115                 120                 125

Arg Thr Asp Asn Glu Ile Lys Asn Tyr Trp Asn Thr Arg Ile Lys Arg
        130                 135                 140

Cys Gln Arg Ala Gly Leu Pro Ile Tyr Pro Ala Ser Val Cys Asn Gln
145                 150                 155                 160

Ser Ser Asn Glu Asp Gln Gln Gly Ser Ser Asp Phe Asn Cys Gly Glu
```

```
                165                 170                 175
Asn Leu Ser Ser Asp Leu Leu Asn Gly Asn Gly Leu Tyr Leu Pro Asp
                180                 185                 190

Phe Thr Cys Asp Asn Phe Ile Ala Asn Ser Glu Ala Leu Ser Tyr Ala
            195                 200                 205

Pro Gln Leu Ser Ala Val Ser Ile Ser Ser Leu Leu Gly Gln Ser Phe
        210                 215                 220

Ala Ser Lys Asn Cys Gly Phe Met Asp Gln Val Asn Gln Ala Gly Met
225                 230                 235                 240

Leu Lys Gln Ser Asp Pro Leu Pro Gly Leu Ser Asp Thr Ile Asn
                245                 250                 255

Gly Ala Leu Ser Ser Val Asp Gln Phe Ser Asn Asp Ser Glu Lys Leu
            260                 265                 270

Lys Gln Ala Leu Gly Phe Asp Tyr Leu His Glu Ala Asn Ser Ser Ser
        275                 280                 285

Lys Ile Ile Ala Pro Phe Gly Gly Ala Leu Thr Gly Ser His Ala Phe
290                 295                 300

Leu Asn Gly Thr Phe Ser Thr Ser Arg Thr Ile Asn Gly Pro Leu Lys
305                 310                 315                 320

Met Glu Leu Pro Ser Leu Gln Asp Thr Glu Ser Asp Pro Asn Ser Trp
                325                 330                 335

Leu Lys Tyr Thr Val Ala Pro Ala Met Gln Pro Thr Glu Leu Val Asp
            340                 345                 350

Pro Tyr Leu Gln Ser Pro Thr Ala Thr Pro Ser Val Lys Ser Glu Cys
        355                 360                 365

Ala Ser Pro Arg Asn Ser Gly Leu Leu Glu Glu Leu Leu His Glu Ala
370                 375                 380

Gln Gly Leu Arg Ser Gly Lys Asn Gln Gln Leu Ser Val Arg Ser Ser
385                 390                 395                 400

Ser Ser Ser Val Ser Thr Pro Cys Asp Thr Thr Val Val Ser Pro Glu
                405                 410                 415

Phe Asp Leu Cys Gln Glu Tyr Trp Glu Glu Arg Leu Asn Glu Tyr Ala
            420                 425                 430

Pro Phe Ser Gly Asn Ser Leu Thr Gly Ser Thr Ala Pro Met Ser Ala
        435                 440                 445

Ala Ser Pro Asp Val Phe Gln Leu Ser Lys Ile Ser Pro Ala Gln Ser
450                 455                 460

Pro Ser Leu Gly Ser Gly Glu Gln Ala Met Glu Pro Ala Tyr Glu Pro
465                 470                 475                 480

Gly Ala Gly Asp Thr Ser Ser His Pro Glu Asn Leu Arg Pro Asp Ala
                485                 490                 495

Phe Phe Ser Gly Asn Thr Ala Asp Ser Ser Val Phe Asn Asn Ala Ile
            500                 505                 510

Ala Met Leu Leu Gly Asn Asp Met Asn Thr Glu Cys Lys Pro Val Phe
        515                 520                 525

Gly Asp Gly Ile Met Phe Asp Thr Ser Val Trp Ser Asn Leu Pro His
530                 535                 540

Ala Cys Gln Met Ser Glu Glu Phe Lys
545                 550
```

(2) INFORMATION FOR SEQ ID NO:3:

(i) SEQUENCE CHARACTERISTICS:
      (A) LENGTH: 2352 base pairs (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Oryza sativa (ix) FEATURE:
        (A) NAME/KEY: CDS
        (B) LOCATION: 396..2054

(xi) SEQUENCE DESCRIPTION: SEQ ID NO:3:

```
GGAAAAATGG GGTGCCCATG CGGCCCTGCC CAATAGCGTT GCTGTACCTT TCAGCTTTAT      60

AATCTCGCCC CTCGCGAGAG AGACTCCCCC CATCCTGCAG ACTCGCCCCA CTCTCTTGCT     120

CAGCTCCTCC TCTTCATCCA GTCCTCAAAA CTCTCTCTGA TCTCTCTCTC TTGCTGAAAA     180

TTCTCCGCAC ACTCCGGTGG GCTTAAGCGG TGGCGGCGTC TCGCCTGGGT GGGCGAGATC     240

CCTCTCTTGC TCGTCCGCAA GGTCGCTCCC CCTGCGAGTC CAATCTACTG ACGAGCTGGG     300

AGGAGCAAAG GAGGGGGCAA TTGGAGCTCC GCTCGGTTCC AATTCAGCCC CAATTTTGAG     360

CCCCCCGGCT GCGGGGTTCG GCCAGTTGAG ACGCC ATG TAT CGG GTG AAG AGC        413
                                       Met Tyr Arg Val Lys Ser
                                        1               5

GAG AGC GAC TGC GAG ATG ATC CAT CAG GAG CAG ATG GAC TCG CCG GTG       461
Glu Ser Asp Cys Glu Met Ile His Gln Glu Gln Met Asp Ser Pro Val
             10                  15                  20

GCC GAC GAC GGC AGC AGC GGG GGG TCG CCG CAC CGC GGC GGC GGG CCC       509
Ala Asp Asp Gly Ser Ser Gly Gly Ser Pro His Arg Gly Gly Gly Pro
         25                  30                  35

CCG CTG AAG AAG GGG CCA TGG ACG TCG GCG GAG GAC GCC ATC CTG GTG       557
Pro Leu Lys Lys Gly Pro Trp Thr Ser Ala Glu Asp Ala Ile Leu Val
     40                  45                  50

GAC TAC GTG AAG AAG CAC GGC GAG GGG AAC TGG AAC GCG GTG CAG AAG       605
Asp Tyr Val Lys Lys His Gly Glu Gly Asn Trp Asn Ala Val Gln Lys
 55                  60                  65                  70

AAC ACC GGG CTG TTC CGG TGC GGC AAG AGC TGC CGC CTC CGG TGG GCG       653
Asn Thr Gly Leu Phe Arg Cys Gly Lys Ser Cys Arg Leu Arg Trp Ala
                 75                  80                  85

AAC CAC CTG AGG CCC AAC CTC AAG AAG GGG GCC TTC ACC GCC GAG GAG       701
Asn His Leu Arg Pro Asn Leu Lys Lys Gly Ala Phe Thr Ala Glu Glu
             90                  95                 100

GAG AGG CTC ATC ATC CAG CTC CAC TCC AAG ATG GGG AAC AAG TGG GCT       749
Glu Arg Leu Ile Ile Gln Leu His Ser Lys Met Gly Asn Lys Trp Ala
        105                 110                 115

CGG ATG GCC GCT CAT TTG CCA GGG CGC ACT GAT AAT GAA ATA AAG AAT       797
Arg Met Ala Ala His Leu Pro Gly Arg Thr Asp Asn Glu Ile Lys Asn
    120                 125                 130

TAC TGG AAT ACT CGA ATA AAG AGA TGC CAG CGA GCT GGC CTA CCC ATC       845
Tyr Trp Asn Thr Arg Ile Lys Arg Cys Gln Arg Ala Gly Leu Pro Ile
135                 140                 145                 150

TAT CCT ACC AGC GTA TGC AAT CAA TCC TCA AAT GAA GAT CAG CAG TGC       893
Tyr Pro Thr Ser Val Cys Asn Gln Ser Ser Asn Glu Asp Gln Gln Cys
                155                 160                 165

TCC AGT GAT TTT GAC TGT GGC GAG AAT TTG TCA AAC GAT CTT CTG AAT       941
Ser Ser Asp Phe Asp Cys Gly Glu Asn Leu Ser Asn Asp Leu Leu Asn
            170                 175                 180

GCA AAT GGT CTT TAC CTA CCA GAT TTT ACC TGT GAC AAT TTC ATT GCT       989
Ala Asn Gly Leu Tyr Leu Pro Asp Phe Thr Cys Asp Asn Phe Ile Ala
        185                 190                 195
```

```
AAT TCA GAG GCT TTA CCT TAT GCA CCA CAT CTT TCA GCC GTT TCT ATA     1037
Asn Ser Glu Ala Leu Pro Tyr Ala Pro His Leu Ser Ala Val Ser Ile
    200                 205                 210

AGC AAT CTC CTT GGC CAG AGC TTT GCA TCA AAA AGC TGT AGC TTC ATG     1085
Ser Asn Leu Leu Gly Gln Ser Phe Ala Ser Lys Ser Cys Ser Phe Met
215                 220                 225                 230

GAT CAG GTA AAC CAG ACA GGG ATG CTA AAA CAG TCT GAT GGT GTG CTT     1133
Asp Gln Val Asn Gln Thr Gly Met Leu Lys Gln Ser Asp Gly Val Leu
                235                 240                 245

CCT GGA TTG AGC GAT ACC ATC AAC GGT GTG ATT TCC TCG GTG GAT CAA     1181
Pro Gly Leu Ser Asp Thr Ile Asn Gly Val Ile Ser Ser Val Asp Gln
        250                 255                 260

TTC TCA AAT GAC TCT GAG AAG CTC AAG CAG GCT GTG GGT TTT GAC TAT     1229
Phe Ser Asn Asp Ser Glu Lys Leu Lys Gln Ala Val Gly Phe Asp Tyr
            265                 270                 275

CTC CAT GAA GCC AAC TCT ACC AGC AAG ATT ATT GCA CCT TTC GGG GGT     1277
Leu His Glu Ala Asn Ser Thr Ser Lys Ile Ile Ala Pro Phe Gly Gly
                280                 285                 290

GCA CTT AAT GGC AGC CAT GCC TTT TTA AAT GGC AAT TTC TCT GCT TCT     1325
Ala Leu Asn Gly Ser His Ala Phe Leu Asn Gly Asn Phe Ser Ala Ser
295                 300                 305                 310

AGG CCC ACA AGT GGT CCT TTG AAG ATG GAG CTC CCT TCA CTC CAA GAT     1373
Arg Pro Thr Ser Gly Pro Leu Lys Met Glu Leu Pro Ser Leu Gln Asp
                315                 320                 325

ACT GAA TCT GAT CCA AAC AGC TGG CTC AAG TAC ACT GTA GCT CCT GCG     1421
Thr Glu Ser Asp Pro Asn Ser Trp Leu Lys Tyr Thr Val Ala Pro Ala
        330                 335                 340

TTG CAG CCT ACT GAG TTA GTT GAT CCC TAC CTG CAG TCT CCA GCA GCA     1469
Leu Gln Pro Thr Glu Leu Val Asp Pro Tyr Leu Gln Ser Pro Ala Ala
            345                 350                 355

ACC CCT TCA GTG AAA TCA GAG TGC GCG TCG CCA AGG AAT AGT GGC CTT     1517
Thr Pro Ser Val Lys Ser Glu Cys Ala Ser Pro Arg Asn Ser Gly Leu
                360                 365                 370

TTG GAA GAG TTG ATT CAT GAA GCT CAG ACC CTA AGA TCC GGG AAG AAC     1565
Leu Glu Glu Leu Ile His Glu Ala Gln Thr Leu Arg Ser Gly Lys Asn
375                 380                 385                 390

CAA CAG ACA TCT GTG ATA AGT TCT AGT TCT TCT GTC GGT ACG CCA TGT     1613
Gln Gln Thr Ser Val Ile Ser Ser Ser Ser Ser Val Gly Thr Pro Cys
                395                 400                 405

AAT ACT ACG GTT CTT AGC CCA GAG TTT GAT ATG TGT CAG GAA TAC TGG     1661
Asn Thr Thr Val Leu Ser Pro Glu Phe Asp Met Cys Gln Glu Tyr Trp
        410                 415                 420

GAA GAA CAA CAT CCT GGT CCA TTC CTC AAT GAC TGT GCT CCT TTC AGT     1709
Glu Glu Gln His Pro Gly Pro Phe Leu Asn Asp Cys Ala Pro Phe Ser
            425                 430                 435

GGC AAT TCA TTC ACT GAA TCC ACC CCT CCT GTT AGC GCT GCA TCG CCT     1757
Gly Asn Ser Phe Thr Glu Ser Thr Pro Pro Val Ser Ala Ala Ser Pro
                440                 445                 450

GAC ATC TTT CAG CTC TCC AAA GTT TCC CCA GCA CAA AGC ACT TCA ATG     1805
Asp Ile Phe Gln Leu Ser Lys Val Ser Pro Ala Gln Ser Thr Ser Met
455                 460                 465                 470

GGA TCT GGA GAG CAA GTA ATG GGG CCT AAA TAT GAA CCT GGG GAC ACT     1853
Gly Ser Gly Glu Gln Val Met Gly Pro Lys Tyr Glu Pro Gly Asp Thr
                475                 480                 485

TCA CCT CAT CCT GAA AAC TTC AGG CCA GAT GCA TTG TTT TCT GGG AAT     1901
Ser Pro His Pro Glu Asn Phe Arg Pro Asp Ala Leu Phe Ser Gly Asn
        490                 495                 500

ACA GCT GAT CCA TCA GTT TTC AAC AAT GCC ATA GCA ATG CTT CTG GGC     1949
Thr Ala Asp Pro Ser Val Phe Asn Asn Ala Ile Ala Met Leu Leu Gly
            505                 510                 515
```

```
AAT GAC TTG AGT ATC GAT TGC AGA CCT GTT CTT GGC GAC GGT ATC ATG     1997
Asn Asp Leu Ser Ile Asp Cys Arg Pro Val Leu Gly Asp Gly Ile Met
        520                 525                 530

TTC AAT TCT TCC TCG TGG AGC AAC ATG CCA CAC GCC TGT GAA ATG TCA     2045
Phe Asn Ser Ser Ser Trp Ser Asn Met Pro His Ala Cys Glu Met Ser
535                 540                 545                 550

GAA TTC AAA TGAATTCTGT ATTTGGTATT TGCCAGACGC TAAAGCAGAT             2094
Glu Phe Lys

TCTTGGTATC GTTCTTGCTC ATTGTTTGGA TCATAACTTG AGGAAGATCT CGTCGGTTGT   2154

AATTCTGCAT TGCTGACAGA GTCCTTGATG GCATGCAGGC ACTATCAGAT GTTCTCTTAT   2214

GCGACTAGCC CTTTTGTCCA ATAAAGTAGT GCATGGAGAT AAGCCGGTTA ATTATTGTTT   2274

TCTTTTTTGT ATTAGAGAAC CCTTTTTGTC ATCTCTATTG CCGGAATTCT GTTGGAAATT   2334

CGTCATGTTT GTTTGAAC                                                 2352
```

(2) INFORMATION FOR SEQ ID NO:4:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:4:

```
Met Tyr Arg Val Lys Ser Glu Ser Asp Cys Glu Met Ile His Gln Glu
 1               5                  10                  15

Gln Met Asp Ser Pro Val Ala Asp Asp Gly Ser Ser Gly Gly Ser Pro
             20                  25                  30

His Arg Gly Gly Gly Pro Pro Leu Lys Lys Gly Pro Trp Thr Ser Ala
         35                  40                  45

Glu Asp Ala Ile Leu Val Asp Tyr Val Lys His Gly Glu Gly Asn
     50                  55                  60

Trp Asn Ala Val Gln Lys Asn Thr Gly Leu Phe Arg Cys Gly Lys Ser
65                  70                  75                  80

Cys Arg Leu Arg Trp Ala Asn His Leu Arg Pro Asn Leu Lys Lys Gly
                 85                  90                  95

Ala Phe Thr Ala Glu Glu Glu Arg Leu Ile Ile Gln Leu His Ser Lys
            100                 105                 110

Met Gly Asn Lys Trp Ala Arg Met Ala Ala His Leu Pro Gly Arg Thr
        115                 120                 125

Asp Asn Glu Ile Lys Asn Tyr Trp Asn Thr Arg Ile Lys Arg Cys Gln
    130                 135                 140

Arg Ala Gly Leu Pro Ile Tyr Pro Thr Ser Val Cys Asn Gln Ser Ser
145                 150                 155                 160

Asn Glu Asp Gln Gln Cys Ser Ser Asp Phe Asp Cys Gly Glu Asn Leu
                165                 170                 175

Ser Asn Asp Leu Leu Asn Ala Asn Gly Leu Tyr Leu Pro Asp Phe Thr
            180                 185                 190

Cys Asp Asn Phe Ile Ala Asn Ser Glu Ala Leu Pro Tyr Ala Pro His
        195                 200                 205

Leu Ser Ala Val Ser Ile Ser Asn Leu Leu Gly Gln Ser Phe Ala Ser
    210                 215                 220

Lys Ser Cys Ser Phe Met Asp Gln Val Asn Gln Thr Gly Met Leu Lys
225                 230                 235                 240
```

-continued

```
Gln Ser Asp Gly Val Leu Pro Gly Leu Ser Asp Thr Ile Asn Gly Val
            245                 250                 255

Ile Ser Ser Val Asp Gln Phe Ser Asn Asp Ser Glu Lys Leu Lys Gln
            260                 265                 270

Ala Val Gly Phe Asp Tyr Leu His Glu Ala Asn Ser Thr Ser Lys Ile
            275                 280                 285

Ile Ala Pro Phe Gly Gly Ala Leu Asn Gly Ser His Ala Phe Leu Asn
            290                 295                 300

Gly Asn Phe Ser Ala Ser Arg Pro Thr Ser Gly Pro Leu Lys Met Glu
305                 310                 315                 320

Leu Pro Ser Leu Gln Asp Thr Glu Ser Asp Pro Asn Ser Trp Leu Lys
            325                 330                 335

Tyr Thr Val Ala Pro Ala Leu Gln Pro Thr Glu Leu Val Asp Pro Tyr
            340                 345                 350

Leu Gln Ser Pro Ala Ala Thr Pro Ser Val Lys Ser Glu Cys Ala Ser
            355                 360                 365

Pro Arg Asn Ser Gly Leu Leu Glu Glu Leu Ile His Glu Ala Gln Thr
            370                 375                 380

Leu Arg Ser Gly Lys Asn Gln Gln Thr Ser Val Ile Ser Ser Ser Ser
385                 390                 395                 400

Ser Val Gly Thr Pro Cys Asn Thr Thr Val Leu Ser Pro Glu Phe Asp
            405                 410                 415

Met Cys Gln Glu Tyr Trp Glu Glu Gln His Pro Gly Pro Phe Leu Asn
            420                 425                 430

Asp Cys Ala Pro Phe Ser Gly Asn Ser Phe Thr Glu Ser Thr Pro Pro
            435                 440                 445

Val Ser Ala Ala Ser Pro Asp Ile Phe Gln Leu Ser Lys Val Ser Pro
450                 455                 460

Ala Gln Ser Thr Ser Met Gly Ser Gly Glu Gln Val Met Gly Pro Lys
465                 470                 475                 480

Tyr Glu Pro Gly Asp Thr Ser Pro His Pro Glu Asn Phe Arg Pro Asp
            485                 490                 495

Ala Leu Phe Ser Gly Asn Thr Ala Asp Pro Ser Val Phe Asn Asn Ala
            500                 505                 510

Ile Ala Met Leu Leu Gly Asn Asp Leu Ser Ile Asp Cys Arg Pro Val
            515                 520                 525

Leu Gly Asp Gly Ile Met Phe Asn Ser Ser Ser Trp Ser Asn Met Pro
530                 535                 540

His Ala Cys Glu Met Ser Glu Phe Lys
545                 550
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:5:

```
Met Tyr Arg Val Lys Ser Glu Ser Asp Cys Glu Met Met His Cys
1               5                   10                  15
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:6:

Cys Gly Ala Gly Asp Thr Ser Ser His Pro Glu Asn Leu Arg Pro
1               5                   10                  15

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TGTTCTTCTG CACCGCGTTC                                           20

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GTGCTTCACG TACTCCAC                                             18

(2) INFORMATION FOR SEQ ID NO:9:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GCCTGCAGGT CGACTCTAGA GAATCGCCTT TTGAGCTCAC CGTACCGGCC GATGACAAAC    60

TCCGG                                                               65

(2) INFORMATION FOR SEQ ID NO:10:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GCCTGCAGGT CGACTCTAGA GAATCGCCTT TTGAGCTCAC CGTACCGGCC GATAACAGAC    60

TCCGG                                                               65

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GTGTGCTGCG CAGCATGCCG G                                              21

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGCCGATAAC AAACTCCGG                                                 19

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGCCGACTCG AGACTCCGG                                                 19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GGCCGATGAC AAACTCCGG                                                 19

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGCCGATAAC AGACTCCGG                                                 19

(2) INFORMATION FOR SEQ ID NO:16:

(i) SEQUENCE CHARACTERISTICS:
        (A) LENGTH: 19 base pairs
        (B) TYPE: nucleic acid -continued

```
        (C) STRANDEDNESS: single
        (D) TOPOLOGY: linear (ii) MOLECULE TYPE: DNA (xi) SEQUENCE DESCRIPTION: SEQ ID NO:16:

GGCCGATAAC AAGCTCCGG                                                19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGCCGATAAC AAAATCCGG                                                19
```

PLANT REGULATORY PROTEINS III

CROSS-REFERENCE TO RELATED APPLICATIONS

This application is a continuation of PCT application PCT/AU96/00383 which designated The United States and was filed Jun. 21, 1996. That application is incorporated herein by reference.

FIELD OF THE INVENTION

The present invention relates generally to genetic constructs useful in regulating the synthesis of malting enzymes in plants, such as the α-amylase enzyme. More particularly, the present invention relates to nucleic acid molecules encoding gibberellin-regulated MYB polypeptides, for example the barley and rice aleurone gibberellin-regulated MYB polypeptides, and transcriptionally modulating parts and/or immunologically interactive parts thereof.

Bibliographic details of the publications referred to by author in this specification are collected at the end of the description. Sequence identity numbers (SEQ ID NOs.) for the nucleotide and amino acid sequences referred to in the specification are defined after the bibliography.

Throughout the specification and the claims that follow, unless the context requires otherwise, the word "comprise", or variations such as "comprises" or "comprising" will be understood to imply the inclusion of a stated element or integer or group of elements or integers but not the exclusion of any other element or integer or group of elements or integers.

BACKGROUND OF THE INVENTION

Malting and brewing are multi-million dollar industries. The annual added-value on barley production alone was approximately US$3 billion, in the USA between 1983 and 1992. During the same period, the US brewing industry generated US$167 billion in total business activity. The economic benefits to be derived from increased productivity of the brewing industry worldwide are enormous. A major contributing factor to this increased productivity is the improvement of the input raw material, the barley crop, the quality of which is largely determined by its genetic profile.

The primary goal of barley improvement for use in the brewing industry is to expand the germplasm available to breeders, thereby making available elite cultivars which are higher yielding, disease resistant, and/or possess improved malting characteristics. Traditional plant breeding methods have made considerable progress toward these goals, however such processes are labour-intensive, imprecise and protracted, requiring several generations of genetic crosses to produce a substantially-improved genetic stock. The present invention is a significant advance in the improvement of malting characteristics of plant materials utilised in the brewing industry, in particular barley, wherein said invention provides a "master switch", controlling the expression of several malting genes, for example α-amylase and β-glucanase, amongst others.

During the malting process, the barley grain is water-steeped for 1–2 days at 10–20° C. to remove $CO_2$, replace oxygen and dissipate heat. The steeping process induces germination of the seed, characterised by cell elongation and increased respiration in the embryo, stimulation of embryo secretions, protein biosynthesis and enzyme activation, and the initiation of endosperm hydration. Kernel moisture content increases from 10–15% (w/w) to 40–45% (w/w) as a result of steeping (botanically-defined germination initiates at approximately 30% moisture content). Following steeping, the grains are germinated in a controlled growth environment for 3–6 days, producing a "green malt". Losses may be incurred at this stage, from incomplete or variable germination of the seed and consequently, there are many benefits to be derived from producing a crop in which seed dormancy could be broken uniformly and completely during steeping, providing rapid and uniform germination. Furthermore, dormancy of barley seed should also be adequate to prevent pre-harvest sprouting and consequential crop losses. Accordingly, the present invention provides a means of regulating the expression of the α-amylase gene in aleurone cells of the seed. The present invention may be used to control the germination of a crop seed.

During malting, the major constituent of the cell wall of the starchy endosperm of barley, β-glucan, is broken down by the enzyme (1-3, 1-4)-β-glucanase, referred to hereinafter as β-glucanase, which is secreted from the aleurone cells (Fincher, 1989). The efficient degradation of β-glucan polymers is important to the brewing process, since the presence of high molecular weight β-glucans increases the viscosity of the "mash", thereby slowing later filtration steps. Incomplete hydrolysis of β-glucan molecules may even produce a cloudy precipitate in the fished product. The degree of hydrolysis of β-glucan is a function of the level of β-glucanase enzyme produced by the aleurone and the proportion of enzyme activity remaining following higher temperature incubations of kilning and mashing (see below). There is a clear need in the malting industry for the production of barley lines with increased β-glucanase activity, to facilitate the malting process.

The green malt is dried in kilns to reduce kernel moisture to 3–5%. Malt components are subsequently converted into a fermentable substrate which includes sugars, amino acids, nucleic acids, vitamins and minerals. The malt is placed in warm water and taken through a series of controlled temperature rises and holds from 40° C. to 75° C., in order to gelatinise and solubilise seed starch reserves and to solubilise carbohydrate-degrading enzymes. The production of fermentable sugars for example maltose and glucose, requires the hydrolytic enzymes α-amylase, β-amylase, α-glucosidase and limit dextrinase. Of these enzymes, α-amylase, α-glucosidase and limit dextrinase are known to be secreted from the aleurone (Fincher, 1989).

Fermentable sugars are produced by α-amylase enzyme activity at 70–75° C. The survival of these hydrolytic enzymes, in particular α-amylase, during and after kilning, is critical to the brewing process and to the flavour and colour of the malt and the alcohol content of the finished product. The proportion of these enzymes remaining after kilning is directly proportional to the amount of enzyme in the germinating seed after dormancy is broken. Using technology available until the present invention, the efficiency of this process was improved by the addition of a microbial amyloglucosidase supplement to the mash, in particular in the production of some low calorie beers.

Although the development of a barley crop with improved malting characteristics, in particular possessing increased aleurone α-amylase, α-glucosidase, limit dextrinase, β-glucanase, endoxylanase and protease activities, is highly desirable, traditional breeding technologies have not addressed the problem, in part because reliable methods for screening large numbers of plants carrying these trials have not been developed.

The level of aleurone secretory enzymes, in particular α-amylase, β-glucanase, etc., may be increased by the application of the plant hormone, gibberellin acid (GA), in particular $GA_3$ (Paleg, 1960; Varner, 1964; Yomo, 1960). Following addition of GA, there is a rapid rise in α-amylase gene expression in isolated barley aleurone layers and this effect is inhibited by ascisic acid (Jacobsen et al., 1995).

Although there are now considerable data about the site of GA perception in aleurone cells, the GA receptor has not yet been identified. Evidence from experiments using $GA_4$ covalently bound to Sepharose beads and anti-idiotype antibodies suggests that GA is perceived on the plasma membrane in oat aleurone protoplasts (Hooley et al., 1991; Hooley et al., 1992). This is supported by recent work which shows micro injection of $GA_3$ into isolated barley aleurone protoplasts failed to induce α-amylase synthesis and secretion (Gilroy and Jones, 1994). However, when $GA_3$ was applied external to the medium, the protoplasts responded by increasing α-amylase gene expression, indicating that the site of perception is on the external face of the plasma membrane. Little is known of the molecular events downstream of the GA receptor which transmit the GA signal through the cytoplasm and ultimately trigger expression of genes encoding α-amylase and other hydrolytic enzymes (Bush and Jones, 1990; Gilroy and Jones 1992).

Functional analysis of barley high-pI α-amylase promoters have identified a gibberellin response complex (GARC) consisting of the pyrimidine, TAACAAA and TATCCAC boxes, which mediate the GA response (Skriver et al., 1991; Gubler and Jacobsen, 1992; Gubler et al., 1995). There is also evidence that the action of abscisic acid is mediated via the same complex. Analyses of a barley low-pI amylase promoter, have shown that GA probably also acts through similar cis-acting elements, but additional cis-acting elements upstream of the pyrimidine box are also important (Lanahan et al., 1992). DNA sequences that bind nuclear proteins in vitro have been identified in cereal α-amylase promoters using DNase 1 foot printing and gel mobility shift assays (Ou-Lee et al., 1988; Rushton et al., 1992; Sutliff et al., 1993; Goldman et al., 1994). Two recent studies have shown that GARC sequences in wheat and barley α-amylase promoters can act as binding sites for nuclear transcription factors which regulate gene expression. Sutliff et al. (1993) characterized nuclear factors from barley aleurone layers which bound in vitro, to sequences from a barley low-pI α-amylase gene. A GA-dependent binding factor was shown to bind specifically to sequences which coincide with the TAACAGA and TATCCAT boxes and proximal sequences. It is not yet clear whether this binding factor contains a single nuclear protein which binds to both elements or whether it consists of two or more proteins with different binding specificities. Rushton et al. (1992) demonstrated that nuclear factors from GA-treated oat protoplasts bound specifically to the box 2 and the pyrimidine and TAACAGA elements in a low-pI wheat α-amylase promoter. The function of these proteins in regulating α-amylase gene expression has not been determined. Furthermore, the demonstration of a DNA-protein interaction does not provide significant direction to enable a person normally skilled in the art to isolate the DNA-binding protein or a gene encoding said protein, or to determine the role of said protein in regulating the expression of genes encoding malting enzymes, for example α-amylase and β-glucanase, amongst others.

DETAILED DESCRIPTION OF THE INVENTION

One aspect of the present invention provides an isolated nucleic sequence which encodes, or is complementary to a sequence which encodes, a seed-specific gibberellin-regulated MYB polypeptide, seed-expressed gibberellin-regulated MYB polypeptide or other gibberellin-regulated MYB polypeptide.

Preferably, said MYB regulates the expression of gibberellin-regulated genes encoding hydrolytic enzymes involved in the malting process, for example high pI α-amylase, low pI α-amylase, EII-(1-3, 1-4)-β-glucanase, Cathepsin β-like proteases, α-glucosidase, xylanase, arabinofuranosidases, amongst others.

Preferably, the isolated nucleic acid molecule of the invention is cDNA, genomic DNA or mRNA. In a particularly preferred embodiment, the nucleic acid molecule is a cDNA molecule.

In a preferred embodiment of the invention, the isolated nucleic acid molecule of the invention is derived from a monocotyledonous plant species selected from the list comprising rice, barley, wheat, maize, rye and sorghum, amongst others. In a particularly preferred embodiment, the isolated nucleic acid molecule is derived from barley or rice.

The present invention extends to the isolated nucleic acid molecule when integrated into the genome of a cell as an addition to the endogenous cellular complement of gibberellin-regulated Myb genes. The said integrated nucleic acid molecule may, or may not, contain promoter sequences which confer gibberellin-regulated expression of the Myb genetic sequence contained therein.

Hereinafter the term "gibberellin-regulated MYB", or "GAMYB", or similar term shall refer to a polypeptide belonging to the class of MYB transcription factors, the synthesis and/or activity of which is normally regulated by gibberellins in the cells of plants, in particular in seeds or germinating seedlings, and which control the expression of genes involved in:

(i) plant developmental processes selected from the list comprising stem elongation, flowering, leaf development, fruit set and growth, sex determination, germination, amongst others; or (ii) malting characteristics selected from the list comprising seed dormancy, germination, post-kilning levels of hydrolytic enzymes, mash filtration properties, precipitate formation and alcohol content, amongst others, wherein said hydrolytic enzymes are selected from the list comprising GA-regulated hydrolases, in particular the high pI α-amylase, low pI α-amylase, EII-(1-3, 1-4)-β-glucanase and Cathepsin β-like proteolytic enzymes, amongst others.

A GAMYB as defined herein may further be regulated by other plant hormones, for example abscisic acid, amongst others.

Hereinafter the term "gibberellin-regulated Myb gene", "GAMyb" or similar term shall be used to define a gene which upon expression, encodes a polypeptide comprising an amino acid sequence having the activity of a gibberellin-regulated MYB polypeptide.

Reference herein to "genes" is to be taken in its broadest context and includes:

(I) a classical genomic gene consisting of transcriptional and/or translational regulatory sequences and/or a coding region and/or non-translated sequences (i.e. introns, 5'- and 3'- untranslated sequences); or (ii) mRNA or cDNA corresponding to the coding regions (i.e. exons) and 5'-and 3'- untranslated sequences of the gene.

The term "gene" is also used to describe synthetic or fusion molecules encoding all or part of a functional product. Preferred gibberellin-regulated Myb genes may be derived from a naturally-occurring gibberellin-regulated Myb gene by standard recombinant techniques. Generally, a gibberellin-regulated Myb gene may be subjected to mutagenesis to produce single or multiple nucleotide substitutions, deletions and/or additions. Nucleotide insertional derivatives of the gibberellin-regulated Myb gene of the present invention include 5' and 3' terminal fusions as well as intra-sequence insertions of single or multiple nucleotides. Insertional nucleotide sequence variants are those in whir one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

Another aspect of the present invention is directed to an isolated nucleic molecule which comprises a sequence of nucleotides corresponding, or complementary to the sequence set forth in SEQ ID NO: 1 or SEQ ID NO:3 or a homologue, analogue or derivative thereof, or having at least about 40%, more preferably at least about 55%, still more preferably at least about 65%, yet still more preferably at least about 75–80% and even still more preferably at least about 85–95% nucleotide similarity to all, or a part thereof, of SEQ ID NO: 1 or SEQ ID NO:3.

According to this aspect, said nucleic acid molecule encodes, or is complementary to a nucleotide sequence encoding, a plant gibberellin-regulated MYB polypeptide.

In a preferred embodiment, the nucleic acid molecule is derived from a monocotyledonous plant species selected from the list comprising rice, barley, wheat, maize, rye and sorghum. In a particularly preferred embodiment, the isolated nucleic acid molecule is derived from barley or rice.

For the purposes of nomenclature, the nucleotide sequence shown in SEQ ID NO: 1 relates to the barley GAMyb cDNA sequence (HvGAMyb), which is expressed in barley aleurone cells in response to exogenous application of gibberellin. Preferably, the polypeptide encoded therein regulates expression of a number of genes involved in the malting process, including α-amylases, in particular high pI α-amylases and low pI α-amylases, β-glucanases, in particular EII-(1-3, 1-4)-β-glucanase, proteases, in particular Cathepsin β-like proteases, α-glucosidases, xylanases, and arabinofuranosidases, amongst others. More preferably, the polypeptide encoded therein, regulates, at least the expression of the barley α-amylase gene, in aleurone cells.

The nucleotide sequence set forth in SEQ ID NO:3 relates to the rice homologue of the barley GAMyb cDNA sequence, designated hereinafter as "rice GAMyb" or "OsGAMyb". Details of the isolation and characterisation of the rice GAMyb cDNA clone are provided by the Examples incorporated herein.

For the present purpose, "homologues" of a nucleotide sequence shall be taken to refer to an isolated nucleic acid molecule which is functionally the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

A further aspect of the present invention provides an isolated nucleic molecule which is capable of hybridising under at least low stringency conditions to the nucleic acid molecule set forth in SEQ ID NO:1 or SEQ ID NO:3, or to a complementary strand or a homologue, analogue or derivative thereof.

Preferably, said nucleic acid molecule encodes, or is complementary to a nucleic acid molecule which encodes a plant gibberellin-regulated MYB polypeptide.

More preferably, the nucleic acid molecule encodes, or is complementary to a nucleic acid molecule which encodes, a gibberellin-regulated MYB polypeptide and which is capable of hybridising under at least low stringency conditions to all, or a part thereof, nucleotide residues 1 to 400 or residues 710 to 2220, of the nucleic acid molecule set forth in SEQ ID NO: 1, or to a complementary strand or a homologue, analogue or derivative thereof.

In a particularly preferred embodiment, said nucleic acid molecule does not encode solely, or is not complementary to a nucleic acid molecule which encodes solely, the conserved R2 and R3 domains of a MYB polypeptide of plant origin or a part thereof, or does not hybridise exclusively under low stringency conditions to nucleotide residues 401 to 709, of the nucleic acid molecule set forth in SEQ ID NO: 1 encoding same, or to a complementary strand thereof.

In an alternative preferred embodiment, the nucleic acid molecule encodes, or is complementary to a nucleic acid molecule which encodes, a gibberellin-regulated MYB polypeptide and which is capable of hybridising under at least low stringency conditions to all, or a part thereof, nucleotide residues 1 to 671 or residues 816 to 2352 of the nucleic acid molecule set forth in SEQ ID NO:3, or to a complementary strand or a homologue, analogue or derivative thereof, which do not encode, or are not complementary to a nucleic acid molecule which encodes the conserved R2 and R3 domains of a MYB polypeptide.

Accordingly, the isolated nucleic acid molecule according to this preferred embodiment does not hybridise exclusively under low stringency conditions to nucleotide residues 672 to 815 of the nucleic acid molecule set forth in SEQ ID NO: 3 or to a complementary strand thereof.

For the purposes of defining the level of stringency, a low stringency is defined herein as being a hybridisation and/or a wash carried out in 6xSSC buffer, 0.1% (w/v) SDS at a temperature in the range 28° C.–55° C. Generally, the stringency is increased by reducing the concentration of SSC buffer, and/or increasing the concentration of SDS and/or increasing the temperature of the hybridisation and/or wash. Conditions for hybridisations and washes are well understood by one normally skilled in the art. For the purposes of clarification, of the parameters affecting hybridisation between nucleic acid molecules, reference is found in pages 2.10.8 to 2.10.16. of Ausubel et al. (1987), which is herein incorporated by reference.

The present invention is particularly directed to a gibberellin-regulated Myb gene, such as the barley GAMyb or rice GAMyb. The subject invention clearly contemplates other sources of gibberellin-regulated Myb genes, or gibberellin-regulated Myb-like genes, such as but not limited to, aleurone or embryo tissues and cultured cells of plant origin, derived from, but not limited to, other plant species including, wheat, maize, rye, or sorghum. Preferably, said Myb gene, or Myb-like gene, is involved in the transcriptional modulation of genes involved in biological processes selected from the list comprising, but not limited to, stem elongation, flowering, leaf development, fruit set and growth, sex determination, germination or malting characteristics as hereinbefore defined.

The present invention clearly contemplates a genomic clone equivalent of the nucleotide sequence set forth in SEQ ID NO: 1 or SEQ ID NO:3 and extends to a promoter or functional derivative, part fragment, homologue or analogue thereof from a genomic clone equivalent of the nucleotide sequence defined by SEQ ID NO: 1 or SEQ ID NO:3.

The genetic sequences which encode, or are complementary to genetic sequences which encode, a gibberellin-regulated MYB polypeptide or gibberellin-regulated MYB-like polypeptide, may correspond to the naturally occurring sequence or may differ by one or more nucleotide substitutions, deletions and/or additions. Accordingly, the present invention extends to gibberellin-regulated Myb and Myb-like genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules.

In a particularly preferred embodiment, the gibberellin-regulated Myb genetic sequences disclosed herein are employed to identify and isolate similar genes from other barley or rice cells, tissues, or organ types, or from the cells, tissues, or organs of other plant species.

According to this embodiment, there is contemplated a method for identifying a related gibberellin-regulated Myb genetic sequence, or gibberellin-regulated Myb-like genetic sequence, said method comprising contacting genomic DNA, or mRNA, or cDNA with a hybridisation effective amount of a gibberellin-regulated Myb genetic sequence, or a functional part, homologue, analogue or derivative thereof, and then detecting said hybridisation.

The related genetic sequence may be in a recombinant form, in a virus particle, bacteriophage particle, yeast cell, animal cell, or a plant cell. Preferably, the related genetic sequence originates from a plant species other than the species from which the gibberellin-regulated Myb genetic sequence was derived. More preferably, the related genetic sequence originates from a plant used in the malting process, for example the monocotyledonous plants wheat, rye, maize, rice or sorghum, amongst others. In a particularly preferred embodiment the related genetic sequences are derived from rice.

Preferably, the gibberellin-regulated Myb genetic sequence (i.e latter genetic sequence) is from a monocotyledonous plant species. In a most preferred embodiment, the latter genetic sequence is as set forth in SEQ ID NO: 1 or SEQ ID NO:3.

Preferably, the latter genetic sequence is labelled with a reporter molecule capable of giving an identifiable signal (e.g. a radioisotope such as $^{32}P$ or $^{35}S$ or a biotinylated molecule).

An alternative method contemplated in the present invention involves hybridising two nucleic acid "primer molecules" of at least 15 nucleotides in length to a nucleic acid "template molecule", said template molecule herein defined as a related gibberellin-regulated Myb genetic sequence, or a functional part thereof, or its complementary sequence. Specific nucleic acid molecule copies of the template molecule are amplified enzymatically in a polymerase chain reaction, a technique that is well known to one skilled in the art.

Preferably, the nucleic acid primer molecules are contained in an aqueous mixture of other nucleic acid primer molecules. More preferably, the nucleic acid primer molecule is in a substantially pure form. In a preferred embodiment, each nucleic acid primer molecule is any nucleotide sequence of at least 15 nucleotides in length derived from, or complementary to the nucleotide sequence set forth in SEQ ID NO: 1 or SEQ ID NO:3, or a homologue, analogue or derivative thereof.

In a particularly preferred embodiment, at least one primer molecule is substantially the same as, or complementary to, nucleotide sequences comprising at least 15 nucleotides in length, of the sequences set forth in residues 1 to 400, or 710 to 2220 of SEQ ID NO: 1 or alternatively, nucleotide residues 1 to 671 or 816 to 2352 of SEQ ID NO:3, which do not encode highly conserved R2 or R3 amino acid sequence motifs found in MYB polypeptides. According to this embodiment, the nucleic acid primer molecule consists of a combination of any of the nucleotides adenine, cytidine, guanine, thymidine, or inosine, or functional analogues or derivatives thereof, capable of being incorporated into a polynucleotide molecule.

The nucleic acid template molecule may be in a recombinant form, in a virus particle, bacteriophage particle, yeast cell, animal cell, or a plant cell. Preferably, the related genetic sequence originates from a mammalian cell, tissue, or organ. More preferably, the related genetic sequence originates from a plant cell, tissue or organ.

Yet another aspect of the present invention provides for the expression of the subject genetic sequence in a suitable host (e.g. a prokaryote or eukaryote) to produce full length or non-full length recombinant gibberellin-regulated MYB gene products. Preferably, the gibberellin-regulated MYB gene product has a sequence that is identical to, or contained within the amino acid sequence set forth in SEQ ID NO:2 or SEQ ID NO:4.

For the purposes of nomenclature, the amino acid sequences set forth in SEQ ID Nos:2 and 4 relate to the barley and rice GAMYB polypeptides, respectively.

In an alternative embodiment, the present invention provides an isolated polypeptide which comprises an amino acid sequence having the transcriptional activation function of a gibberellin-regulated MYB, or a functional homologue, mutant, derivative, part, fragment, or analogue of said polypeptide.

Preferably, the polypeptide is the polypeptide product of the barley or rice GAMyb gene sequence.

In the present context, "homologues" of an amino acid sequence refer to those polypeptides, enzymes or proteins which have a similar catalytic activity to the amino acid sequences set forth in SEQ ID NO:2 or SEQ ID NO:4, notwithstanding any amino acid substitutions, additions or deletions thereto. A homologue may be isolated or derived from the same or another plant species as the species from which the polypeptides of the invention are derived.

Furthermore, the amino acids of a homologous polypeptide may be replaced by other amino acids having similar properties, for example hydrophobicity, hydrophilicity, hydrophobic moment or antigenicity, and so on.

"Analogues" encompass polypeptides of the invention notwithstanding the occurrence of any non-naturally occurring amino acid analogues therein.

The term "derivative" in relation to a GAMYB polypeptide shall be taken to refer hereinafter to mutants, parts or fragments of the complete barley or rice GAMYB polypeptides defined herein. Derivatives include modified peptides in which ligands are attached to one or more of the amino acid residues contained therein, such as carbohydrates, enzymes, proteins, polypeptides or reporter molecules such as radionucleotides or fluorescent compounds. Glycosylated, fluorescent, acylated or alkylated forms of the subject peptides are particularly contemplated by the present invention. Additionally, derivatives of SEQ ID NO:2 or SEQ ID NO:4 which comprise fragments parts of the subject amino acid sequences are within the scope of the invention, as are homopolymers or heteropolymers comprising two or more copies of the subject polypeptides. Procedures for derivatizing peptides are well-known in the art.

Substitutions encompass amino acid alterations in which an amino acid is replaced with a different naturally-occurring or a non-conventional amino acid residue. Such substitutions may be classified as "conservative", in which an amino acid residue contained in a cellulose gene product is replaced with another naturally-occurring amino acid of similar character, for example Gly←→Ala, Val←→Ile←→Leu, Asp←→Glu, Lys←→Arg, Asn←→Gln or Phe←→Trp←→Tyr.

Substitutions encompassed by the present invention may also be "non-conservative", in which an amino acid residue which is present in a cellulose gene product described herein is substituted with an amino acid with different properties, such as a naturally-occurring amino acid from a different group (eg. substituted a charged or hydrophobic amino acid with alanine), or alternatively, in which a naturally-occurring amino acid is substituted with a non-conventional amino acid. Non-conventional amino acids encompassed by the invention include, but are not limited to those listed in Table 2.

Amino acid substitutions are typically of single residues, but may be of multiple residues, either clustered or dispersed.

Amino acid deletions will usually be of the order of about 1–10 amino acid residues, while insertions may be of any length. Deletions and insertions may be made to the N-terminus, the C-terminus or be internal deletions or insertions. Generally, insertions within the amino acid sequence will be smaller than amino-o; carboxyl-terminal fusions and of the order of 1–4 amino acid residues.

The present invention extends to a gibberellin-regulated Myb gene characterised by said gene encoding a gibberellin-regulated MYB polypeptide having at least two similar amino acid repeat regions comprising 2 to 3 conserved tryptophan residues spaced 18 to 19 residues apart in each repeat region, hereinafter defined as structural features designated "R2" and "R3". While not wishing to be bound by any theory or mode of action, the conserved tryptophan residues may play a critical role in stabilising the DNA-binding domain of MYB transcription factors (Ogata et al., 1992).

Although the R2 and R3 motifs are conserved in MYB-related proteins, they provide no indication of the role of a particular MYB polypeptide in a cell and, since MYB-related proteins are numerous, it is not a straightforward procedure to use these high-conserved motifs to isolate a specific MYB-related polypeptide, or cDNA clone encoding same, which is involved in the transcriptional activation of a known gene; for example α-amylase.

The present invention extends further to a gibberellin-regulated Myb gene encoding a polypeptide which contains conserved R2 and R3 domains having at least approximately 85% identity to the R2 and R3 domains of HvGAMyb or OsGAMyb, with very low sequence identity outside these regions. Such GAMYB polypeptides bind to the same GA-response element, TAACAAA box or TAACAAA-like box to which barley and rice GAMYB polypeptides bind.

Preferably, the R2 and R3 structural features are adjacent and located at, or near, the N-terminal end of a GAMYB polypeptide and have at least 85% similarity to amino acid residues 42 to 145 of the amino acid sequence set forth in SEQ ID NO: 2 or to amino acid residues 93 to 143 of SEQ ID NO:4. More preferably, the R2 and R3 regions are substantially the same as amino acid residues 42 to 145, of the amino acid sequence set forth in SEQ ID NO: 2 or amino acid residues 93 to 143 of SEQ ID NO:4.

In a related embodiment, the present invention provides an isolated polypeptide which:

(I) contains structural features R2 and R3 of a gibberellin-regulated MYB polypeptide; and (ii) has at least 40% amino acid sequence similarity to the sequence set forth in SEQ ID NO:2 or SEQ ID NO:4 other than the R2 or R3 domains, or a homologue, analogue, derivative or part thereof.

Preferably, the percentage amino acid similarity is at least 60%, more preferably at least 80% and even more preferably at least 90%, including 91%, 93% or 95%.

In a particularly preferred embodiment, the present invention provides an isolated polypeptide which:

(I) contains structural features R2 and R3 of a gibberellin-regulated MYB polypeptide, wherein said features comprise an amino acid sequence which is at least 85% identical to amino acid residues 42 to 145 of SEQ ID NO: 2 or residues 93 to 143 of SEQ ID NO:4 ; and (ii) has at least 75% amino acid sequence similarity to the sequence set forth in SEQ ID NO:2 or SEQ ID NO:4 other than said features, or a homologue, analogue, derivative or part thereof.

In a related embodiment, the present invention provides a "sequencably pure" form of the amino acid sequence set forth in SEQ ID NO:2 or SEQ ID NO:4. "Sequencably pure" is hereinbefore described as substantially homogeneous to facilitate amino acid determination. In a further related embodiment, the present invention provides a "substantially homogeneous" form of the amino acid sequence set forth in SEQ ID NO:2 or SEQ ID NO:4, wherein the term "substantially homogeneous" is hereinbefore defined as being in a form suitable for interaction with an immunologically interactive molecule. Preferably, the polypeptide is at least 20% homogeneous, more preferably at least 50% homogeneous, still more preferably at least 75% homogeneous and yet still more preferably at least about 95–100% homogenous, in terms of activity per microgram of total protein in the protein preparation.

The present invention also extends to a synthetic peptide comprising any part of the amino acid sequence set forth in SEQ ID NO:2 or SEQ ID NO:4, or having at least 40% similarity to all or a part thereof, wherein the amino acid sequence set forth in SEQ ID NO:2 or SEQ ID NO:4 is a gibberellin-regulated MYB polypeptide.

In a particularly preferred embodiment, the invention provides a synthetic peptide comprising amino acid residues 1 to 14 of SEQ ID NO:2 or amino acid residues 481 to 494 of SEQ ID NO:2 or a homologue, analogue or derivative thereof.

In a related embodiment, the invention provides a synthetic peptide comprising the amino acid sequence:

(I) MYRVKSESDCEMMHC (SEQ ID NO:5); or (ii) CGAGDTSSHPENLRP (SEQ ID NO:6), or a homologue, analogue or derivative thereof.

The recombinant gibberellin-regulated MYB gene product, or part fragment, functional derivative, synthetic peptide, or 3-dimensional structure thereof, is used to produce immunologically interactive molecules, such as antibodies, or functional derivatives thereof, for example Fabs, SCABS (single-chain antibodies), or antibodies conjugated to an enzyme, radioactive or fluorescent tag, the only requirement being that the recombinant products are immunologically interactive with antibodies to all, or part, or a gibberellin-regulated MYB gene product.

According to this aspect, the present invention provides an antibody that binds to a polypeptide comprising an amino acid sequence which:

(I) has the transcriptional activation function of a gibberellin-regulated MYB, or a functional mutant, derivative, part, fragment, or analogue of said polypeptide; and (ii) is substantially the same as the amino acid sequence set forth in SEQ ID NO:2 or SEQ ID NO:4, or has at least 40% similarity to all or a part thereof.

In a particularly preferred embodiment, antibodies are raised against a synthetic peptide as hereinbefore defined and are capable of binding to the amino acid sequence:

(I) MYRVKSESDCEMMHC (SEQ ID NO:5); or (ii) CGAGDTSSHPENLRP (SEQ ID NO:6), or a homologue, analogue or derivative thereof.

Antibodies to a recombinant gibberellin-regulated MYB polypeptide are particularly useful in screening to isolate related gibberellin-regulated Myb genetic sequences and gibberellin-regulated Myb-like genetic sequences. The only requirements for successful detection of a related gibberellin-regulated Myb genetic sequence, or gibberellin-regulated Myb-like genetic sequence are that the said genetic sequence is expressed to produce a polypeptide, wherein said polypeptide contains at least one epitope recognised by an antibody molecule that binds to a gibberellin-regulated MYB polypeptide.

Preferably, for the purpose of obtaining expression to facilitate detection, the related gibberellin-regulated Myb genetic sequence, or gibberellin-regulated Myb-like genetic sequence is placed operably behind a promoter sequence, for example the bacterial lac promoter. According to this preferred embodiment, the antibodies that bind to a gibberellin-regulated MYB polypeptide are employed to detect the presence of a plasmid or bacteriophage which is capable of expressing said related gibberellin-regulated Myb genetic sequence, or gibberellin-regulated-Myb-like genetic sequence and are therefore useful in purifying the same.

Such antibodies may be monoclonal or polyclonal and may be selected from naturally occurring antibodies to an epitope, or peptide fragment, or synthetic peptide of a gibberellin-regulated MYB gene product or may be specifically raised against a recombinant gibberellin-regulated MYB gene product. Both polyclonal and monoclonal antibodies are obtainable by immunisation with an appropriate gene product, or epitope, or peptide fragment of a gene product. Alternatively, fragments of antibodies may be used, such as Fab fragments. Furthermore, the present invention extends to recombinant and synthetic antibodies and to antibody hybrids. A "synthetic antibody" is considered herein to include fragments and hybrids of antibodies.

The nucleic acid molecule of the present invention is also useful for developing genetic constructs which express a gibberellin-regulated Myb genetic sequence, thereby providing for the increased expression of genes encoding hydrolytic malting enzymes, such as, but not limited to, $\alpha$-amylase, $\beta$-glucanases such as EII-(1-3, 1-4)-$\beta$-glucanase, proteases such as Cathepsin $\beta$-like protease, $\alpha$-glucosidase, xylanase, arabinofuranosidase, amongst others.

According to this embodiment, the coding region of a gibberellin-regulated Myb gene is placed operably behind a promoter, in the sense orientation, such that a MYB polypeptide is capable of being expressed under the control of said promoter sequence.

In a particularly preferred embodiment, the gibberellin-regulated Myb genetic sequence is the barley GAMyb genetic sequence set forth in SEQ ID NO: 1 or the rice GAMyb genetic sequence set forth in SEQ ID NO: 3.

The nucleic acid molecule of the present invention is also useful for developing genetic constructs employing antisense or ribozyme molecules, or in co-suppression of the gibberellin-regulated Myb gene, in particular the barley or rice GAMyb genes. By targeting the endogenous gibberellin-regulated Myb gene, expression is diminished, reduced or otherwise lowered to a level that results in reduced expression of malting enzymes, in particular $\alpha$-amylase.

Preferably, the reduced expression of the GAMyb genetic sequence also reduces expression of genes encoding other malting enzymes, for example $\alpha$-amylases such as high pI and low pI $\alpha$-amylases, $\beta$-glucanase such as EII-(1-3, 1-4)-$\beta$-glucanase, proteases such as Cathepsin $\beta$-like protease, $\alpha$-glucosidase, xylanase, arabinofuranosidase, amongst others.

Co-suppression is the reduction in expression of an endogenous gene that occurs when one or more copies of said gene, or one or more copies of a substantially similar gene are introduced into the cell. The present invention also extends to the use of co-suppression to inhibit the expression of a gene which encodes a gibberellin-regulated MYB polypeptide.

Preferably, the gene which is targeted by a co-suppression molecule, is the barley GAMyb gene comprising the sequence of nucleotides set forth in SEQ ID NO: 1 or the rice GAMyb gene comprising the sequence of nucleotides set forth in SEQ ID NO: 3.

In the context of the present invention, an antisense molecule is an RNA molecule which is transcribed from the complementary strand of a nuclear gene to that which is normally transcribed to produce a "sense" mRNA molecule capable of being translated into a MYB polypeptide. The antisense molecule is therefore complementary to the sense mRNA, or a part thereof. Although not limiting the mode of action of the antisense molecules of the present invention to any specific mechanism, the antisense RNA molecule possesses the capacity to form a double-stranded mRNA by base pairing with the sense mRNA, which may prevent, delay or otherwise reduce translation of the sense MRNA and subsequent synthesis of a polypeptide gene product. Preferably, the antisense molecule of the present invention targets a barley or rice GAMyb mRNA molecule as hereinbefore defined.

In a particularly preferred embodiment, the present invention provides an antisense molecule comprising the 3' end of OsGAMyb cDNA sequence set forth in SEQ ID NO:3 or a complementary stand, homologue, analogue or derivative thereof which is useful in reducing the expression of a GAMyb gene in a monocotyledonous plant species selected from the list comprising barley, wheat, rye, rice, maize or sorghum, amongst others. In a most preferred embodiment, the antisense molecule is capable of reducing expression of the OsGAMyb gene (i.e. the rice GAMyb gene) in transgenic rice plants expressing the antisense molecule.

Preferably, the reduction in expression of the GAMyb gene is at least 10%, more preferably at least 20%, even more preferably at least 50% and even still more preferably at least 75% and yet even still more preferably at least 90%, compared to the expression of the gene in isogenic non-transformed plants or other plants belonging to the same species.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense MRNA. A complete description of the function of ribozymes is presented by Haseloff and Gerlach (1988) and contained in International Patent Application No. WO89/05852. The present invention extends to ribozyme which target a sense mRNA encoding a gibberellin-regulated MYB polypeptide, thereby hybridising to said sense mRNA and cleaving it, such that it is no longer capable of being translated to synthesise a functional polypeptide product. Preferably, the ribozyme molecule of the present invention targets a barley GAMyb mRNA molecule.

According to this embodiment, the present invention provides a ribozyme or antisense molecule comprising at least S contiguous nucleotide bases which are able to form a hydrogen-bonded complex with a sense mRNA encoding a gibberellin-regulated MYB polypeptide, to reduce translation of said mRNA. Although the preferred antisense and/or ribozyme molecules hybridise to at least about 10 to 20 nucleotides of the target molecule, the present invention extends to molecules capable of hybridising to at least about 50–100 nucleotide bases in length, or a molecule capable of hybridising to a full-length or substantially full-length gibberellin-regulated Myb mRNA.

In a particularly preferred embodiment, the antisense molecule is capable of hybridising to approximately 1000–1500 nucleotides of the target MRNA molecule.

It is understood in the art that certain modifications, including nucleotide substitutions amongst others, may be made to the antisense and/or ribozyme molecules of the present invention, without destroying the efficacy of said molecules in inhibiting the expression of a gene encoding a gibberellin-regulated MYB polypeptide. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridising to the said sense mRNA molecule.

Gene targeting is the replacement of an endogenous gene sequence within a cell by a related DNA sequence to which it hybridises, thereby altering the form and/or function of the endogenous gene and the subsequent phenotype of the cell. According to this embodiment, at least a part of the DNA sequence defined by SEQ ID NO: 1 or SEQ ID NO:3, or a related gibberellin-regulated Myb genetic sequence, may be introduced into target cells containing an endogenous gibberellin-regulated Myb gene to replace said genetic sequence, thereby altering said gibberellin-regulated Myb gene.

Furthermore, the polypeptide product of said gibberellin-regulated Myb genetic sequence possesses different DNA binding affinity/specificity and/or transcriptional activating activity and/or expression characteristics, producing in turn modified expression of genes regulated by said polypeptide, preferably genes involved in the malting process(es), for example α-amylase in particular high pI α-amylase and low pI α-amylase, β-glucanase in particular EII-(1-3, 1-4)-β-glucanase, proteases in particular Cathepsin β-like proteases, α-glucosidase, xylanase, arabinofuranosidase, amongst others.

The present invention extends to genetic constructs designed to facilitate expression of a gibberellin-regulated Myb genetic sequence which is identical, or complementary to the sequence set forth in SEQ ID NO: 1 or SEQ ID NO:3, or a functional derivative, part, homologue, or analogue thereof, or a genetic construct designed to facilitate expression of a sense molecule, an antisense molecule, ribozyme molecule, cosuppression molecule, or gene targeting molecule containing said genetic sequence.

The said genetic construct of the present invention comprises the foregoing sense, antisense, or ribozyme, or co-suppression nucleic acid molecule, or gene-targeting molecule encoding or complementary to a nucleic acid molecule encoding, a gibberellin-regulated MYB polypeptide, placed operably under the control of a promoter sequence capable of regulating the expression of the said nucleic acid molecule in a eukaryotic cell, preferably a plant cell. The said genetic construct optionally comprises, in addition to a promoter and sense, or antisense, or ribozyme, or co-suppression, or gene-targeting nucleic acid molecule, a terminator sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants. Examples of terminators particularly suitable for use in the genetic constructs of the present invention include the nopaline synthase (NOS) gene terminator of *Agrobacterium tumefaciens,* the terminator of the Cauliflower mosaic virus (CAMV) 35S gene, and the zein gene terminator from *Zea mays.*

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5′, of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of said antisense, or ribozyme, or co-suppression nucleic acid molecule, in a plant cell. Preferred promoters may contain additional copies of one or more specific regulatory elements, to further enhance expression of the antisense or ribozyme or co-suppression molecule and/or to alter the spatial expression and/or temporal expression of said sense or antisense, or ribozyme, or co-suppression, or gene-targeting molecule. For example, regulatory elements which confer copper inducibility may be placed adjacent to a heterologous promoter sequence driving expression of a sense, or antisense, or ribozyme, or co-suppression, or gene-targeting molecule, thereby conferring copper inducibility on the expression of said molecule.

Placing a sense or ribozyme, or antisense, or co-suppression, or gene-targeting molecule under the regulatory control of a promoter sequence means positioning the said molecule such that expression is controlled by the promoter sequence. Promoters are generally positioned 5′ (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include viral, fungal, bacterial, animal and plant derived promoters capable of functioning in plant cells. The promoter may regulate the expression of the said molecule constitutively, or differentially with respect to the tissue in which expression occurs or, with respect to the developmental stage at which expression occurs, or in response to external stimuli such as physiological stresses, or plant pathogens, or metal ions, amongst others. Preferably, the promoter is capable of regulating expression of a sense, or ribozyme, or antisense, or co-suppression molecule or gene targeting, in a plant cell. Examples of preferred promoters include the CaMV 35S promoter, NOS promoter, octopine synthase (OCS) promoter rice ActinI gene promoter and the like. The promoter may also be derived from a genomic clone encoding a gibberellin-regulated MYB polypeptide, preferably the barley or rice GAMyb genes.

In a most preferred embodiment, however, the promoter is capable of expression in a monocotyledonous plant cell, for example maize, wheat, barley, rice, sorghum, barley and rye, amongst others.

Particularly preferred promoters according to the present invention include, but are not limited to the rice ActinI promoter, CaMV 35S promoter, Ubiquitin1 promoter (Ubi1), α-amylase promoter or EII-(1-3, 1-4)-β-glucanase promoter sequences.

According to this embodiment, one aspect is directed to a genetic construct comprising a promoter or functional derivative, part fragment, homologue, or analogue thereof, from a genomic clone equivalent of the nucleotide sequence defined by SEQ ID NO: 1 or SEQ ID NO:3 or a homologue, analogue or derivative thereof.

The genetic constructs of the present invention are particularly useful in the production of crop plants with enhanced malting characteristics. Such enhanced malting characteristics are selected from the list comprising, but not limited to, the modulation of dormancy, more uniform germination of seed, high post-kilning levels of hydrolytic enzymes required during malting, more rapid filtration of the mash, less cloudy precipitate formation and altered alcohol content in the finished product. In a preferred embodiment, the said crop plant is a monocotyledonous plant species selected from the group including wheat, barley, rice, rye, maize, or sorghum. In a particularly preferred embodiment, the crop plant is barley.

The recombinant DNA molecule carrying the sense, or antisense, or ribozyme or co-suppression molecule of the present invention and/or genetic construct comprising the same, may be introduced into plant tissue, thereby producing a "transgenic plant", by various techniques known to those skilled in the art. The technique used for a given plant species or specific type of plant tissue depends on the known successful techniques. Means for introducing recombinant DNA into plant tissue include, but are not limited to, transformation (Paszkowski et al., 1984), electroporation (Fromm et al., 1985), or micro injection of the DNA (Crossway et al., 1986), or T-DNA-mediated transfer from Agrobacterium to the plant tissue. Representative T-DNA vector systems are described in the following references: An et al.(1985); Herrera-Estrella et al. (1983a,b); Herrera-Estrella et al. (1985). Once introduced into the plant tissue, the expression of the introduced gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

A still further aspect of the present invention extends to a transgenic plant such as a crop plant, carrying the foregoing sense, or antisense, or ribozyme, or co-suppression, or gene-targeting molecule and/or genetic constructs comprising the same. Preferably, the transgenic plant is one or more of the following: wheat, barley, rice, rye, maize, or sorghum, amongst others. Additional species are not excluded.

In a particularly preferred embodiment, the present invention provides a transgenic rice plant transformed with a GAMyb genetic sequence set forth in SEQ ID NO: 1 or SEQ ID NO:3 or a complementary sequence, homologue, analogue or derivative thereof.

In a most particularly preferred embodiment, the transgenic rice plant according to the invention is transformed with an antisense genetic construct comprising a sequence of nucleotides derived from the 3′ region of SEQ ID NO:3 or a complementary strand, homologue, analogue or derivative thereof. In an exemplification of this embodiment, there is provided a transgenic rice plant, transformed with an antisense genetic construct comprising nucleotide residues 1003 to 2113 of SEQ ID NO:3.

The present invention further extends to the progeny of a transgenic plant according to any one of the foregoing embodiments.

The present invention is farther described by reference to the following non-limiting Figures and Examples.

In the Figures:

FIG. 1 is a photographic representation of a Southern blot hybridisation of barley genomic DNA digested with BglII (lane 1), HindIII (lane 2), or XbaI (lane 3), and probe comprising nucleotides 1430 to 2189, of the nucleotide sequence set forth in SEQ ID NO:1.

Figure 2A:
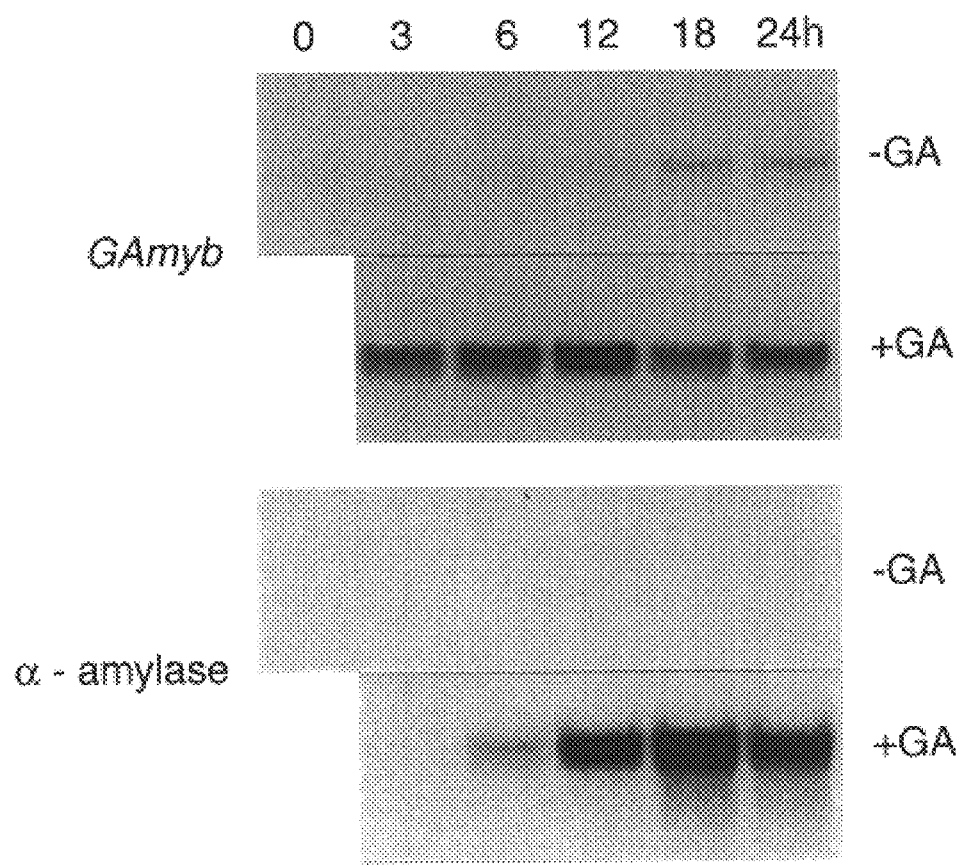
Figure 2B:
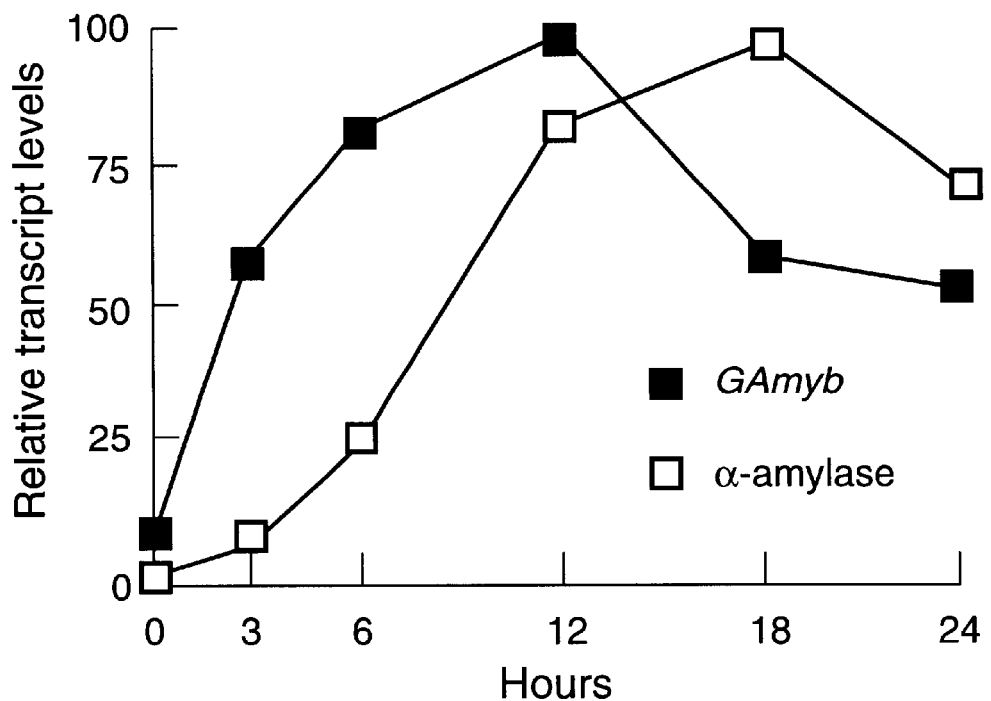

FIGS. 2A and 2B shows the effect of $GA_3$ on GAMyb and α-amylase gene expression. Panel (2A) is a photographic representation of a northern blot hybridisation experiment in which isolated barley aleurone layers were incubated with or without $GA_3$, RNA was then isolated and probed with a 3' gene-specific GAMyb cDNA probe, or a high-pI α-amylase cDNA, as indicated on the Figure. Numbers above the lanes indicate hours after the start of hormone treatment. Panel (2B) is a graphical representation showing the time course for induction of expression of the GAMyb gene, by application of $GA_3$.

Figure 3:
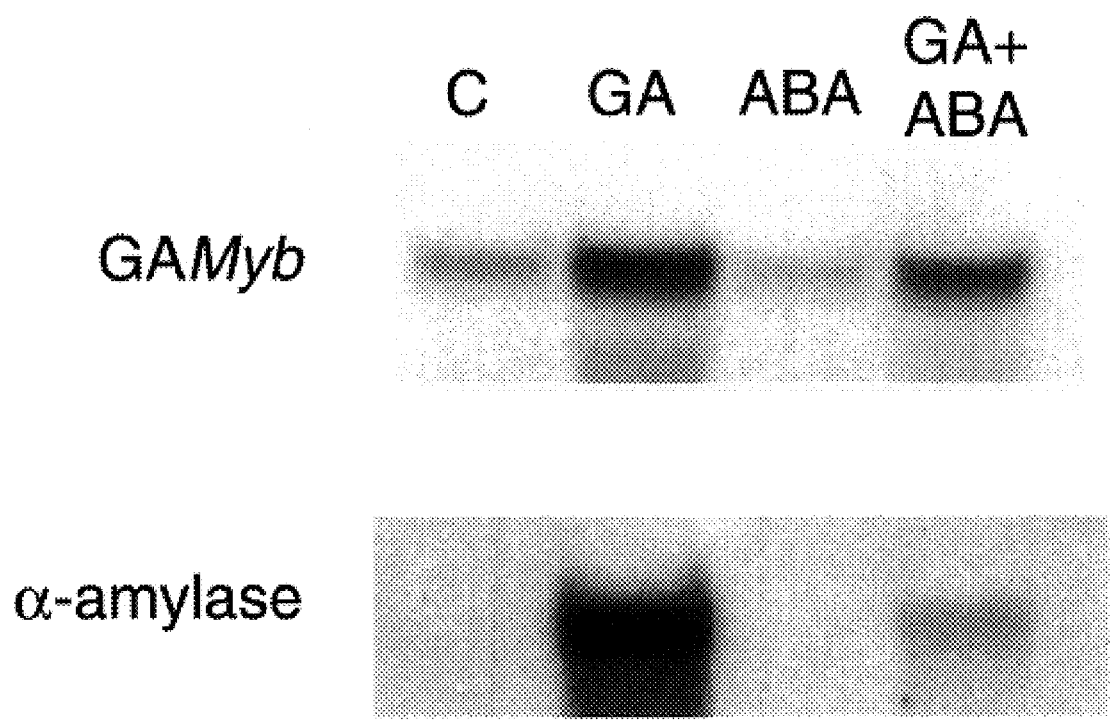

FIG. 3 is a photographic representation of a northern blot hybridisation experiment, showing the combined effect of $GA_3$ and ABA on GAMyb gene expression. Isolated barley aleurone layers were incubated either without hormone (lane 1), or in the presence of $GA_3$ (lane 2), ABA (lane 3), or GA+ABA (lane 4), prior to extraction of RNA. Northern blots were probed with either a gene-specific GAMyb probe (top panel), or as a control, with the α-amylase probe, as described in the legend to FIG. 2.

Figure 4:
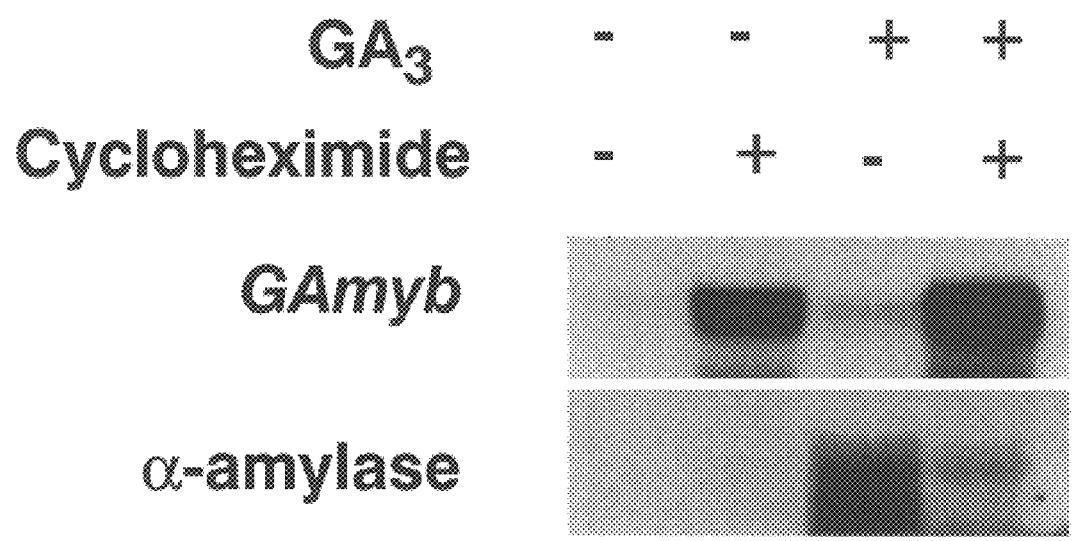

FIG. 4 is a photographic representation of a northern blot hybridisation experiment showing the differential effect of cycloheximide on GAMyb and α-amylase gene expression levels. Isolated aleurone layers were incubated for 6 hr, with either no $GA_3$ or cycloheximide (lane 1), cycloheximide alone (lane 2), $GA_3$ alone (lane 4), or $GA_3$ plus cycloheximide (lane 4). RNA was then isolated and probed with. The probes described in the legend to FIG. 2.

Figure 5:
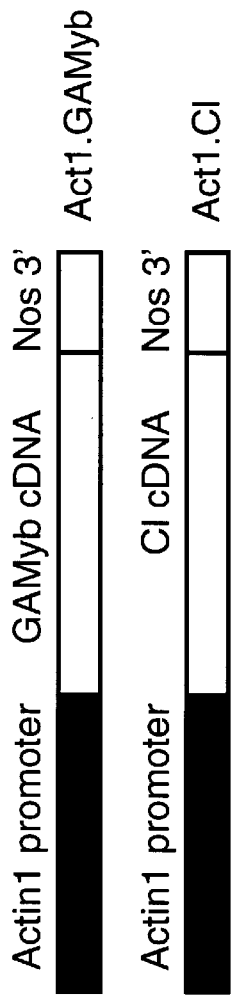
Figure 5:
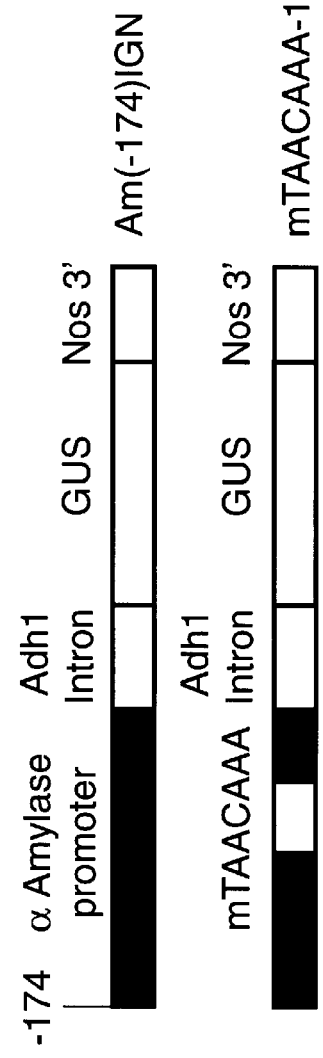

FIG. 5 is a diagrammatic representation showing the effector constructs pAct1. GAMyb and pAct1.C1 and the reporter constructs Am(−174)IGN and mTAACAAA-1.

Figure 6B:
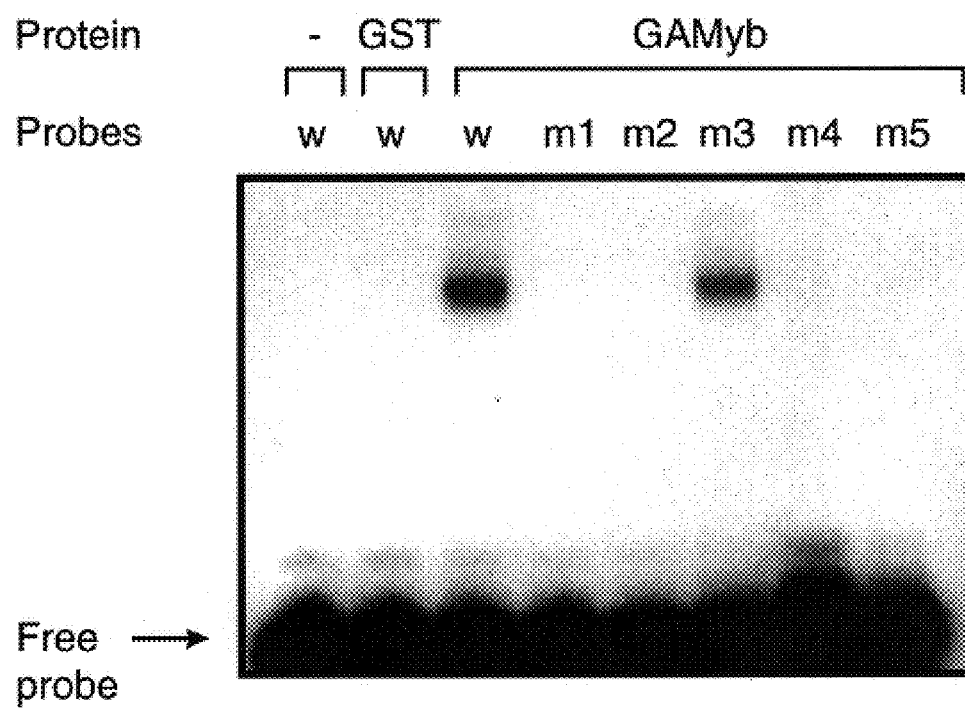

FIGS. 6A and 6B shows binding of the GAMYB protein to a 22 basepair α-amylase promoter fragment containing the TAACAAA box. Panel (6A) is a diagrammatic representation showing nucleotide sequences of oligonucleotide probes used in gel mobility shift assays. Probe w contains wild-type α-amylase promoter sequence, from −149 to −128 (Jacobsen and Close, 1991). Probes m 1–5 contain mutations in the TAACAAA box, as indicated. Panel (6B) is a photographic representation showing a gel mobility shift assay using affinity-purified recombinant GAMYB protein and $^{32}$P-labelled oligonucleotide probes described in panel (6A). Lane 1 contained probe w without protein; lane 2 , probe w and recombinant glutathione-S-transferase (GSI); lane 3, probe w and GAMYB; lane 4, probe m-1 and GAMYB; lane 5, probe m-2 and GAMYB; lane 6, probe m-3 and GAMYB; lane 7, probe m4 and GAMYB; lane 8, probe m-5 and GAMYB.

Figure 7:
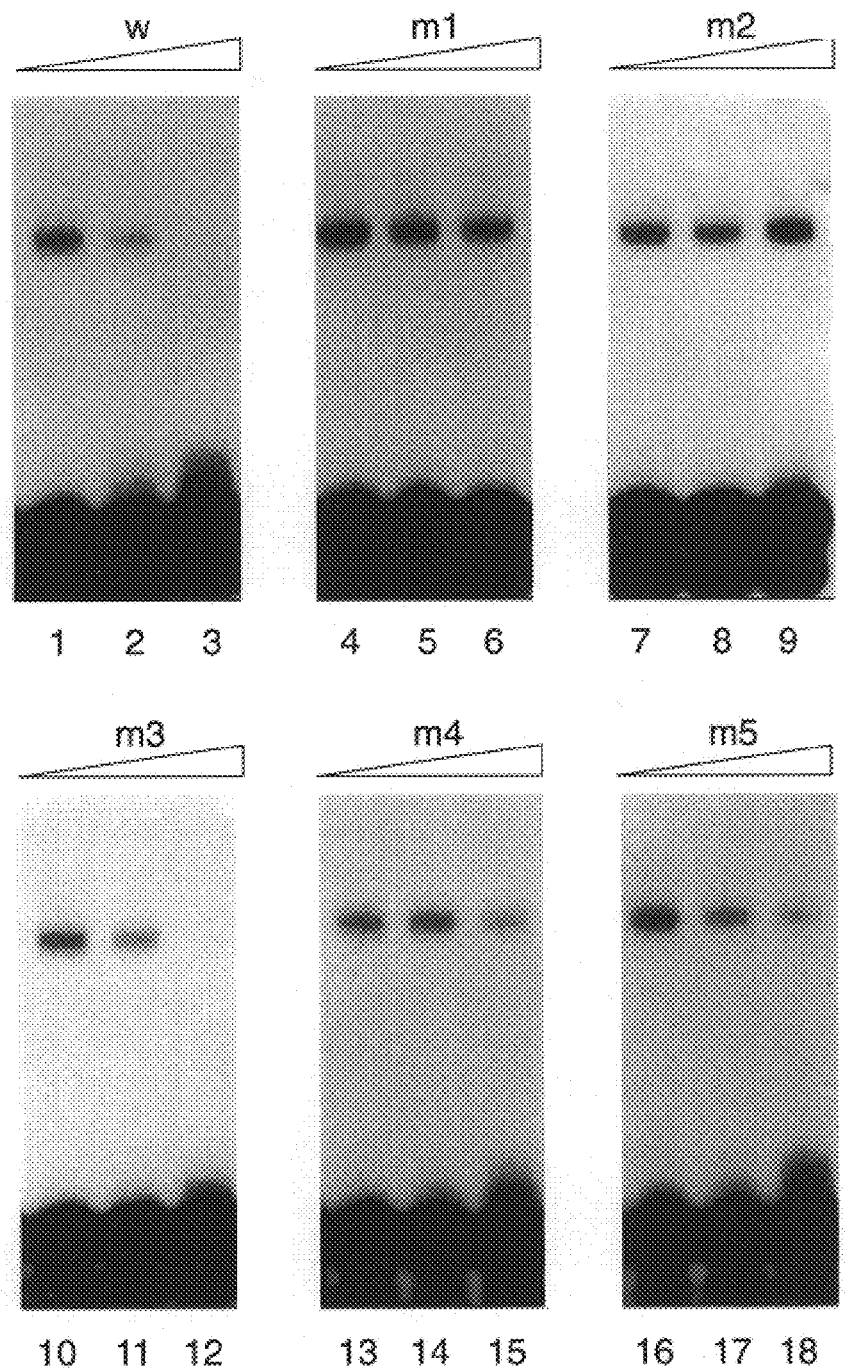

FIG. 7 is a photographic representation of a gel mobility shift assay showing competition for binding of recombinant GAMYB protein to probe w. Unlabelled competitor oligonucleotides w (lanes 1–3), m-1 (lanes 4–6), m-2 (lanes 7–9), m-3 (lanes 10–12), m4 (lanes 13–15), and m-5 (lanes 16–18), were incubated with affinity-purified recombinant GAMYB protein, prior to the addition of labelled probe w. The competitor DNA used is indicated at the top of each gel in the figure. In each gel indicated in the figure, the left-hand lane (i.e. lanes 1,4,7,10,13,16) shows the DNA-protein complex formed in the absence of any competitor DNA. The middle lane in each gel (i.e. lanes 2,5,8,11,14,17) shows the effect of adding a 10-fold molar excess of each competitor DNA. The right-hand lane in each gel (i.e. lanes 3,6,9,12, 15,18) shows the effect of adding a 100-fold molar excess of each competitor DNA.

Figure 8B:
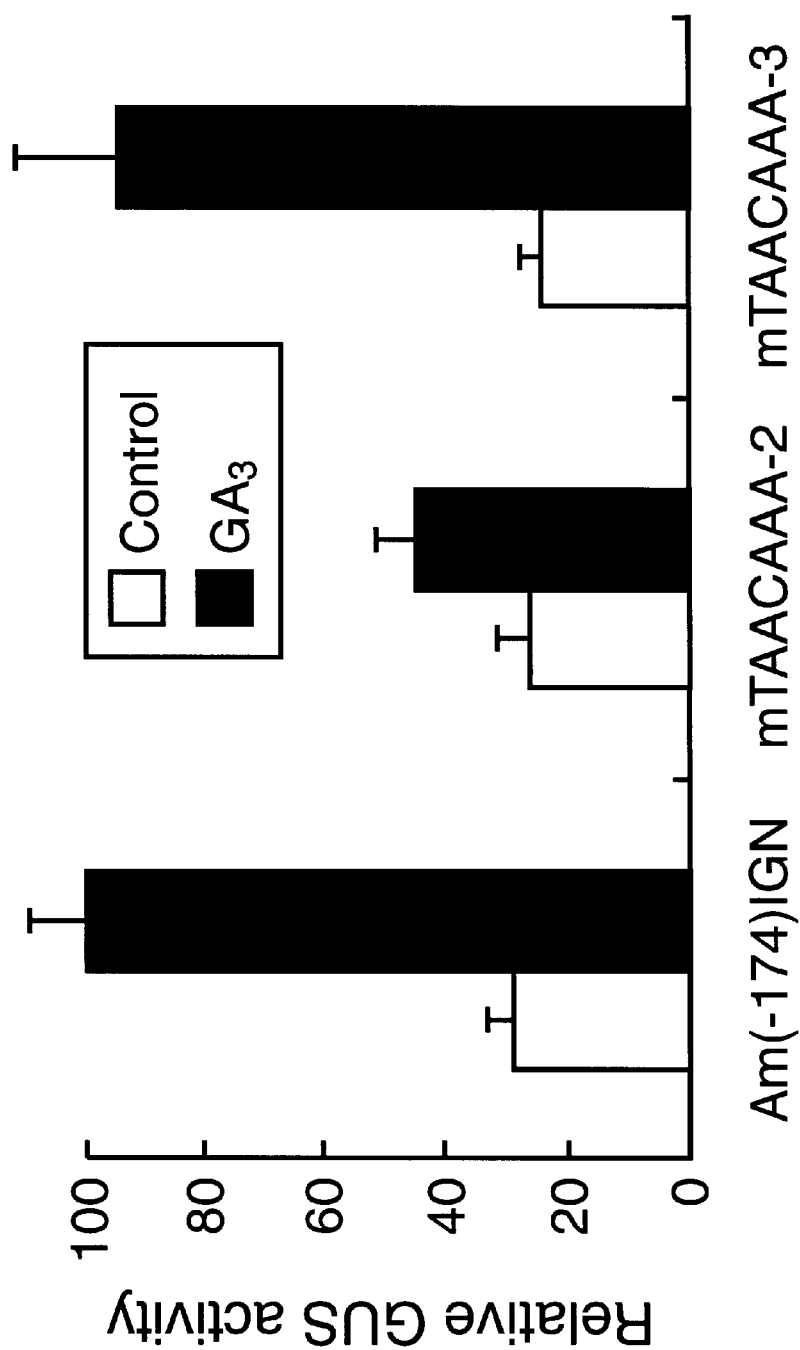

FIGS. 8A and 8B shows transient expression analysis of high-pI α-amylase promoter with GAMYB binding-site mutations. Panel (8A) is a diagrammatic representation showing wild-type and mutant α-amylase promoters sequences. Am(−174)IGN contains a wild-type binding site for the GAMYB protein. mTAACAAA-2 and -3 contain the single base-pair mutations indicated, in the GAMYB binding site. Panel (8B) is a graphical representation showing $GA_3$-responsiveness of the wild-type and mutant high-pI α-amylase promoters. Am(−174)IGN, mTAACAAA-2 and -3 were bombarded into intact aleurone cells and incubated with either no hormone (control), or $GA_3$. β-glucuronidase (GUS) enzyme activity was determined. All GUS activity values are shown relative to the activity of Am(−174)IGN. Error bars represent standard error of the mean (n=11).

Figure 9:
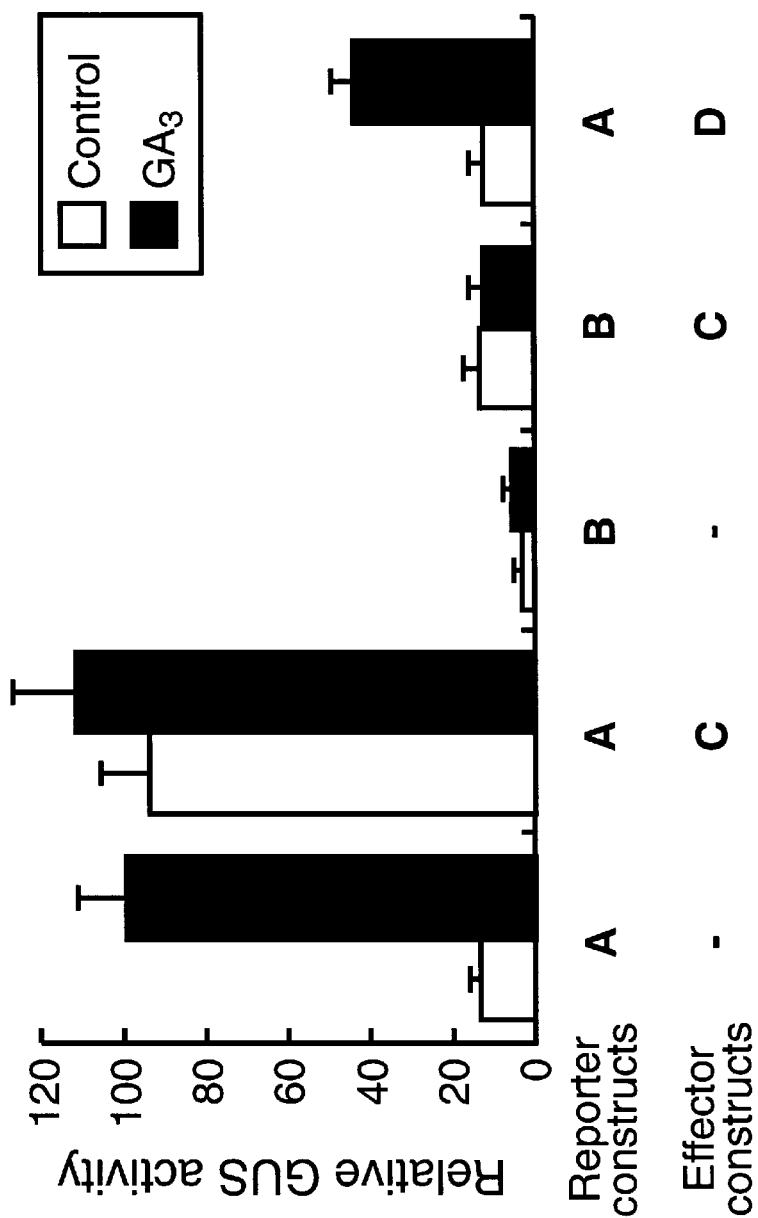

FIG. 9 is a graphical representation showing transactivation of the high-pI α-amylase promoter by the GAMYB protein, in barley aleurone cells. Constructs used are shown in FIG. 5. Intact aleurone cells were bombarded with reporter constructs and effector constructs as indicated, and incubated either without hormone (control), or in the presence of $GA_3$. The error bars represent the standard error of the mean (n=12 to 34).

FIG. 10 is a tabular representation showing transactivation of the promoters of three cereal aleurone genes, the barley Amy 32b gene promoter, the barley EII-(1-3, 1-4)-β-glucanase gene promoter and the wheat Cathepsin β-like gene A121 promoter, in barley aleurone cells. The p113Act1.cas and Act1.GAMyb constructs are described in Example 6. Plasmid EII.IGN contains 1600 bp of the EII-(1-3, 1-4)-β-glucanase gene promoter placed upstream of a reporter gene cassette comprising maize Adh1 intron1/GUS/nopaline synthase 3' terminator sequences (which are also contained in plasmid pAm(−174) IGN described in Example 6). Plasmid mlo22 contains the barley Amy 32b promoter linked to a GUS reporter gene and is described by Lanahan et al. (1992). Plasmid CBG1 contains the wheat Cathepsin β-like gene promoter A121 linked to a GUS reporter gene and is described by Cejudo et al. (1992). Intact barley aleurone cells were bombarded with reporter and effector constructs as indicated, and incubated either without hormone or in the presence of $GA_3$. In the case of the Dhn7 construct, intact aleurone cells were incubated without hormone (control), or in the presence of ABA. GUS activities were determined after 24 h incubation and are shown relative to the activity of the respective construct co-shot with the Act1.cas control effector construct.

Figure 11:
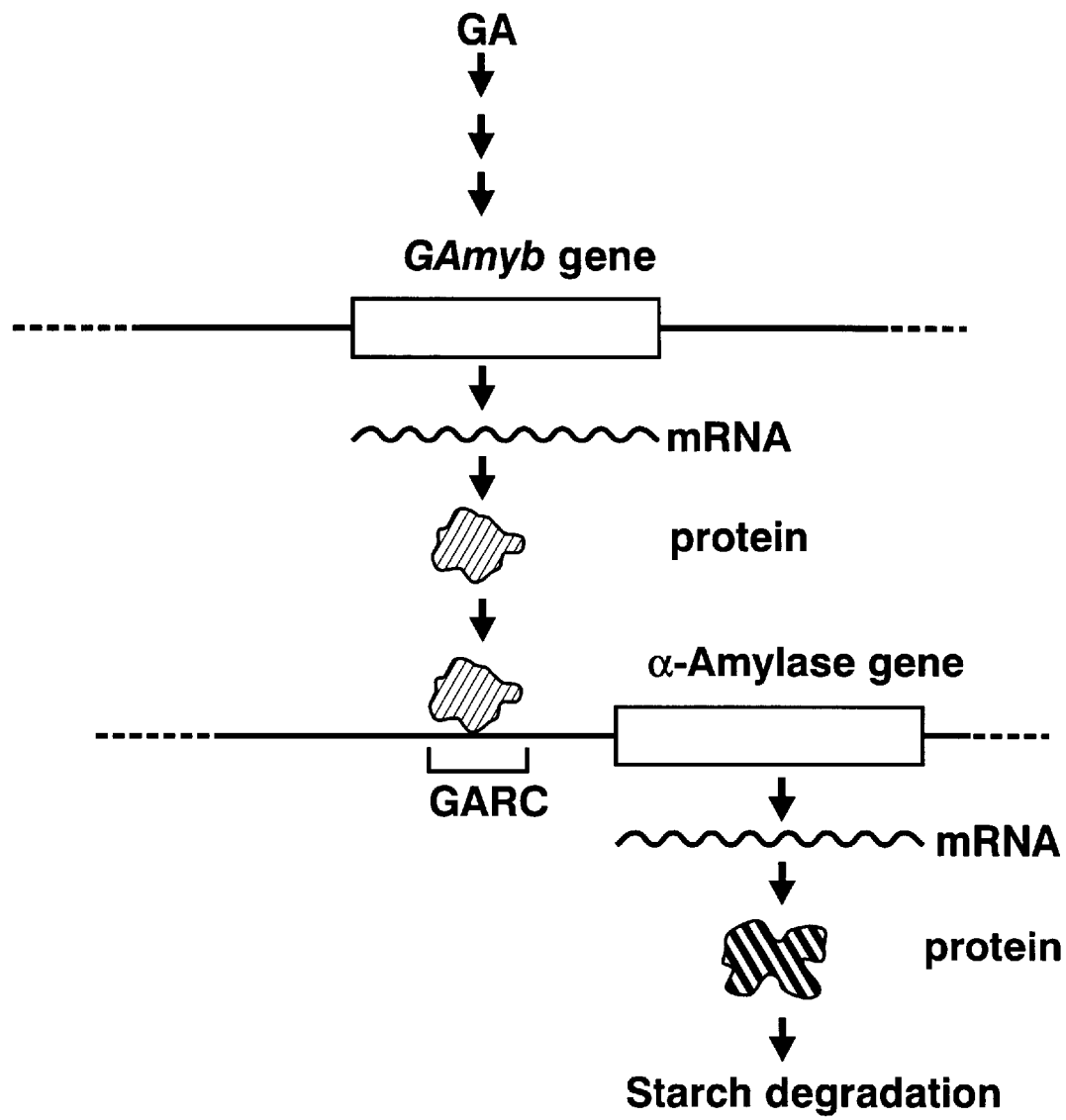

FIG. 11 is a schematic representation of the proposed GA response pathway for high-pI α-amylase gene expression in barley aleurone cells.

FIG. 12 is a schematic representation of an alignment of the deduced amino acid sequences of rice (upper) and barley (lower) GAMYB polypeptides and. The aligned R2 and R3 repeats of the MYB DNA binding domain are boxed. A putative transcriptional activation domain present in both sequences is underlined.

Figure 13A:
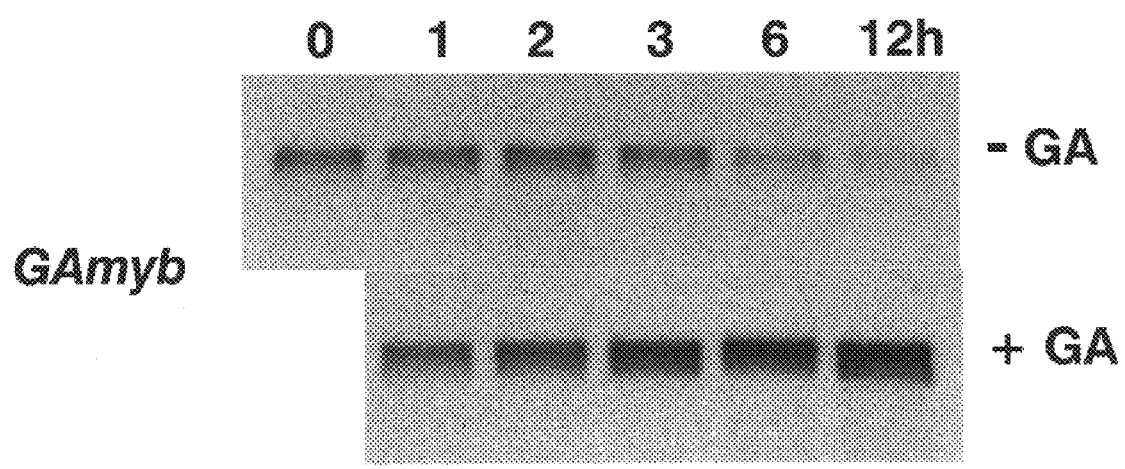
Figure 13B:
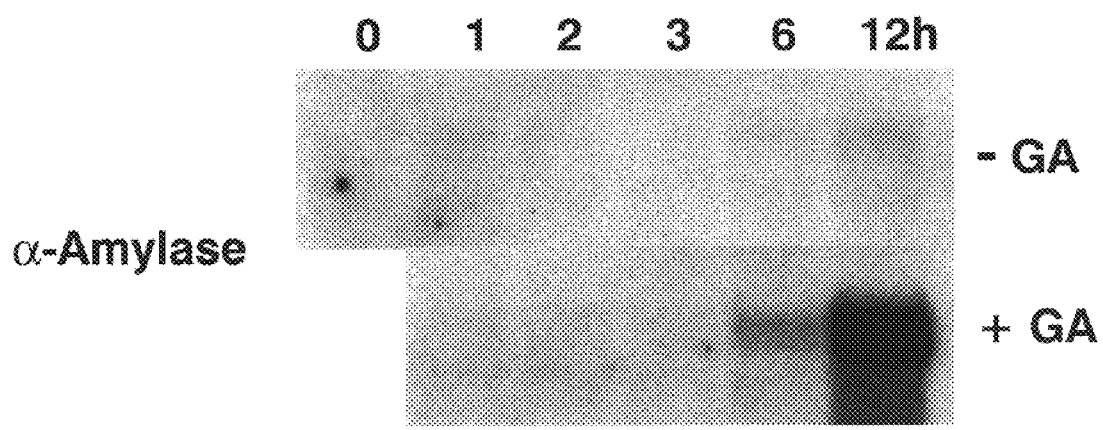
Figure 13C:
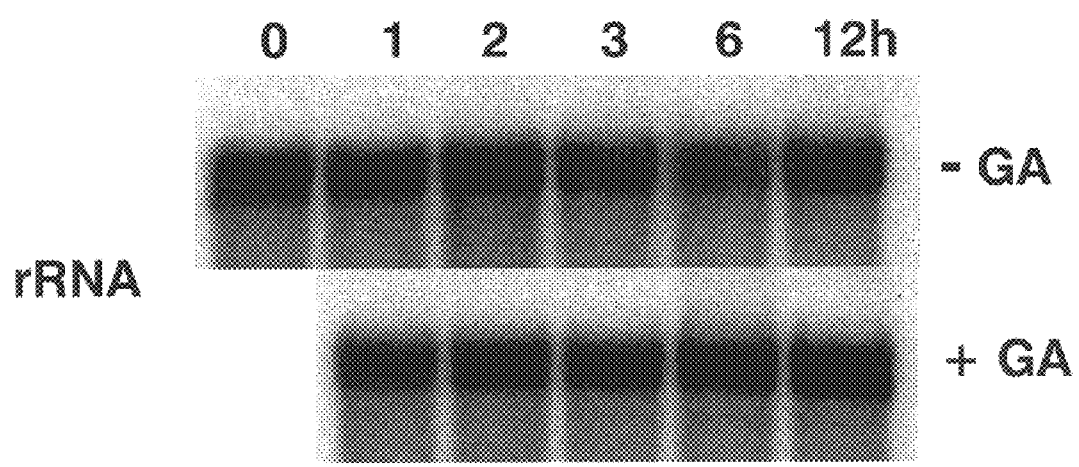

FIGS. 13A–13C are a photographic representations of a northern blot hybridisation showing the effect of gibberellin on GAMyb and α-amylase gene expression in rice endosperm. RNA was isolated from rice endosperm half grains (var Taipai 309) (Schuurink et al., 1996) which had been hydrated in 10 mM CaCl$_2$ overnight at 28° C. and then incubated in 10 mM CaCl$_2$, 150 μm ml$^{-1}$ cefotaxime, 50 units ml nystatin, and either no hormone (control) or 10$^{-6}$ M gibberellic acid (GA) at 30° C. After blotting the RNA was probed with a gene-specific 3' OsGAMyb probe (panel 13A); a low-pI barley α-amylase cDNA (panel 13B), and a wheat ribosomal DNA clone pTA250 (Gerlack and Bedbrook, 1979; panel 13C). Numbers above each lane indicate hours (h) after the start of the treatment. 10 μg RNA was loaded per lane.

Figure 14A:
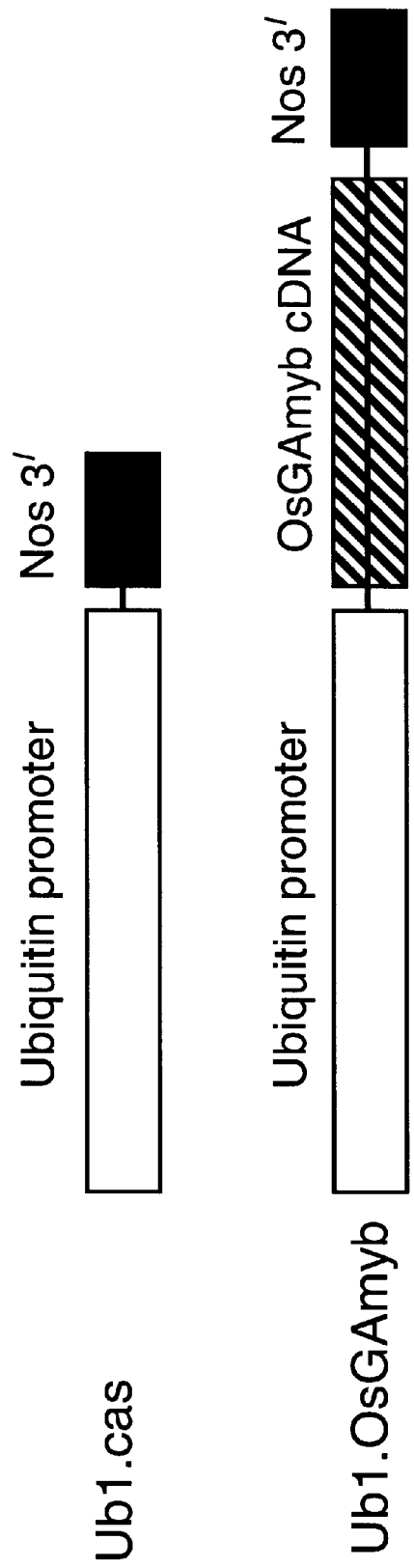

FIGS. 14A–14B are a schematic representations showing transactivation of barley low-pI α-amylase promoter by rice GAMYB in barley aleurone cells. (14A) The GAMyb effector construct was made by inserting the OsGAMyb cDNA containing the entire open reading frame into the multi cloning site in the maize Ubiquitin gene expression cassette, Ubi1.cas, comprising the maize Ubiquitin gene promoter fused to a multi cloning site and Nos 3' terminator. The reporter construct, mlo22 consists of the barley Amy32b promoter fused to a GUS reporter gene (Lanahan et al., 1992). (14B) Intact aleurone cells were co-bombarded with the reporter construct and effector constructs and incubated with no hormone (control) and gibberellic acid (GA) as described in Examples 10–12. Preparation of extracts and assays of GUS activity were as described by Gubler et al. (1995).

Figure 15A:
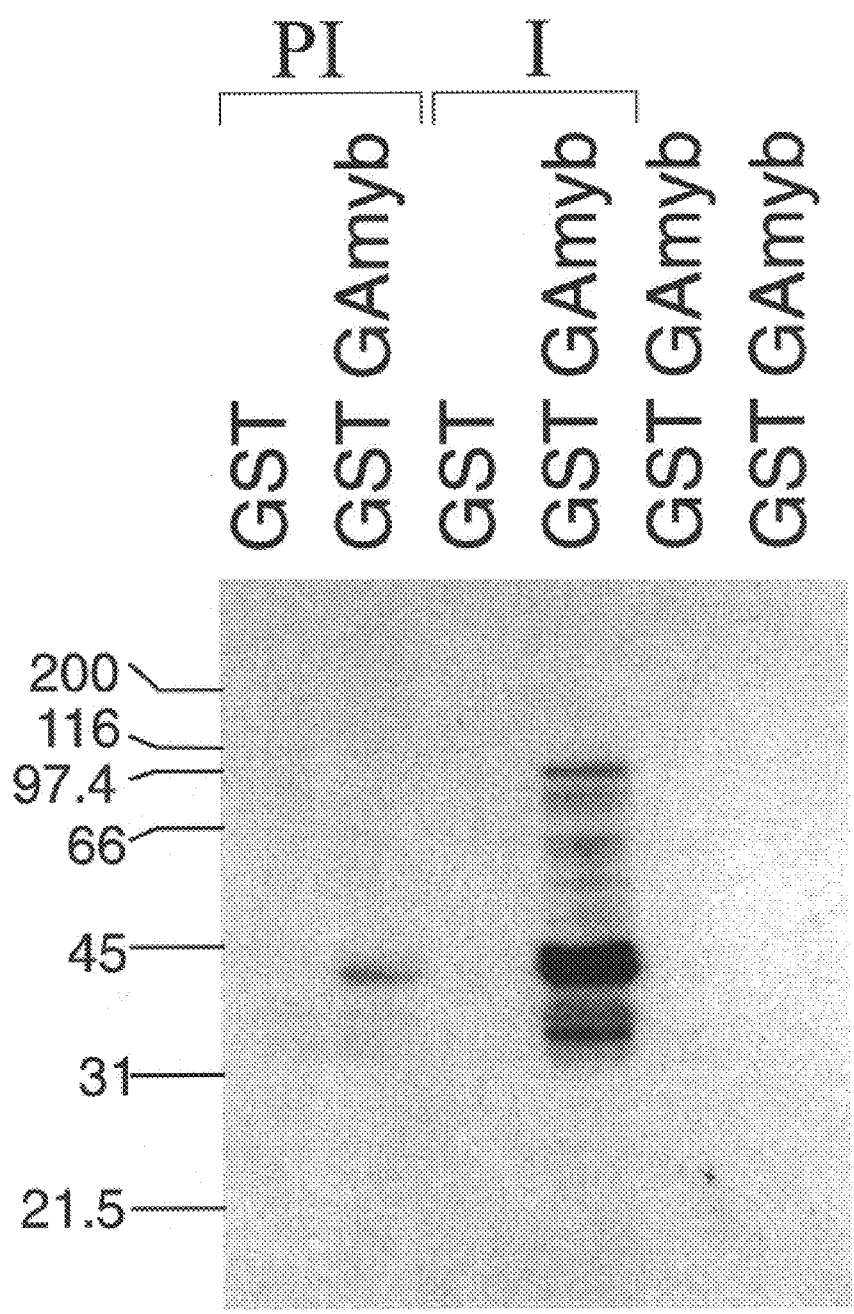
Figure 15B:
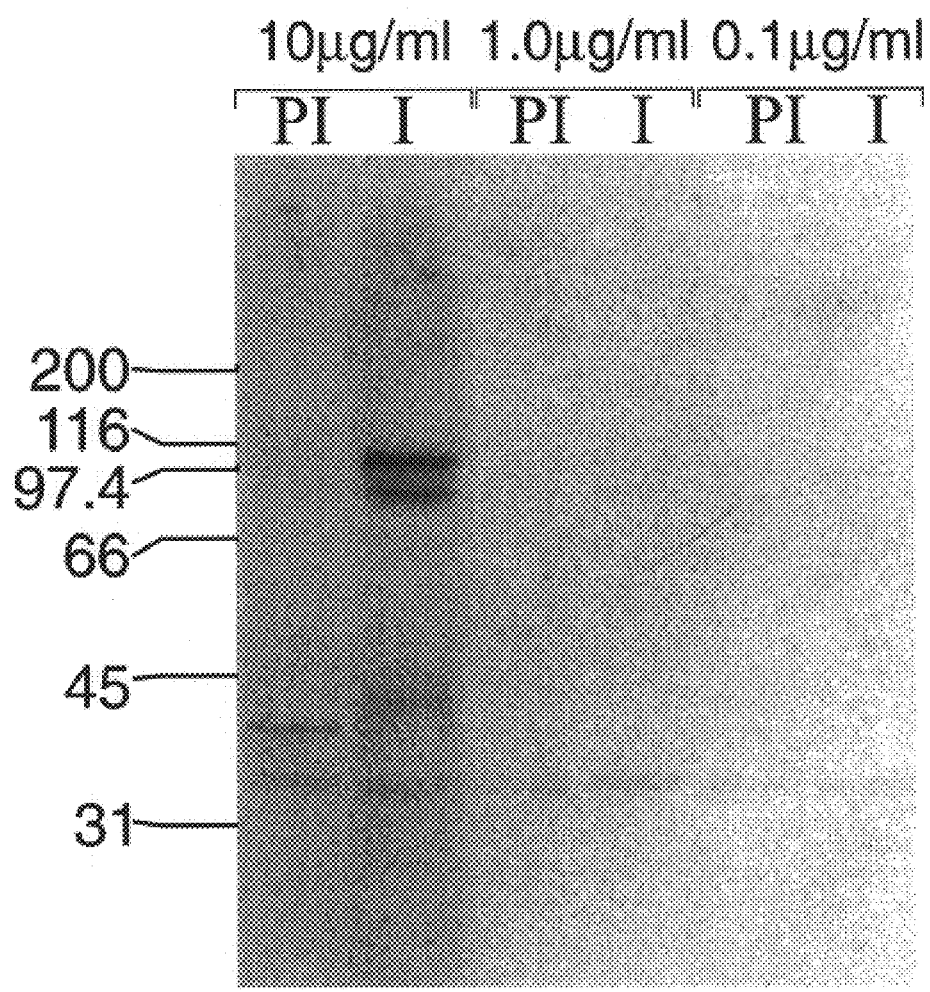

FIGS. 15A–15B are a photographic representations of a western blot analysis of the GAMYB fusion protein. In panel (15A), the GAMYB fusion protein was detected by immunoblotting with purified antibody raised against a synthetic peptide comprising amino acids 1–14 of barley GAMYB. GST, glutathione-S-transferase; GST-GAMyb, GST-GAMYB fusion protein; PI, pre-immune sera; I, immune sera. The numbers on the left of the figure indicate apparent molecular mass, in kDa. In panel (15B), the GAMYB fusion protein was detected by immunoblotting with purified antibody raised against a synthetic peptide comprising amino acids 481–494 of the barley GAMYB polypeptide. Pre-immune or immune sera (0.1 to 10 μg ml$^{-1}$) were incubated with blots containing GST-GAMYB fusion protein. The numbers on the left of the panel indicate apparent molecular weight, in kDa.

Figure 16:
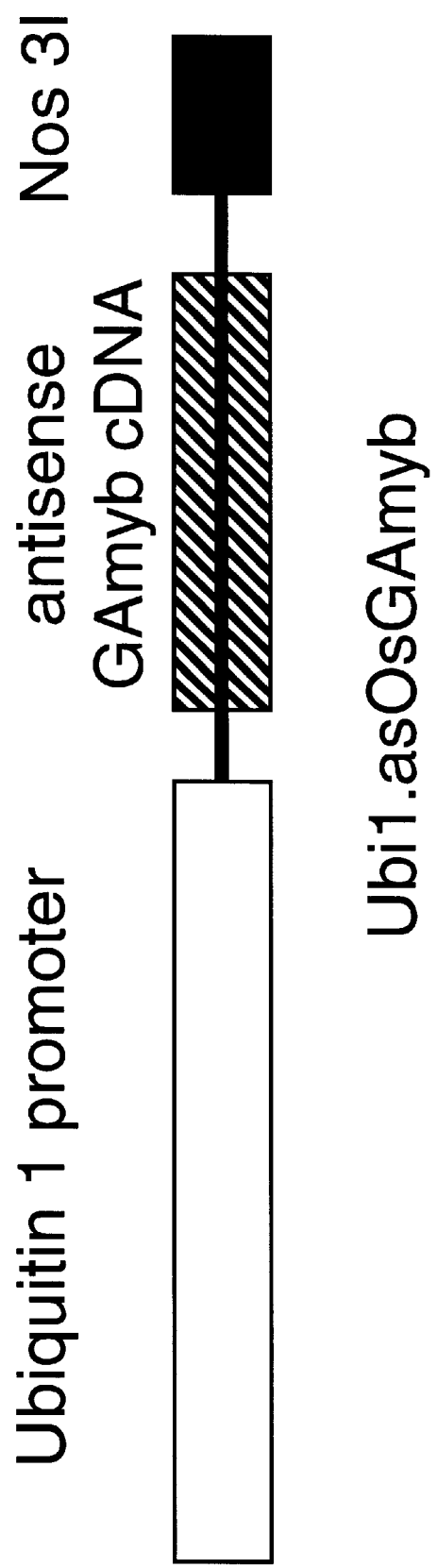

FIG. 16 is a schematic representation of an antisense genetic construct comprising the ubiquitous promoter sequence operably connected to the OsGAMyb cDNA sequence placed in antisense orientation upstream of the nopaline synthase terminator sequence.

Figure 17:
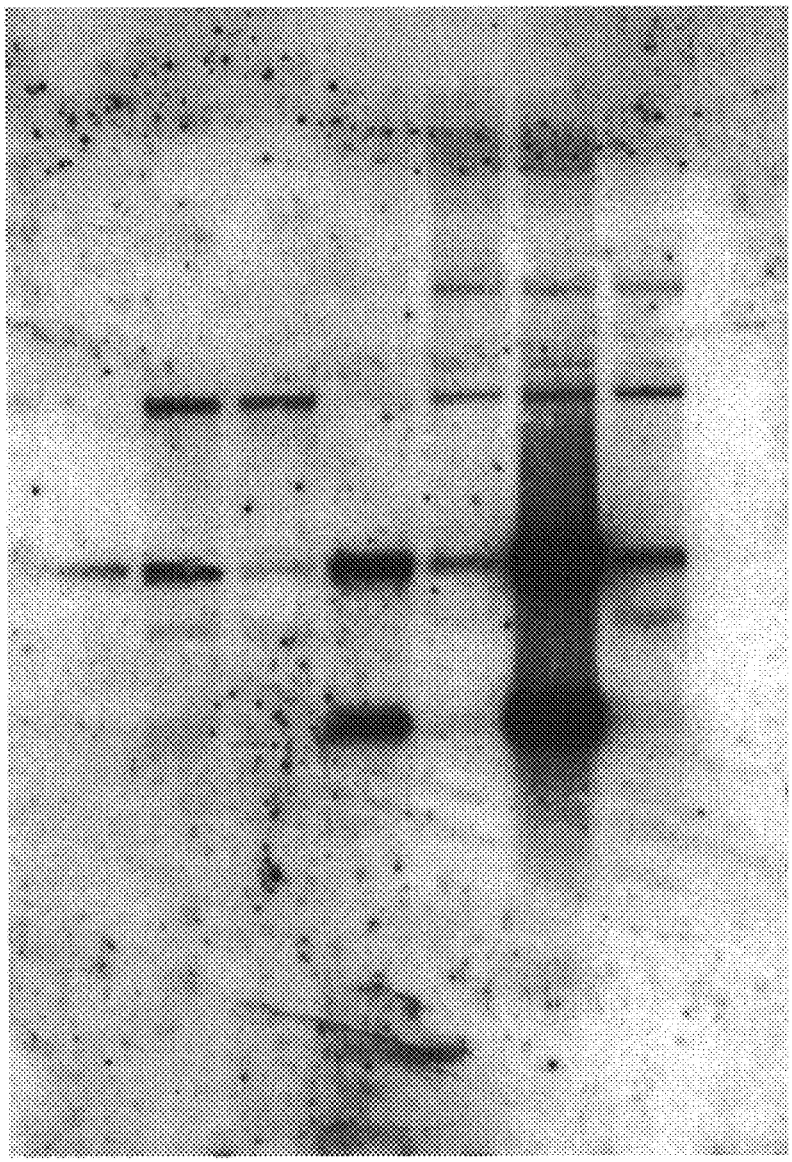

FIG. 17 is a photographic representation of a Southern blot hybridisation demonstrating integration of the Ubi1.asOsGAmyb construct into the genomic DNA of 6 sibling T$_0$ rice plant lines (JSH 15.2.28 lines 1–6). The plasmid control (lane marked "1 copy") and the genomic DNA (lanes 1–6) had been digested with the enzyme EcoRI. The blot was probed with 3' end of the OsGAMyb cDNA.

Figure 18:
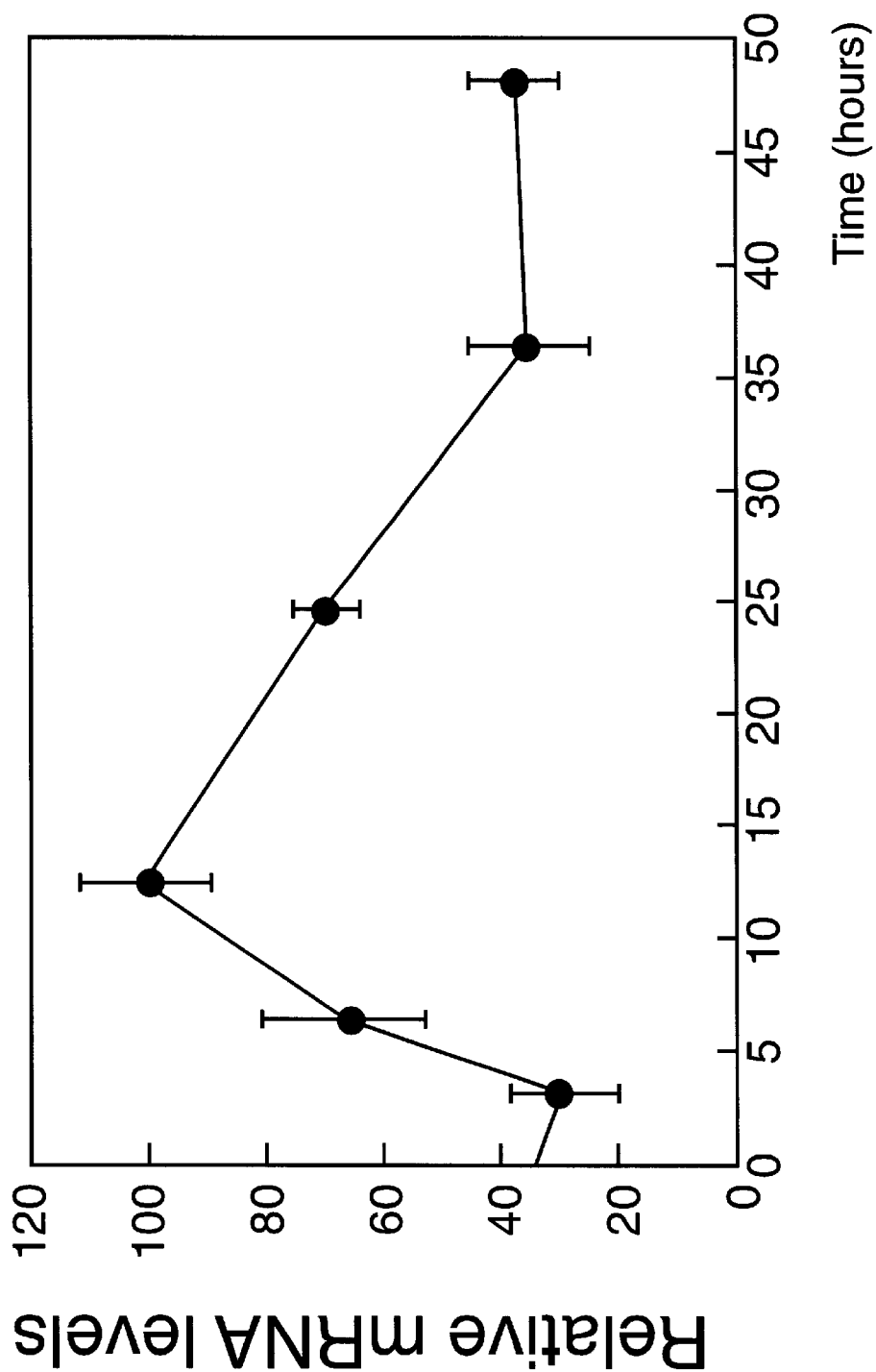

FIG. 18 is a graphical representation showing HvGAMyb mRNA levels in germinating barley embryos.

Single letter and three letter abbreviations used for amino acid residues in the specification are defined in Table 1.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

EXAMPLE 1

Molecular cloning of GAMyb cDNA

A barley (*Hordeun vulgare* cv Himalaya) cDNA library prepared from isolated aleurone layers (Stratagene, La Jolla, Calif.) was screened for putative Myb cDNAs. The library was screened with a 174 bp PCR fragment which contained sequences homologous to the region between conserved R2 and R3 repeats of the maize C1 cDNA (amino acid 49 to 106). The probes were labelled [α-$^{32}$P]dCTP by random priming. Hybridization was in 6×SSC and 0.1% SDS, 1×Denhardt's solution, 100 μg/ml salmon sperm DNA at 54° C. and washed in 3×SSC, 0.1% SDS at 54° C. (Jackson et al., 1991). Positive plaques were purified by a further round of plaque hybridisation. The pBluescript Sk(-) plasmid containing the GAMyb insert was excised in vivo according to the manufacturer's instructions (Stratagene). The cloned cDNA fragment (pGAMyb) was sequenced by the dideoxy terminator cycle sequencing method using an Applied Biosystems' 370A DNA sequencer. From an initial screen of 10$^6$ recombinant phages one partial cDNA clone, GAMyb, was isolated that contained a 1991 bp insert.

Amplification of 5' end of cDNAs was performed by the 5' RACE procedure as described by Frohman (1990). Poly (A)+RNA from GA-treated barley aleurone layers was reverse transcribed using a gene specific primer 5'-TGTTCTTCTGCACCGCGTTC-3' SEQ ID NO.7. Following removal of excess primer, a 5' poly A tail was synthesised on the single-stranded cDNA using terminal deoxynucleotidyl transferase. PCR amplification was performed using a nested 3' gene-specific primer 5'-GTGCTTCACGTACTCCAC-3' SEQ ID NO:8 and an oligo dT primer. PCR fragments were cloned by blunt end ligating into pCR-Script (Stratagene) according to the manufacturer's instructions. Positive clones were identified by colony hybridisations (Sambrook et al., 1989) and sequenced.

The longest PCR product cloned was 408 bp and it was shown by sequence analysis to extend the cDNA sequence a further 271 bp. Partial sequencing of a Himalaya barley genomic clone which contains the GAMyb gene confirmed the sequence of the 5' RACE clone. The complete nucleotide sequence of the full-length barley GAMyb cDNA and deduced amino acid sequence is shown in SEQ ID NO: 1 and SEQ ID NO: 2, respectively.

The longest open reading frame of SEQ ID NO: 1 extends 1659 bp from position 275 to a TAG stop codon found at positions 1934–1936 and encodes a polypeptide of 553 amino acid residues. Amino acid residues 42–94 (R2) and 95–145 (R3) of SEQ ID NO: 2, are highly homologous to the R2 and R3 regions of the DNA-binding domain of animal and plant MYB proteins. Both these repeats contain conserved tryptophan residues which play a critical role in stabilizing the DNA-binding domain of animal MYBs (Ogata et al., 1992). Outside the putative DNA binding domain, there is little similarity between the derived amino acid sequences of GAMYB and other MYBs.

EXAMPLE 2

Genomic DNA isolation and Southern analysis

DNA was isolated from etiolated leaves from 6 day old barley seedlings using the method described by Dellaporta et al. (1993). For detection of GAMyb gene in genomic DNA, 25 µg of genomic DNA digested with BgIII or HindIII or XbaI was fractionated on 1% (w/v) agarose gel and blotted onto nylon membrane. The blot was hybridized with a $^{32}$P-labelled PCR fragment which contained sequences between nucleotides 1430 and 2189 of the nucleotide sequence set forth in SEQ ID NO: 1. Hybridisation was carried out at 42° C. in 6×SSC, 5×Denhardt's solution [0.1% (w/v) Ficoll, 0.1% (w/v) PVP and 0.1% (w/v) BSA], 0.1% (w/v) SDS and 50% (v/v) formamide. The blots were washed in 0.1×SSC, 0.1% (w/v) SDS at 65° C.

Southern analysis of barley genomic DNA cut with HindIII and XbaI using the 3' end of the cDNA (from position 1430 to 2189) as a probe, showed only one band which hybridized with the probe (FIG. 1). This result indicates there is only one copy of the GAMyb gene. When the DNA was cut with BglII, two bands were observed with the 3' probe. The appearance of two bands is due to an internal BgLII site within the sequences that were probed.

EXAMPLE 3

GAMyb gene expression is regulated by GA

Aleurone layers were prepared from grains of *Hordeum vulgare* cv Himalaya (1985 harvest, Washington State University, Pullman) as described previously (Chrispeels and Varner, 1967). The isolated layers were isolated from 3 day imbibed de-embryonated half grains and incubated in flasks containing 2 ml 10 mM $CaCl_2$, 150 µg/ml cefotaxime, 50 IU/ml nystatin and no hormones (control), or $10^{-4}$M gibberellic acid (GA) or $10^{-6}$M gibberellic acid and $5×10^{-5}$ M abscisic acid (ABA) (GA+ABA) at 25° C. for various times. Following hormone treatments, the layers were stored in liquid nitrogen until required. Aleurone layers that were to be treated with cycloheximide, were pre-incubated with 50 µM cycloheximide, calcium chloride and antibiotics for 30 min before the hormones were added.

RNA was isolated from aleurone layers according to Chandler and Jacobsen (1991) with one minor modification. Bentonite was omitted from homogenisation medium. For Northern analysis, 20 µg of aleurone RNA was fractionated in 1% (w/v) agarose gel containing formaldehyde and blotted onto nylon membrane. The blots were hybridized with a $^{32}$P-labelled 991 bp PCR product containing gene specific GAMyb sequences (nucleotide 1198 to 2189 of the sequence set forth in SEQ ID NO: 1). Hybridisation conditions were essentially as described in Example 2.

After autoradiography, Northern blots were stripped of the GAMyb probe, and reprobed with a 1.1 kb DNA fragment containing the pHV19 cDNA clone, which is a barley high-pI amylase cDNA isolated from $GA_3$-treated aleurone layers (Chandler et al., 1984) and a control 9 kb wheat mRNA clone, pTA71 (Gerlach and Bedbrook, 1979). All DNA probes were labelled by oligonucleotide priming (Feinberg and Vogelstein, 1983). mRNA transcripts were quantified using a Molecular Dynamics Phosphorimager and ImageQuant software. GAMyb and high-pI α-amylase mRNA transcript levels were normalized to rRNA levels to overcome error in RNA quantitation by spectrophotometry.

To test whether GAMyb gene expression was GA-regulated, Northern blots of RNA from control and $GA_3$-treated barley aleurone layers from various time points were probed using a 3' gene-specific GAMyb cDNA probe (FIG. 2A). In control treatments, GAMyb mRNA levels remained low for the first 12 h and then increased slightly over the next 12 h. In contrast, GAMyb mRNA levels increased rapidly in response to $GA_3$. By 12 h, the level in $GA_3$-treated aleurone layers was approximately 5 fold higher than that found at the corresponding time for control treatments. However the increase in mRNA levels was transient. Between 12 and 24 h, the level of mRNA had declined by 50%. The same blot was stripped and hybridized using the barley high-pI α-amylase cDNA clone, PHV19 (Chandler et al. 1984). The α-amylase mRNA was found to be strongly induced by $GA_3$.

To compare the kinetics of GAMyb and α-amylase mRNA accumulation in $GA_3$-treated barley aleurone layers, transcript levels in the blot shown in FIG. 2a were quantified using a phosphorimager and normalized to rRNA. The time course shown in FIG. 2B shows that the expression of the GAMyb gene precedes α-amylase gene expression in $GA_2$-treated aleurone layers. GAMyb mRNA levels rise dramatically within the first 3 h after $GA_3$ addition, while the maximum rate of increase in α-amylase mRNA levels occurs later between 6 to 12 h. Examination of earlier time points indicted that GAMyb mRNA levels increased within 1 hr in response to $GA_3$. Maximal GAMyb mRNA levels (6–12 h) coincided with the maximal rate of accumulation of α-amylase mRNA indicating the possibility that the expression of the two genes may be causally linked.

EXAMPLE 4

GAMyb gene expression is regulated by abscisic acid

Abscisic acid (ABA) has been shown to antagonize GA action in barley aleurone layers. To test whether $GA_3$-induced GAMyb gene expression is also down-regulated by ABA, we probed Northern blots of RNA from control-, $GA_3$-, ABA- and $GA_3$+ABA-treated barley aleurone layers as described in Example 3 (FIG. 3). The response of GAMyb gene expression to $GA_3$ and ABA was very similar to that observed for α-amylase gene expression. Control and ABA-treated layers had very low levels of GAMyb and a- amylase mRNA. Quantification of mRNA levels using the phosphoimager indicated that the $GA_3$-induced increases in GAMyb and α-amylase mRNA levels was inhibited by ABA by about 40–50% and 80–100%, respectively.

To test whether the differential response of GAMyb and α-amylase gene expression to ABA was due to slowness of aleurone cells to respond to ABA to take up ABA, we preincubated aleurone layers with ABA for 30 min before adding $GA_3$. The ABA preincubation had no effect on GAMyb gene expression compared to treatments where there was no preincubation. The differential response indicates that α-amylase gene expression is far more responsive to ABA that GAMyb gene expression in barley aleurone.

Data presented in Examples 3 and 4 open up new insights into the mechanisms of ABA action in aleurone cells. The inhibition of α-amylase gene expression by ABA may be explained at least in part by the action of ABA on GAMyb gene expression. ABA inhibited GA-induced increases in GAMyb transcript levels by up to 50%. However ABA caused a far greater decrease in steady state levels of α-amylase mRNA than GAMyb mRNA indicating that the regulation of GAMYB activity may not be all at the transcriptional level. It is possible that ABA action regulates GAMYB activity not only at the level of transcription but at the level of post-transcription by promoting GAMYB phosphorylation. ABA may also be regulating the expression of MYBs which compete for the GAMYB-binding site in the α-amylase promoter. It is of interest to speculate that the known antagonistic effect of these two hormones at the level of gene expression may involve, in part, the expression of mutually antagonistic MYBs which are under she control of ABA or GA.

EXAMPLE 5

Cycloheximide induces the expression of GAMyb

To test whether GAMyb gene expression is also sensitive to the protein synthesis inhibitor, cycloheximide, we performed Northern blot analysis using a 3' gene specific GAMyb probe and a high-pI amylase cDNA probe (FIG. 4). The GAMyb mRNA levels in barley aleurone layers increased in response to $GA_3$ and cycloheximide alone, but the increase was much greater in the cycloheximide- treated layers compared to $GA_3$-treated layers. When the tissue was incubated with both $GA_3$ and cycloheximide, the increase in GAMyb mRNA was greater than with either treatment alone.

These results suggest strongly that protein synthesis is not required for GA induction of GAMyb gene expression and therefore the GAMyb gene is the first gene to be expressed in the GA-response pathway leading to expression of the high-pI α-amylase gene. The mechanisms involved in the induction and super-induction of mRNAs by cycloheximide are not yet clearly understood but may be due to mRNA stabilization.

EXAMPLE 6

Plasmid Construction

The construct Am(−174)IGN, which has been previously described (Jacobsen and Close, 1991), contains a deletion of a high-pi et-amylase gene promoter from barley (−174 to +54) fused to a reporter gene cassette (maize Adh1 intron 1/GUS/nopaline synthase 3' terminator sequence). The mTAACAAA-2 and mTAACAAA-3 constructs were created by using PCR to introduce single base pair mutations within the TAACAAA box of the Am(−174)IGN construct. Mutagenic forward primers are as follows:

mTAA11 (5'-GCCTGCAGGTCGACTCTAGAGAATCGC-CTTTGAGCTCA CCGTACCGGCCGAT GACAAACTCCGG-3" (SEQ ID NO:9));

mTAA12 (5'-GCCTGCAGGTCGACTCTAGAGAATCGC-CTTTTGAGCTCA CCGTACCGGCCGATAACA GACTCCGG-3" (SEQ ID NO:10));

reverse primer Am41 (5'-GTGTGCTGCGCAGCATGCCGG-3" (SEQ ID NO:11)).

PCR was performed using the mutagenic forward primers and the reverse primers, and pAm(−174)IGN as template DNA. The PCR products were cut with PstI and cloned into the PstI site at −41 in pAm(−41)IGN (Jacobsen and Close, 1991) thus producing Am(−174)IGN constructs containing single base-pair mutations at −142 (TGACAAA) and at −138(TAACAGA).

The pGEX vector (Smith and Johnson, 1988) was used for the production of glutathione S-transferase fusion proteins for gel mobility shift experiments. The pGEX.GAMyb construct was made by cloning a 1656-bp EcoRI fragment containing the GAMyb gene coding region (nucleotides 275 to 1930 of SEQ ID NO: 1) into the pGEX vector.

GAMyb and C1 effector constructs used in transient over expression experiments were synthesised by Cloning fragments containing the GAMyb or C1 coding regions into the multi cloning site of a plant expression vector, p113Act1.cas, containing the rice Actin1 promoter and 5' untranslated leader sequence (including intron 1) fused to a multi cloning site-Nos 3' terminator. The pAct1.GAMyb construct used in over expression experiments was prepared by first cloning the above-identified EcoR1 GAMyb fragment which contains the coding region into the EcoR1 site of pBluescript SKvector (Stratagene). The entire EcoR1 insert was then cut out as a HindIII-XbaI fragment and cloned directly into the multicloning site of the p113Act1.cas. The pAct1.C1 construct which contains the entire coding region of the C1 cDNA cloned downstream of the rice Actin1 promoter was also prepared using a similar strategy.

EXAMPLE 7

Production and Purification of GAMYB fusion protein

Purified proteins for gel-mobility shift assays were prepared from *Escherichia coli* XL1-blue cells, transformed with the pGEX.GAMyb construct prepared as described in the foregoing Example 6. The transformed cells were grown in 500 ml 2×YT medium containing 100 μg/ml ampicillin and 1 mM isopropyl β-D-thiogalactoside for 6 h at 25° C., to induce the production of glutathione-S-transferase fusion proteins. The cells were harvested by centrifugation and resuspended in lysis buffer (10 mM Tris-HCl (pH 8.0), 0.4M NaCl, 5 mM $MgCl_2$, 5% (v/v) glycerol, 0.5 mM EDTA). The cells were centrifuged again and the pellet resuspended in lysis buffer. The cells were lysed by a cycle of freezing and thawing followed by four 10 sec bursts of sonication. Triton X-100 and PMSF was added to the lysed cells to the concentration of 1% (v/v) and 100 μg/ml, respectively. The lysed preparation was centrifuged and the supernatant was mixed with pre-swollen glutathione Sepharose4B beads and incubated at 20° C. for 2 min. After absorption, the beads were spun down, washed three times with 50 ml of 75 mM Hepes-KOH (pH 7.9) and 150 mM NaCl. The fusion protein were eluted by washing the beads in 200 μl of 75 mM Hepes-KOH, pH 7.9, 150 mM NaCl and 5 mM of reduced glutathione. Glycerol was added to the eluted protein to a final concentration of 10% (v/v) and aliquots were snap frozen in liquid nitrogen and stored at −80° C.

EXAMPLE 8

Gel mobility shift assays

Complementary oligonucleotides with 5' overhangs containing native and mutant sequences of the high-pI amylase promoter ("149 to "128) were synthesised: The nucleotide sequences of the oligonucleotides used are shown in Table 2.

TABLE 2

Oligonucleotides used in gel retardation assays

| Oligo-nucleo-tide | Nucleotide sequence* | |
|---|---|---|
| w | 5'-GGCCGATAACAAACTCCGG-3' | (SEQ ID NO:12) |
| m-1 | 5'-GGCCGACTCGAGACTCCGG-3' | (SEQ ID NO:13) |
| m-2 | 5'GGCCGATGACAAACTCCGG-3' | (SEQ ID NO:14) |
| m-3 | 5'-GGCCGATAACAGACTCCGG-3' | (SEQ ID NO:15) |
| m-4 | 5'-GGCCGATAACAAGCTCCGG-3' | (SEQ ID NO:16) |
| m-5 | 5'-GGCCGATAACAAAATCCGG-3' | (SEQ ID NO:17) |

*Only sequences of upper strands are shown. Lower strands are complementary sequences. Mutated nucleotide residues, relative to the wild-type sequence, are indicated in bold typeface.

After annealing the complementary oligonucleotides were 3' end-labelled using $^{32}$P-dCTp and the Klenow fragment, and purified by electrophoresis on polyacrylamide gels. Bacterially-produced GAMYB fusion protein-oligonucleotide binding reactions were performed in 10 µl binding buffer (24 mM Hepes-KOH pH 7.9, 50 mM KCl, 0.5 mM EDTA, 0.5 mM dithiothreitol, 10% (v/v) glycerol) with 2 µg of poly(dI-dC)-poly(dI-dC), 150 ng of GAMYB fusion protein and 0.9 ng of a $^{32}$P-labelled oligonucleotide probe (40,000 cpm). After incubation at 20° C. for 10 min, the samples were run on a 6% (w/v) polyacrylamide gel containing 5% (v/v) glycerol, in 0.25 x Tris-borate-EDTA buffer at 140 volts. After electrophoresis, the gels were dried and autoradiographed.

EXAMPLE 9

GAMyb binds to the α-amylase promoter

To test whether GAMYB binds to the TAACAAA box in the high-pI α-amylase promoter, we performed gel-retardation experiments as described in Example 8. We looked for binding between an oligonucleotide probe (w) containing the amylase promoter sequence (−149 to −128), including the wild-type TAACAAA box and an affinity-purified glutathione-s-transferase (GST)-GAMYB fusion protein that had been expressed in Escherichia coil according to Example 7. As shown in FIG. 6, the GST-GAMYB fusion protein bound to probe w, resulting in the formation of a retarded complex (lane 3). In contrast, the GST protein alone failed to bind (lane 2). Cold competition with 100 fold molar excess of the unlabelled w fragment, completely abolished complex formation between the w probe and GAMYB fusion protein, indicating that binding is reversible. Experiments were also performed using mutant oligonucleotide probes (m-1 to m-5). As shown in FIG. 6, GAMYB only bound to the m-3 probe, confirming that GAMYB can bind to the mutated sequence TAACA<u>G</u>Ac, which resembles the TAACAAA box counterpart, in barley low-pI α-amylase promoters.

To determine the binding site of the GAMyb within the 22 bp w probe, we used a series of mutant probes containing single (m-2 to m-5) and multi(m-1) base pair mutations as unlabeled competitors for binding to the wild-type (w) probe. Extensive mutation of the TAACAAA box of <u>CTCGAGA</u> in the m-1 probe, abolished binding of the GAMYB (FIG. 7a, lane 4) indicating that the GAMYB binding site includes at least part of the TAACAAA box. A similar mutation of the TAACAAA box in the α-amylase promoter had been previously shown to cause a decrease in GA-induced expression in transient expression analyses (Gubler and Jacobsen, 1992).

As shown in FIG. 7b, GAMYB fails to bind m-2 (lane 5) which contains a single base pair mutation (T<u>G</u>CAAAc) in the AAC core of the 5' putative MYB binding site. In contrast, a similar mutation in the 3' putative binding site (A <u>G</u>Actccg) had no effect on GAMYB binding (FIG. 7b, lane 6). These results indicate that the GAMYB binds to the 5' MYB binding site, TAACAAAc and not the 3' site. Further single mutations of the GAMYB binding site, TAACAAAc were introduced to confirm the 3' end of the binding site. GAMYB failed to bind to m4 and m-5 (FIG. 7b, lanes 7 and 8) which carry single mutations at the 3' end of the hexameric binding site.

EXAMPLE 10

Transient expression analyses

Barley Himalaya half-seeds were prepared for particle bombardment as described by Lanahan et al., (1992). Plasmid constructs used for transient expression analyses were as described in Example 6. Plasmid DNA purified on Qiagen-tips (Qiagen, Hilden,: Germany) was coated onto 1.6 µm gold particles, essentially as described by Hunold et al. (1994). For expression analysis of mutant α-amylase promoter constructs, 0.5 µg Am(−174)IGN, or mTAACAAA-2, or mTAACAAA-3 constructs were precipitated onto 0.75 mg of gold. For experiments involving GAMyb gene overexpression, 1.5 µg of effector constructs (pAct1.GAMyb or pAct1.C1) and 0.5 µg of reporter constructs [Am(−174)IGN or mTAACAAA] were precipitated onto 0.75 mg of gold. An internal standard (ubiquitin promoter-luciferase reporter construct) was not used in these experiments because of difficulties ascertaining whether overexpression of GAMyb or C1 had any effect on the expression of the internal standard. Each experiment was highly-replicated (n>12). The conditions used for bombardment using a helium particle inflow gun (Finer et al., 1992) were the same as those described in Gubler et al. (1995) but with one modification. Six barley half grain were used per shot, instead of eight. After shooting, the six half seeds were cut longitudinally along the groove resulting in two equal quarter-grains which were then distributed into flasks containing 10 mM CaCl$_2$ (control) or 10 mM CaCl$_2$ and 1 µm GA$_3$. Both incubation solutions contained cefotaxime and nystatin, at the same concentrations as described in Example 3. After incubation for 24 h at 25° C., the shot grains were frozen and stored at −70° C. Soluble protein extracts were prepared and assayed for GUS enzyme activity as described previously (Gubler et al., 1995).

The GAMYB binding site, TAACAAAc, has been shown to be functional in transient expression assays. The clustered point mutations introduced in the m-1 sequence, which abolished GAMYB-binding, has previously been shown to greatly reduce the GA-responsiveness of the high-pI α-amylase promoter in transient expression experiments (Gubler and Jacobsen, 1992). To further test whether the GAMYB binding site is functionally important in conferring GA-responsiveness to the α-amylase promoter, mutations used in the binding studies were introduced into the construct Am(−174)IGN and the mutant promoter constructs were analysed by transient expression. As shown in FIG. 8, the introduction of a single base pair mutation, T GACAAAc, which abolished GAMYB-binding (FIG. 7), strongly reduced GA-regulated expression. In contrast, the mutation TAACA<u>G</u>Ac had no effect on reporter gene expression or GAMYB binding. These results indicate that there is a close correlation between GAMYB binding site and sequences which are functionally important in the GA-response.

EXAMPLE 11

The GAMYB polypeptide is a transcriptional activator of a high-pI α-amylase gene promoter To test the in vivo function of the protein encoded by the GAMyb cDNA, we determined whether GAMYB could transactivate a high-pI α-amylase gene promoter: GUS construct. Barley aleurone tissue was co-shot with a GUS reporter gene fused to an high-pI α-amylase promoter [Am (-174)IGN) and a GAMyb effector plasmid as described in preceding Example 10 (FIG. 5). The effector plasmid consisted of a rice actin1 promoter fused to the GAMyb cDNA. FIG. 9 shows that reporter GUS activity which is normally induced by $GA_3$ was also induced in the absence of $_3GA$ by the GAMyb effector construct. The increase in GUS activity in response to GAMyb expression was similar to that found with $GA_3$ alone. Mutation of the TAACAAA box in the α-amylase promoter (as in the m-1 sequence in Table 2) greatly reduced the response of the reporter construct to $GA_3$ and the GAMyb effector construct. These results indicate that GAMYB is a transcriptional activator which activates high-pI α-amylase gene expression in barley aleurone cells. In addition, the results provide functional evidence for the GAMYB transcription factor activating expression via the TAACAAA box, a binding site for this transcription factor.

To test whether other plant MYBs can activate the α-amylase promoter, the maize C1 cDNA was fused to the rice actin1 promoter (FIG. 5) and co-shot with Am(−174) IGN. In transient expression analyses (FIG. 9), the maize C1 cDNA failed to transactivate the reporter gene. Furthermore, expression of the C1 cDNA partially inhibited the $GA_3$ response.

EXAMPLE 12

The GAMYB polypeptide is a transcriptional activator of a number of GA-responsive gene promoters To test whether GAMYB could transactivate promoters of other genes which are expressed in aleurone cells in response to $GA_3$, we co-bombarded aleurone cells with reporter constructs containing GUS genes fused to the promoters of the barley Amy32b gene (mlo22; described in Lanahan et al., 1992), the barley EII-(1-3, 1-4)-β-glucanase gene (EII.IGN; the construct contains 1600 bp of the promoter fused to the reporter gene cassette IGN), and the wheat Cathepsin β-like gene, A121 (CBG1, described in Cejudo et al., 1992). As a control, we also tested whether GAMYB could transactivate an ABA-responsive gene promoter Dhn7 fused to the reporter gene cassette IGN [Dhn7 (−935).IGN, described in Robertson et al., 1995). The effector plasmid consisted of the rice actin1 expression cassette p113 Act1.cas (Example 6) with and without the GAMyb cDNA.

FIG. 10 shows that reporter activity driven by the Amy 32b, EII and A121 gene promoters were induced by the GAMYB effector construct in the absence of $GA_3$. The increase in GUS activity in response to GAMYB expression was higher than that found with $GA_3$ alone for all constructs. GAMYB only weakly transactivated the Dhn7 gene promoter. These results indicate that GAMYB is a transcriptional activator not only of α-amylase genes but other GA-responsive genes expressed in cereal aleurone. These include the EII-glucanase gene and a protease gene, A121.

EXAMPLE 13

A model of the GA response signal transduction pathway

While not being bound by any theory, or mode of action, these data suggest that GAMyb gene expression is required for the expression of genes encoding malting enzymes, for example α-amylase, amongst others. In fact, it is likely that the GAMYB polypeptide is required for the expression of genes encoding all malting enzymes and acts as a "master switch" in the regulation of these genes. The preceding examples indicate that GAMyb gene expression in barley aleurone layers, is induced by gibberellin. Comparison of the kinetics of expression indicates that GAMyb expression is an early event, in the GA response pathway, and precedes α-amylase expression. Our results provide three lines of evidence to support this proposal. Firstly, we showed that GAMYB fusion protein binds to a GARC cis-acting element, the TAACAAA box, in a barley high-pI α-amylase gene promoter (Example 9). By introducing mutations into the TAACAAA box and adjoining 3' sequence, the binding site was mapped to include the sequence TAACAAAc. Secondly, there is a strong correlation between the GAMYB binding site as defined in vitro and the sequences which are functionally important in transient expression assays (compare Example 9 and Example 10). We showed that oligonucleotides containing multiple or single point mutations in the TAACAAAc binding site that abolish binding to GAMYB fusion protein also reduced the GA-responsiveness of the high-pI α-amylase promoter. This provides strong evidence that the GAMYB protein functions in vivo to activate α-amylase gene expression through the TAACAAA box. Thirdly, we demonstrated in transient expression experiments that GAMYB activates transcription of several GA-responsive genes expressed in cereal aleurone, including the activation of a high-pI α-amylase promoter, the barley Amy32b promoter, the barley EII-(1-3, 1-4)-p-glucanase promoter and the wheat A121 promoter fused to a GUS reporter gene in the absence of $GA_3$ (Examples 11 and 12). Mutation of the TAACAAA box greatly reduced the ability of GAMYB to transactivate the α-amylase promoter construct, confirming that the TAACAAA box is the site of GAMYB binding and transactivation.

FIG. 11 shows a model of the GA response pathway between the expression of the high-pI α-amylase gene and the initial GA signal, based on our results. In this model, GA binds to a receptor, presumably on the plasmamembrane and activates a signal transduction pathway which triggers GAMyb gene expression. The newly synthesised GAMYB protein in its turn activates the expression of the high-pI α-amylase gene. Our results indicate that the GAMYB is the sole GA-regulated transcription factor required for transcriptional activation of the high-pI α-amylase gene. In the absence of GA, we were able to activate high-pI α-amylase gene transcription by transiently expressing GAMyb, under the control of a constitutive promoter. Other transcription factors which are presumably necessary for high-pI α-amylase gene expression (eg factors which may bind to the pyrimidine and TATTCCAC boxes) are likely to be present in aleurone cells that have not been treated with GA.

The wide occurrence of TAACAAA box like sequences in promoters of other genes which are expressed in cereal aleurone cells in response to GA (Huang et al., 1990) may indicate a broad action of the GAMYB protein. Detection of a nuclear factor from barley aleurone layers which binds to TAACAGA box and associated 3' sequences a barley low-pI α-amylase promoter in a GA-dependent manner: (Sutliff et al., 1993) is consistent with our model shown in FIG. 11. It seems probably that the binding factor is likely to be GAMYB or a GAMYB complex, since GAMYB was shown in this present study to bind to m3 probe which contains the sequence TAACAGA. Other GA-responsive gene promoters also contain sequences which resemble the GAMYB-binding site in the barley high-pI α-amylase promoter. Deletion analysis in the 5' region of the barley EII (1-3, 1-4)-β-glucanase gene promoter (Wolf, 1992) and wheat cathepsin B-like gene promoter (Cejudo et al., 1992) showed that the GA-responsive regions were downstream of −310 and −173, respectively. The sequence between −169 and −162 in EII β-glucanase promoter, TAACAACC, is very similar to the GAMYB binding site with only one base mismatch. Thus, GAMYB may also play a crucial role in regulation of the barley aleurone β-glucanase gene. The sequence between −140 and −135, GAACCGAA, in the cathepsin B-like gene promoter may act as a binding site for a wheat GAMYB homologue.

EXAMPLE 14

Cloning of a cDNA encoding rice GAMyb

To isolate cDNA clones encoding rice GAMyb (OsGAMyb), a cDNA library made from gibberellin-treated embryoless-half grains (Chen et al., 1995) was screened using a partial genomic clone isolated by screening a IR36 rice genomic library (Clontech) with a barley 3' GAMyb probe at low stringency (2×SSC, 0.1% SDS at 54° C.). Positive hybridising clones were identified: Six plaques were picked and isolated for further analysis.

The nucleotide sequence of the rice GAMyb (OsGAMyb) cDNA clone was determined and is set forth in SEQ ID No: 3. The nucleotide sequence contained a single open reading frame, from residues 396 to 2054 of SEQ ID NO:3, which encodes for a MYB-like polypeptide comprising 553 amino acids residues in length (molecular weight 59 kDa).

Comparison of the amino acid sequences of rice and barley GAMYB polypeptides (i.e. SEQ ID NO:2 compared to SEQ ID NO:4), revealed 88% identity overall (FIG. 12). There is very high sequence identity between the DNA binding domains of both MYB polypeptides. Furthermore the R2 and R3 repeats of the amino acid sequences of barley and rice GAMYBs show high sequence identity (99%), indicating that both MYBs are likely to have very similar binding specificities. Sequences downstream of the DNA binding domain up to and including a putative activator domain (amino acid residues 372 to 386 of the OsGAMYB amino acid sequence set forth in SEQ ID No: 4) are also highly conserved. Sequences downstream of the activator domain are approximately 75% conserved in barley and rice GAMYB polypeptides.

Based on the high level of sequence identity at the amino acid level, the rice cDNA is likely to encode the rice homologue of the HvGAMyb cDNA clone described herein.

EXAMPLE 15

Analysis of rice GAMyb gene expression in response to GA

The effect of GA on rice GAMyb (OsGAMyb) gene expression was monitored by incubating hydrated endosperm half grains of rice in the presence and absence of GA up to 12 h. RNA was extracted and analysed by RNA gel blot analysis using the 3' OsGAMyb PCR product.

As shown in FIG. 13a the probe detected only a single band of 3.5 kb in size. The abundance of OsGAMyb mRNA levels increased rapidly in response to GA. Within 1 h incubation with GA, OsGAMyb mRNA levels began to increase and continued to increase up to 12 h. In the absence of GA, OsGAMyb MRNA levels decreased continuously. Very low levels of OsGAMyb mRNA were detected in endosperm of dry grains (data not shown) compared to hydrated grains indicating that mRNA accumulated in the aleurone cells during the 24 h hydration period but subsequently declined in the absence of GA.

The accumulation of α-amylase mRNA in response to GA is shown in FIG. 3b. The increase in OsGAMyb mRNA levels in response to GA, preceded the rise in α-amylase mRNA which is similar to that found for barley GAMyb (HvGAMyb) gene expression in barley aleurone cells (Example 3).

EXAMPLE 16

The OsGAMYB polypeptide is a transcriptional activator of the α-amylase gene promoter To test whether OsGAMYB is a transcriptional activator of α-amylase gene promoters, barley aleurone cells were co-bombarded with the GUS reporter gene fused to a barley low-pI α-amylase promoter (mlo22; Lanahan et al., 1992) and with the GAMyb (OsGAMyb) effector construct (FIG. 14). As shown in FIG. 14a, the effector construct Ubi1.OsGAMyb comprised the OsGAMyb cDNA operably connected to the constitutive maize ubiquitin1 promoter (Christiensen et al., 1992).

The OsGAMyb effector was able to transactivate the low-pI α-amylase promoter both in the presence and absence of GA. As shown in FIG. 4b, the effector construct resulted in a 176-fold increase GUS expression in non-GA treated aleurone cells, compared to an effector construct which had no cDNA insert (Ubi1.cass). In construct, the increase in GUS activity observed with the Ubi1.OsGAMyb effector construct, in response to overexpression of the OsGAMyb cDNA, was only 2-fold higher in GA-treated aleurone cells bombarded with the Ubi.cass effector construct which contains no GAMyb sequence. These results indicate that the OsGAMyb cDNA encodes a transcriptional activator of the low-pI α-amylase gene promoter.

On the basis of high sequence identity, responsiveness to GA and functional evidence, the OsGAMyb gene described herein encodes the orthologue to HvGAMyb.

Furthermore, the results presented herein indicate that a MYB or MYB-like protein plays an important role in the hormonal control α-amylase gene expression in rice and barley aleurone cells. Sequence analysis of cereal α-amylase promoters shows that the MYB binding site, TAACAAA box is highly conserved in the promoters of barley, wheat and rice (Huang et al. 1990). It is of interest to note that another early gibberellin in response gene has been identified in rice aleurone (Chen et al., 1995). The expression of gene encoding ubiquitin-activating enzyme was shown to respond within 1 h of GA application.

EXAMPLE 17

Production of antibodies to barley GAMYB

Two synthetic peptides based on the sequence of the barley GAMYB amino acid sequences MYRVKSESD-CEMMHC (i.e. amino acids 1–14 of SEQ ID NO: 1) and CGAGDTSSHPENLRP (amino acids 481–494 of SEQ ID NO: 1) were synthesised at the Biomolecular Resource Facility, John Curtin School of Medical Research, Australian National University, Australia. The peptides were coupled to keyhole limpet haemocyanin with glutaraldehyde and used for immunisation of 3 months-old New Zealand White rabbits. Pre-immune sera were collected prior to the primary immunisation. The rabbits were given boost immunisations at 1, 2, 4, 5 and 10 weeks. Sera were collected and the IgG fractions were purified by Protein G columns as described the manufacturer's instruction (Pharmacia, Upsala).

Pre-immune antibodies and immune antibodies were tested for immunoreactivity to GAMYB fusion protein by Western Blot analysis. The GAMYB fusion protein was prepared as described in Example 7, separated on a 10% (w/v) SDS/polyacrylamide gel and transferred to PVDF membranes. The blots were probed with the purified antibodies followed by horseradish peroxidase linked goat anti-rabbit antibodies (Amersham, England). Blots were developed using a chemiluminescence substrate as described by the manufacturer's instructions (DuPont NEN).

The results presented in FIG. 15 show that the immune antibodies raised against both peptide recognise the GAMYB fusion protein.

Western blot analysis of barley grain proteins show that the immune antibodies also bind to native GAMYB protein. Because of the high similarity in amino acid sequence between barley and rice, it is expected that the anti-GAMYB antibodies will cross-react with other cereal GAMYB proteins.

EXAMPLE 18

Antisense GAMyb gene expression in rice plants blocks expression of α-amylase and other hydrolytic genes in aleurone cells in germinating grains The effector construct, Ubi1.asOsGAMyb (FIG. 16) was designed to express antisense GAMyb mRNA. The construct was made by inserting a fragment containing the 3' end of OsGAMyb cDNA sequence, in the antisense orientation, into the Ubi1.cass construct shown in FIG. 14a. Rice plants were transformed with this construct as described by Li et al., (1993).

Transgenic lines were confirmed by Southern blot hybridisation analysis using the 3' end of OsGAMyb as a probe. FIG. 17 shows restriction digestion of genomic DNA from transgenic lines probed with 3' end of the OsGAMyb cDNA. The results show that the transgenic lines contain the new construct.

Analysis of grains from the $T_1$ and subsequent generations show that expression of hydrolytic enzymes in aleurone cells of germinating grains is blocked in transgenic lines expressing antisense GAMyb mRNA.

EXAMPLE 19

Barley GAMyb gene expression increases early in germination

To test whether GAMyb is involved in germination and dormancy, GAMyb gene expression was monitored in embryos of germinating barley grains. RNA gel blots containing RNA from various timepoints were probed using a 3' gene specific HvGAMyb cDNA probe. Results were quantified using a Phosphorimager and normalised to rRNA levels (FIG. 18).

As shown in FIG. 18, GAMyb mRNA was detected in embryos of dry mature barley grains. Following the start of imbibition, GAMyb mRNA levels increased 3-fold in the first 12 h. The increase in GAMyb mRNA levels preceded germination. These results suggest that the barley GAMYB polypeptide is likely to be involved in germination.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In determining whether or not two amino acid sequences fall within a specified percentage limit, the GAP programme of Devereaux et al (*Nucl. Acids Res.* 12:387–395, 1984) is utilised. The GAP programme utilizes the algorithm of Needleman and Wunsch (*J. Mol. Biol.* 48:443–453, 1970) to maximise the number of identical/similar residues and to minimise the number and/or length of sequences gaps in the alignment.

REFERENCES

1. An et al. (1985) EMBO J. 4:277–284.
2. Ausubel, F. M., Brent, R., Kingston, R. E., Moore, D. D., Seidman, J. G., Smith, J. A. and Struhl, K. (1987) Current Protocols in Molecular Biology, Wiley Interscience (ISBN 047140338).
3. Bush, D. S. and Jones, R. L. (1990) Measuring intracellular $Ca^{2+}$ levels in plant cells using fluorescent probes, indo-1 and fura-2. Plant Physiol. 93:841–845
4. Cejudo, F. J., Ghose, T. K., Stabel, P., and Baulcombe, D. C. (1992) Plant Molecular Biology 20:849–856
5. Chandler, P. M., Zwar, J. A., Jacobson, J. V., Higgins, T. J. V., and Inglis, A. S. (1984) The effects of gibberellic acid and abscisic acid on α-amylase mRNA levels in barely aleurone layers studies using an α-amylase cDNA clone. Plant Mol. Biol. 3:407–418
6. Chandler, P. M. and Jacobsen, J. V. (1991) Primer extension studies on α-amylase mRNAs in barely aleurone. II. Hormonal regulation of expression. Plant Molec. Biol. 16: 637–645
7. Chen, X., Wang, B. and Wu, R. (1995) A gibberellin-stimulated ubiquitin-conjugating enzyme gene is involved in α-amylase gene expression in rice aleurone. Plant. Mol. Biol. 29:
8. Chen , M. J. and Varner, J. E. (1967) Gibberellic acid-enhanced synthesis and release of α-amylase and ribo-nuclease by isolated barley aleurone layers. Plant Physiol. 42: 398–406
9. Christensen A. H., Sharrock, R. A., Quail, P. H. (1992) Maize ubiquitin genes: structure, thermal perturbation of expression and transcript splicing, and promoter activity following transfer to protoplasts by electroporation. Plant. Mol. Biol. 20: 849–856.
10. Crossway et al. (1986) Mol. Gen. Genet. 202:179–185.
11. Dellaporta, S. L., Wood, J., Hicks, J. B. (1983) A plant DNA minipreparation: version II. Plant Mol. Biol. Rep, 1:19–21
12. Feinberg, A. P. and Vogelstein, B. (1983) A technique for radiolabelling DNA restriction endonuclease fragments to high specific activity. Anal. Biochem. 132:6–13
13. Fincher, G. B. (1989) Ann. Rev. Plant. Physiol. Mol. Biol. 40:305–346.
14. Finer, J. J., Vain, P., Jones, M. W. McMullen, M. D. (1992) Development of the particle inflow gun for DNA delivery to plant cells. Plant Cell Reps. 11:323–328
15. Frohman, M. (1990) RACE: rapid amplification of cDNA ends. In PCR protocols: a guide to methods and applications, M. A. Innis, D. H. Gelfand, J. J. Sninsky, and T. J. White, eds (Academic Press, Sandeigo), pp. 28–38.
16. Fromm et al. (1985) Proc. Natl. Acad. Sci. (USA) 82:5824–5828.

17. Gerlach, W. L. and Bedbrook, J. R. (1979) Cloning and characterization of ribosomal RNA genes from wheat and barley. Nuc. Ac. Res 7:1869–1885

18. Gilroy, S. and Jones, R. L. (1992) Gibberellic acid and abscisic acid coordinately regulate cytoplasmic calcium/and secretory activity in barley aleurone protoplasts. Proc. Natl. Acad. Sci. USA 89: 3591–3595.

19. Gilroy, S. and Jones, R. L. (1994) Perception of gibberellin and abscisic acid at the external face of the plasma membrane of barley (Hordeum vulgare L.) aleurone protoplasts. Plant Physiol. 104:1185–1192

20. Goldman S., et al. (1994) Studies of a gibberellin-dependent DNA-binding protein related to the expression of a rice α-amylase gene. Plant Sci. 99:75–88

21. Gopalakrishnan, B., Sonthayanon, B., Rahmatullah, R., and Muthukrishnan, S. (1991) Plant Mol. Biol. 14:463–467.

22. Gubler, F. and Jacobsen, J. V. (1992) Plant Cell 4:1435–1441.

23. Gubler, F. Wallace, T., and Jacobsen, J. V. (1995) Functional analysis of the promoter of a barley high-pI α-amylase gene iin intact aleurone cells: definition of the gibberellin response complex. To be submitted to Plant Physiology 24. Gubler, F., Kalla, R., Roberts, J. K. and Jacobsen, J. V. (1995) Gibberellin-regulated expression of a myb gene in barley aleurone cells: evidence for Myb transactivation of a high-pI α-amylase gene promoter. Plant Cell 7: 1879–1891.

25. Haseloff, J., and Gerlach, W. L. (1988) Nature 334:586–594

26. Herrera-Estrella et al. (1983a) Nature 303:209–213.

27. Herrera-Estrella et al. (1983b) EMBO J. 2:987–995

28. Herrera-Estrella et al. (1985) In: Plant Generic Engineering, Cambridge University Press, NY, pp 63–93.

29. Hooley, R., Beale, M. H. and Smith, S. J. (1991) Gibberellin perception at the plasma membrane of *Avena fatua aleurone protoplaete*. Planta 183:274–280

30. Hooley, R., Beale, M. H., Smith, S. J., Walker, R. P., Rushton, P. J., Whittfoord, P. N. and Lazarus, C. M. (1992) Gibberellin perception at the *Avena fatua aleurone: do our molecular keys fit the correct locks?* Biochem. Soc. Trans. 20:85–89

31. Huang, N., Sutliff, T. D., Litts, J. C., and Rodriguez, R. L. (1990) Plant. Mol. Biol. 14:655–668.

32. Hunold, R., Bronner, R. and Hahne, G. (1994) Early events in microprojectile bombardment: cell viability and particle location. Plant J. 5:593–604

33. Huttley, A. K., and Baulcombe, D. C. (1989) EMBO J. 8:1907–1913

34. Jacobsen, J. V., and Close, T. J. (1991) Plant Mol. Biol. 16:731–724

35. Jacobsen, J. V., Gubler, F., and Chandler, P. M. (1995) Gibberellin action in germinated cereal grains. In: Plant Hormones: Physiology, Biochemistry and Molecular Biology. P. J. Davies ed (Kluwer Academic Publishers, Dordrecht, The Netherlands), pp 246–271

36. Jackson, D., Culianez-Marcia, F., Prescott, G. A., Roberts, K., and Martin, C. (1991) Expression patterns of myb genes from Antrrhinum flowers. Plant Cell 3:115–125

37. Lanahan, M. B., Ho, T.-H. D., Rogers, S. W., and Rogers, J. C. (1992) Plant Cell 4:203–211

38. Li, L., Qu, R., de Kochko, A., Fauquet, C. and Beachy, R. N. (1993) An improved rice transformation system using the biolistic method. Plant Cell Rep. 12: 250–255.

39. Ogata, K., Hojo, H., Aimoto, S., Nakkai, T., Nakamura, H., Sarai, A., Ishii, S., and Nishimura, Y. (1992) Solution structure of a DNA-binding unit of Myb: a helix-turn-helix-related mootif with conserved typtophans forming a hydrophobic core. Proc. Nat. Acad. Sci. USA 89:6428–6432

40. Ou-Lee, T.-M., Turgeon, R., and Wu, R. (1988) Proc. Natl. Acad. Sci. (USA) 85:6366–6369

41. Paleg, L. G. (1960) Plant Physiol. 35:902–906

42. Paszkowski et al. (1984) EMBO 3. 3:2717–2722

43. Robertson, M., Cunning, A. C., Chandler, P. M. (1995) Physiol. Planetarium 94: (in press)

44. Rushton, P. J., Hooley, R., and Lazarus, C. M. (1992) Plant Mol. Biol. 19:891–901

45. Salmenkallio, M., Hannus, K., Teeri, T. H., and Kauppinen, V. (1990) Plant Cell Reports 9:352–355

46. Sambrook J., Fritsch, E. F., and Maniatis, T. (1989) Molcular Cloning, A Laboratory Manual. Cold Spring Harbor, NY: Cold Spring Harbor Laboratory Press.

47. Skriver, K., Olsen, F. L., Rogers, J. C., and Mundy, J. (1991) Proc. Natl. Acad. Sci. (USA) 88:7266–7270

48. Smith, D. and Johnson, K. S. (1988) Single-step purification of polypeptides expressed in *Escherichia coli* as fusions with glutathione S-transferase. Gene 67:31–40

49. Sutliff, T. D., Lanahan, M. B., and Ho, T.-H. (1993) Gibberellin treatment stimulates nuclear factor binding to the gibberellin response complex in a barley α-amylase promoter. Plant Cell 5:1681–1692

50. Varner, J. E. (1964) Plant Physiol. 39:413–415

51. Wolf, N. (1992) Mol. Gen. Genet. 234:33–42

52. Yomo, H. (1960) Hakko Kyokaishi 18:600–602

What is claimed is:

1. An isolated nucleic acid molecule comprising a coding sequence encoding a polypeptide that regulates the expression of one or more gibberellin-regulated genes or a fully complementary nucleotide sequence thereto wherein said polypeptide has 88% or greater amino acid sequence identity overall to SEQ ID NOs, 2 or 4, wherein each of said amino acid identities is calculated using an algorithm that maximizes the number of identical residues in an alignment between two or more proteins and minimizes the number of gaps in said alignment.

2. The isolated nucleic acid molecule according to claim 1 wherein said polypeptide regulates the expression of one or more gibberellin-regulated genes encoding hydrolytic enzymes involved in the malting process.

3. The isolated nucleic acid molecule according to claim 2 wherein the hydrolytic enzymes are selected from the list consisting of the high pI α-amylase, low pI α-amylase, EII-(1-3, 1-4)-β-glucanase, cathepsin β-like protease, α-glucosidase, xylanase and arabinofuranosidase.

4. The isolated nucleic acid molecule of claim 1, wherein said nucleic acid molecule hybridizes to the nucleotide sequence set forth in SEQ ID NO:1 or SEQ ID NO:3 using hybridization conditions comprising 2×SSC, 0.1 (w/v) % SDS at 54° C.

5. A bacterial cell transformed with the isolated nucleic acid molecule according to claim 4.

6. A plant cell or whole plant or the progeny thereof transformed with the isolated nucleic acid molecule according to claim 4.

7. A bacterial cell transformed with the isolated nucleic acid molecule according to claim 1.

8. A plant cell transformed with the isolated nucleic acid molecule according to claim 1.

9. A transgenic plant regenerated from the cell according to claim 8 or the progeny of said transgenic plant.

10. A method of modulating the expression of a GAMYB-regulated gene or GAMYB-regulated polypeptide in a plant comprising the steps of:

(i) transforming a plant cell with the isolated nucleic acid molecule according to claim 1; and (ii) regenerating said cell into a whole plant.

11. The method according to claim 10 wherein the GAMYB-regulated gene or GAMYB-regulated polypeptide is involved in a plant developmental process selected from the list consisting of stem elongation, flowering, leaf development, fruit set, fruit growth, sex determination, and germination, or determines a malting characteristic of a plant.

12. The method according to claim 11 wherein the malting characteristic is selected from the list consisting of dormancy, germination, post-kilning levels of hydrolytic enzymes, mash filtration properties, precipitate formation and alcohol content.

13. The method according to claim 12 wherein the hydrolytic enzyme is selected from the list consisting of high pI α-amylase, low pI α-amylase, EII-(1-3, 1-4)-β-glucanase, cathepsin β-like protease, α-glucosidase, xylanase and arabinofuranosidase.

14. A method of improving the malting characteristics of a monocotyledonous plant, plant seed or other plant organ comprising the steps of:

(i) transforming a plant cell with the isolated nucleic acid molecule according to claim 1; and (ii) regenerating said cell into a whole plant.

15. The method according to claim 14 wherein the malting characteristics are selected from the group consisting of dormancy, germination, post-kilning levels of hydrolytic enzymes, mash filtration properties, precipitate formation and alcohol content.

16. The method according to claim 15 wherein by virtue of the expression of said nucleic acid molecule or said genetic construct the regenerated plant exhibits one or more improved malting characteristics selected from the group consisting of: (i) more rapid filtration of the mash; (ii) reduced cloudy precipitate formation in the product of the malting process; (iii) more uniform germination of seed during malting; (iv) higher or lower alcohol content in the product of the malting process; and (v) high post-kilning levels of hydrolytic enzymes required during malting.

17. The method according to claim 16 wherein the hydrolytic enzyme is selected from the group consisting of high pI α-amylase, low pI α-amylase, EII-(1-3, 1-4)-β-glucanase, cathepsin β-like protease, α-glucosidase, xylanase and arabinofuranosidase.

18. An isolated nucleic acid molecule that encodes a polypeptide and comprises the protein-encoding nucleotide sequence set forth in SEQ ID NO:1 or SEQ ID NO:3 or a fully complementary nucleotide sequence thereto.

19. An antisense genetic construct comprising in the antisense orientation the Myb genetic sequence set forth in SEQ ID NO:1 or SEQ ID NO:3 or a region thereof sufficient to reduce expression of an endogenous Myb genetic sequence in a plant cell, tissue or organ in operable connection with a promoter sequence.

20. A genetic construct comprising the protein-encoding region of a gibberellin-regulated Myb genetic sequence placed operably in connection with a promoter in the sense orientation such that a polypeptide is capable of being expressed under the control of said promoter wherein the Myb genetic sequence is the barley GAMyb sequence (HvGAMyb) set forth in SEQ ID NO: 1 or the rice OsGAMyb sequence (OsGAMyb) set forth in SEQ ID NO:3.

21. A bacterial cell transformed with the genetic construct according to claim 20.

22. A plant cell transformed with the genetic construct according to claim 20.

23. A method of modulating the expression of a GAMYB-regulated gene or GAMYB-regulated polypeptide in a plant comprising the steps of:

(i) transforming a plant cell with the genetic construct according to claim 20; and (ii) regenerating said cell into a whole plant.

24. A method of improving the malting characteristics of a monocotyledonous plant, plant seed or other plant organ comprising the steps of:

(i) transforming a plant cell with the genetic construct according to claim 20; and (ii) regenerating said cell into a whole plant.

25. An isolated nucleic acid molecule comprising a coding sequence encoding a polypeptide that regulates the expression of one or more gibberellin-regulated genes or a fully complementary nucleotide sequence thereto wherein said polypeptide has 75% or greater amino acid sequence identity overall to SEQ ID NOs: 2 or 4, wherein each of said amino acid identities is calculated using an algorithm that maximizes the number of identical residues in an alignment between two or more proteins and minimizes the number of gaps in said alignment.

* * * * *

UNITED STATES PATENT AND TRADEMARK OFFICE
CERTIFICATE OF CORRECTION

PATENT NO.    : 6,271,440 B1
DATED         : August 7, 2001
INVENTOR(S)   : Gubler et al.

It is certified that error appears in the above-identified patent and that said Letters Patent is hereby corrected as shown below:

Title page,
Under Item [73], Assignee, replace "Australian National University" with
-- Commonwealth Scientific and Industrial Research Organization --.

Under References Cited PUBLICATIONS, please replace "promter regions" with
-- promoter regions --.

Column 5,
Line 11, replace "whir one" with -- which one --.

Column 7,
Line 9, replace "28º C.-55ºC." -- with -- 28ºC-55ºC. --.

Column 10,
Line 1, replace "amino-o" with -- amino– or --.

Column 13,
Lines 10 and 38, replace "MRNA" with -- mRNA --.
Line 42, replace "target" with -- targets --.
Line 50, replace "least S contiguous" with -- least 5 contiguous --.
Line 62, replace "MRNA" with -- mRNA --.

Column 15,
Lines 61-62, replace "promoter" with -- promoter, --.

Column 18,
Line 64, replace "polypeptides and." with --polypeptide. --.

Column 20,
Line 49, replace "SEQ ID NO.7.", with -- (SEQ ID NO:7). --
Line 54, replace "SEQ ID NO:8", with -- (SEQ ID NO:8) --

Column 21,
Line 37, repalce "BgLII site" with BglII site --.

Column 23,
Line 48, repalce "high-pi et-amylase" with -- high-pI α–amylase --.

UNITED STATES PATENT AND TRADEMARK OFFICE
CERTIFICATE OF CORRECTION

PATENT NO. : 6,271,440 B1
DATED : August 7, 2001
INVENTOR(S) : Gubler et al.

It is certified that error appears in the above-identified patent and that said Letters Patent is hereby corrected as shown below:

Column 23,
Lines 55-58, replace
"mTAA11 (5'-GCCTGCAGGTCGACTCTAGAGAATCGCCTTTGAGCTCACCGTACCGGCCAT<u>G</u>ACAAACTCCGG-3" (SEQ ID NO:9))"
with
-- MTAA11 (5'-GCCTGCAGGTCGACTCTAGAGAATCGCCTTTTGAGCTCACCGTACCGGCCGAT<u>G</u>ACAAACTCCGG-3" (SEQ ID NO:9)) --.

Lines 59-62, replace
"MTAA12 )5'-GCCTGCAGGTCGACTCTAGAGAATCGCCTTTTGAGCTCACCGTACCGGCCGATAACA<u>G</u>ACTCCGG-3" (SEQ ID NO:10))"
with
-- m TAA12 (5'-GCCTGCAGGTCGACTCTAGAGAATCGCCTTTTGAGCTCACCGTACCGGCCGATAACA<u>G</u>ACTCCGG-3" (SEQ ID NO:10)) --.

Column 24,
Line 65, replace "("149 to "128)" with -- (-149 to -128) --.

Column 25,
Line 19, replace "$^{32}$P-dCTp" with -- $^{32}$P-dCTP --.
Line 25, repalce "poly(dI-dC)-poly(dI-dC)" with -- poly(dI-dC) --

Column 27,
Line 13, replace "$_3$GA" with -- $GA_3$ --

UNITED STATES PATENT AND TRADEMARK OFFICE
CERTIFICATE OF CORRECTION

PATENT NO. : 6,271,440 B1
DATED : August 7, 2001
INVENTOR(S) : Gubler et al.

It is certified that error appears in the above-identified patent and that said Letters Patent is hereby corrected as shown below:

Column 30,
Line 6, replace "is shown in FIG. 3*b*" with -- is shown in FIG. 13*b* --.
Line 27, replace "As shown in FIG. 4*b*" with -- As shown in FIG. 14*b* --.
Line 48, replace "gibberellin in response gene" with -- gibberellin response gene --

Signed and Sealed this

Eighteenth Day of June, 2002

*Attest:*

*Attesting Officer*

JAMES E. ROGAN
*Director of the United States Patent and Trademark Office*